US012076160B2

(12) United States Patent
Mazlish et al.

(10) Patent No.: US 12,076,160 B2
(45) Date of Patent: Sep. 3, 2024

(54) ALARMS AND ALERTS FOR MEDICATION DELIVERY DEVICES AND SYSTEMS

(71) Applicant: Bigfoot Biomedical, Inc., Milpitas, CA (US)

(72) Inventors: Bryan Mazlish, Palo Alto, CA (US); Sabine Kabel-Eckes, Mountain View, CA (US); Shannon Sieber, Santa Clara, CA (US); Jeff Boissier, San Jose, CA (US); George Crothall, Oceanside, CA (US); Yean Wah Chan, Irvine, CA (US)

(73) Assignee: Insulet Corporation, Acton, MA (US)

( * ) Notice: Subject to any disclaimer, the term of this patent is extended or adjusted under 35 U.S.C. 154(b) by 328 days.

(21) Appl. No.: 17/444,003

(22) Filed: Jul. 29, 2021

(65) Prior Publication Data

US 2021/0401367 A1    Dec. 30, 2021

Related U.S. Application Data

(63) Continuation of application No. 16/335,163, filed as application No. PCT/US2017/065894 on Dec. 12, 2017, now Pat. No. 11,096,624.

(Continued)

(51) Int. Cl.
*A61B 5/00* (2006.01)
*A61B 5/145* (2006.01)

(52) U.S. Cl.
CPC ............ *A61B 5/4839* (2013.01); *A61B 5/002* (2013.01); *A61B 5/14532* (2013.01); *A61B 5/746* (2013.01); *A61B 5/4848* (2013.01)

(58) Field of Classification Search
CPC ... A61B 5/002; A61B 5/0022; A61B 5/14532; A61B 5/4839; A61B 5/4848; A61B 5/6833; A61B 5/746
See application file for complete search history.

(56) References Cited

U.S. PATENT DOCUMENTS

| 303,013 A | 8/1884 | Horton |
|---|---|---|
| 445,545 A | 2/1891 | Crane |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Deanna K Hall
(74) *Attorney, Agent, or Firm* — TraskBritt

(57) ABSTRACT

Systems, methods, and devices provide alarms and alerts in an on-body networked diabetes management system. Methods may include receiving glucose sensor data from a continuous glucose monitor and determining a dosage of insulin delivery based at least in part on the glucose sensor data. The method may include detecting an alarm or alert condition, and sending a wireless communication regarding the alarm or alert condition to a remote user-interface device. The method may include triggering an audible, visual, or haptic alarm or alert on the insulin delivery device unless an acknowledgement of the alarm or alert condition is received within a predetermined period of time.

17 Claims, 23 Drawing Sheets

Related U.S. Application Data

(60) Provisional application No. 62/433,124, filed on Dec. 12, 2016.

(56) References Cited

U.S. PATENT DOCUMENTS

| | | |
|---|---|---|
| 588,583 A | 8/1897 | Lade |
| 1,441,508 A | 1/1923 | Marius et al. |
| 2,283,925 A | 5/1942 | Harvey |
| 2,605,765 A | 8/1952 | Kollsman |
| 2,797,149 A | 6/1957 | Skeggs |
| 2,886,529 A | 5/1959 | Guillaud |
| 3,413,573 A | 11/1968 | Nathanson et al. |
| 3,574,114 A | 4/1971 | Monforte |
| 3,614,554 A | 10/1971 | Shield et al. |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,885,662 A | 5/1975 | Schaefer |
| 3,886,938 A | 6/1975 | Szabo et al. |
| 3,963,380 A | 6/1976 | Thomas et al. |
| 3,983,077 A | 9/1976 | Fuller et al. |
| 4,055,175 A | 10/1977 | Clemens et al. |
| 4,077,405 A | 3/1978 | Haerten et al. |
| 4,108,177 A | 8/1978 | Pistor |
| 4,146,029 A | 3/1979 | Ellinwood, Jr. |
| 4,151,845 A | 5/1979 | Clemens |
| 4,231,368 A | 11/1980 | Becker |
| 4,245,634 A | 1/1981 | Albisser et al. |
| 4,265,241 A | 5/1981 | Portner et al. |
| 4,268,150 A | 5/1981 | Chen |
| 4,295,176 A | 10/1981 | Wittwer |
| 4,300,554 A | 11/1981 | Hessberg et al. |
| 4,313,439 A | 2/1982 | Babb et al. |
| 4,368,980 A | 1/1983 | Aldred et al. |
| 4,373,527 A | 2/1983 | Fischell |
| 4,398,908 A | 8/1983 | Siposs |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,443,218 A | 4/1984 | Decant et al. |
| 4,464,170 A | 8/1984 | Clemens et al. |
| 4,469,481 A | 9/1984 | Kobayashi |
| 4,475,901 A | 10/1984 | Kraegen et al. |
| 4,493,704 A | 1/1985 | Beard et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,562,751 A | 1/1986 | Nason et al. |
| 4,573,968 A | 3/1986 | Parker |
| 4,585,439 A | 4/1986 | Michel |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,657,529 A | 4/1987 | Prince et al. |
| 4,678,408 A | 7/1987 | Nason et al. |
| 4,681,569 A | 7/1987 | Coble et al. |
| 4,684,368 A | 8/1987 | Kenyon |
| 4,685,903 A | 8/1987 | Cable et al. |
| 4,731,726 A | 3/1988 | Allen, III |
| 4,743,243 A | 5/1988 | Vaillancourt |
| 4,749,109 A | 6/1988 | Kamen |
| 4,755,169 A | 7/1988 | Sarnoff et al. |
| 4,755,173 A | 7/1988 | Konopka et al. |
| 4,759,120 A | 7/1988 | Bernstein |
| 4,781,688 A | 11/1988 | Thoma et al. |
| 4,781,693 A | 11/1988 | Martinez et al. |
| 4,808,161 A | 2/1989 | Kamen |
| 4,838,857 A | 6/1989 | Strowe et al. |
| 4,850,817 A | 7/1989 | Nason et al. |
| 4,854,170 A | 8/1989 | Brimhall et al. |
| 4,859,492 A | 8/1989 | Rogers et al. |
| 4,880,770 A | 11/1989 | Mir et al. |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,967,201 A | 10/1990 | Rich, III |
| 4,969,874 A | 11/1990 | Michel et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,045,064 A | 9/1991 | Idriss |
| 5,061,424 A | 10/1991 | Karimi et al. |
| 5,062,841 A | 11/1991 | Siegel |
| 5,084,749 A | 1/1992 | Losee et al. |
| 5,088,981 A | 2/1992 | Howson et al. |
| 5,088,990 A | 2/1992 | Hivale et al. |
| 5,097,834 A | 3/1992 | Skrabal |
| D325,781 S | 4/1992 | Moller-Jensen |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,662 A | 1/1993 | Bartholomew et al. |
| 5,178,609 A | 1/1993 | Ishikawa |
| 5,189,609 A | 2/1993 | Tivig et al. |
| 5,190,522 A | 3/1993 | Wojcicki et al. |
| 5,198,824 A | 3/1993 | Poradish |
| 5,205,819 A | 4/1993 | Ross et al. |
| 5,207,642 A | 5/1993 | Orkin et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,225,763 A | 7/1993 | Krohn et al. |
| 5,232,439 A | 8/1993 | Campbell et al. |
| 5,237,993 A | 8/1993 | Skrabal |
| 5,244,463 A | 9/1993 | Cordner et al. |
| 5,250,027 A | 10/1993 | Lewis et al. |
| 5,254,096 A | 10/1993 | Rondelet et al. |
| 5,257,980 A | 11/1993 | Van et al. |
| 5,261,882 A | 11/1993 | Sealfon |
| 5,263,198 A | 11/1993 | Geddes et al. |
| 5,272,485 A | 12/1993 | Mason et al. |
| 5,273,517 A | 12/1993 | Barone et al. |
| 5,281,202 A | 1/1994 | Weber et al. |
| 5,281,808 A | 1/1994 | Kunkel |
| 5,299,571 A | 4/1994 | Mastrototaro |
| 5,308,982 A | 5/1994 | Ivaldi et al. |
| 5,314,412 A | 5/1994 | Rex |
| 5,335,994 A | 8/1994 | Weynant Girones |
| 5,338,157 A | 8/1994 | Blomquist |
| 5,342,180 A | 8/1994 | Daoud |
| 5,342,298 A | 8/1994 | Michaels et al. |
| 5,346,476 A | 9/1994 | Elson |
| D351,469 S | 10/1994 | Okamoto |
| 5,364,342 A | 11/1994 | Beuchat et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,395,340 A | 3/1995 | Lee |
| 5,403,797 A | 4/1995 | Ohtani et al. |

(56) References Cited

U.S. PATENT DOCUMENTS

| | | |
|---|---|---|
| 5,411,487 A | 5/1995 | Castagna |
| 5,411,889 A | 5/1995 | Hoots et al. |
| 5,421,812 A | 6/1995 | Langley et al. |
| 5,427,988 A | 6/1995 | Sengupta et al. |
| 5,433,710 A | 7/1995 | Vanantwerp et al. |
| 5,456,945 A | 10/1995 | Mcmillan et al. |
| 5,468,727 A | 11/1995 | Phillips et al. |
| 5,478,610 A | 12/1995 | Desu et al. |
| 5,505,709 A | 4/1996 | Funderburk et al. |
| 5,505,828 A | 4/1996 | Wong et al. |
| 5,507,288 A | 4/1996 | Boecker et al. |
| 5,513,382 A | 4/1996 | Agahi-Kesheh et al. |
| 5,533,389 A | 7/1996 | Kamen et al. |
| 5,535,445 A | 7/1996 | Gunton |
| 5,540,772 A | 7/1996 | Mcmillan et al. |
| 5,543,773 A | 8/1996 | Evans et al. |
| 5,545,143 A | 8/1996 | Fischell et al. |
| 5,551,850 A | 9/1996 | Williamson et al. |
| 5,554,123 A | 9/1996 | Herskowitz |
| 5,558,640 A | 9/1996 | Pfeiler et al. |
| 5,569,186 A | 10/1996 | Lord et al. |
| 5,582,593 A | 12/1996 | Hultman |
| 5,584,053 A | 12/1996 | Kommrusch et al. |
| 5,584,813 A | 12/1996 | Livingston et al. |
| 5,590,387 A | 12/1996 | Schmidt et al. |
| 5,609,572 A | 3/1997 | Lang |
| 5,614,252 A | 3/1997 | Mcmillan et al. |
| 5,625,365 A | 4/1997 | Tom et al. |
| 5,626,566 A | 5/1997 | Petersen et al. |
| 5,635,433 A | 6/1997 | Sengupta |
| 5,637,095 A | 6/1997 | Nason et al. |
| 5,640,954 A | 6/1997 | Pfeiffer et al. |
| 5,665,065 A | 9/1997 | Colman et al. |
| 5,665,070 A | 9/1997 | Mcphee |
| 5,678,539 A | 10/1997 | Schubert et al. |
| 5,678,571 A | 10/1997 | Brown |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,707,459 A | 1/1998 | Itoyama et al. |
| 5,707,715 A | 1/1998 | Derochemont et al. |
| 5,713,875 A | 2/1998 | Tanner, II |
| 5,714,123 A | 2/1998 | Sohrab |
| 5,716,343 A | 2/1998 | Kriesel et al. |
| 5,718,562 A | 2/1998 | Lawless et al. |
| 5,722,397 A | 3/1998 | Eppstein |
| D393,264 S | 4/1998 | Leung |
| 5,741,216 A | 4/1998 | Hemmingsen et al. |
| 5,741,228 A | 4/1998 | Lambrecht et al. |
| 5,746,217 A | 5/1998 | Erickson et al. |
| 5,747,350 A | 5/1998 | Sattler |
| 5,747,870 A | 5/1998 | Pedder |
| 5,748,827 A | 5/1998 | Holl et al. |
| 5,755,682 A | 5/1998 | Knudson et al. |
| 5,758,643 A | 6/1998 | Wong et al. |
| 5,759,923 A | 6/1998 | Mcmillan et al. |
| 5,764,189 A | 6/1998 | Lohninger |
| 5,766,155 A | 6/1998 | Hyman et al. |
| 5,771,567 A | 6/1998 | Pierce et al. |
| 5,772,635 A | 6/1998 | Dastur et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | Mcphee |
| 5,800,420 A | 9/1998 | Gross et al. |
| 5,801,057 A | 9/1998 | Smart et al. |
| 5,804,048 A | 9/1998 | Wong et al. |
| 5,807,075 A | 9/1998 | Jacobsen et al. |
| 5,816,306 A | 10/1998 | Giacomel |
| 5,817,007 A | 10/1998 | Fodgaard et al. |
| 5,820,622 A | 10/1998 | Gross et al. |
| 5,823,951 A | 10/1998 | Messerschmidt |
| 5,839,467 A | 11/1998 | Saaski et al. |
| 5,840,020 A | 11/1998 | Heinonen et al. |
| D403,313 S | 12/1998 | Peppel |
| 5,848,991 A | 12/1998 | Gross et al. |
| 5,851,197 A | 12/1998 | Marano et al. |
| 5,852,803 A | 12/1998 | Ashby et al. |
| 5,854,608 A | 12/1998 | Leisten |
| 5,858,001 A | 1/1999 | Tsals et al. |
| 5,858,005 A | 1/1999 | Kriesel |
| 5,858,239 A | 1/1999 | Kenley et al. |
| 5,859,621 A | 1/1999 | Leisten |
| 5,865,806 A | 2/1999 | Howell |
| 5,871,470 A | 2/1999 | Mcwha |
| 5,879,310 A | 3/1999 | Sopp et al. |
| 5,889,459 A | 3/1999 | Hattori et al. |
| 5,891,097 A | 4/1999 | Saito et al. |
| 5,892,489 A | 4/1999 | Kanba et al. |
| 5,897,530 A | 4/1999 | Jackson |
| 5,902,253 A | 5/1999 | Pfeiffer et al. |
| 5,903,421 A | 5/1999 | Furutani et al. |
| 5,906,597 A | 5/1999 | Mcphee |
| 5,911,716 A | 6/1999 | Rake et al. |
| 5,918,603 A | 7/1999 | Brown |
| 5,919,167 A | 7/1999 | Mulhauser et al. |
| 5,925,018 A | 7/1999 | Ungerstedt |
| 5,928,201 A | 7/1999 | Poulsen et al. |
| 5,931,814 A | 8/1999 | Alex et al. |
| 5,932,175 A | 8/1999 | Knute et al. |
| 5,933,121 A | 8/1999 | Rainhart et al. |
| 5,935,099 A | 8/1999 | Peterson et al. |
| 5,945,963 A | 8/1999 | Leisten |
| 5,947,911 A | 9/1999 | Wong et al. |
| 5,947,934 A | 9/1999 | Hansen et al. |
| 5,951,530 A | 9/1999 | Steengaard et al. |
| 5,957,889 A | 9/1999 | Poulsen et al. |
| 5,957,890 A | 9/1999 | Mann et al. |
| 5,961,492 A | 10/1999 | Kriesel et al. |
| 5,965,848 A | 10/1999 | Altschul et al. |
| 5,971,941 A | 10/1999 | Simons et al. |
| 5,984,894 A | 11/1999 | Poulsen et al. |
| 5,984,897 A | 11/1999 | Petersen et al. |
| 5,993,423 A | 11/1999 | Choi |
| 5,997,475 A | 12/1999 | Bortz |
| 5,997,501 A | 12/1999 | Gross et al. |
| 6,003,736 A | 12/1999 | Ljunggren |
| 6,005,151 A | 12/1999 | Herrmann et al. |
| 6,010,485 A | 1/2000 | Buch-Rasmussen et al. |
| 6,017,318 A | 1/2000 | Gauthier et al. |
| 6,019,747 A | 2/2000 | Mcphee |
| 6,023,251 A | 2/2000 | Koo et al. |
| 6,024,539 A | 2/2000 | Blomquist |
| 6,027,826 A | 2/2000 | Derochemont et al. |
| 6,028,568 A | 2/2000 | Asakura et al. |
| 6,031,445 A | 2/2000 | Marty et al. |
| 6,032,059 A | 2/2000 | Henning et al. |
| 6,032,119 A | 2/2000 | Brown et al. |
| 6,033,377 A | 3/2000 | Rasmussen et al. |
| 6,036,924 A | 3/2000 | Simons et al. |
| 6,040,578 A | 3/2000 | Malin et al. |
| 6,040,805 A | 3/2000 | Huynh et al. |
| 6,045,537 A | 4/2000 | Klitmose |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| D424,036 S | 5/2000 | Arora et al. |
| 6,056,728 A | 5/2000 | Von Schuckmann |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,074,372 A | 6/2000 | Hansen |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,110,149 A | 8/2000 | Klitgaard et al. |

(56) References Cited

U.S. PATENT DOCUMENTS

| | | |
|---|---|---|
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | De et al. |
| 6,154,176 A | 11/2000 | Fathy et al. |
| 6,156,014 A | 12/2000 | Petersen et al. |
| 6,157,041 A | 12/2000 | Thomas et al. |
| 6,161,028 A | 12/2000 | Braig et al. |
| 6,162,639 A | 12/2000 | Douglas |
| 6,171,276 B1 | 1/2001 | Lippe et al. |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,231,540 B1 | 5/2001 | Smedegaard |
| 6,244,776 B1 | 6/2001 | Wiley |
| 6,248,067 B1 | 6/2001 | Causey et al. |
| 6,248,090 B1 | 6/2001 | Jensen et al. |
| 6,248,093 B1 | 6/2001 | Moberg |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,277,098 B1 | 8/2001 | Klitmose et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,302,855 B1 | 10/2001 | Lav et al. |
| 6,302,869 B1 | 10/2001 | Klitgaard |
| 6,309,370 B1 | 10/2001 | Ben-Haim et al. |
| 6,312,888 B1 | 11/2001 | Wong et al. |
| 6,320,547 B1 | 11/2001 | Fathy et al. |
| 6,323,549 B1 | 11/2001 | Derochemont et al. |
| 6,334,851 B1 | 1/2002 | Hayes et al. |
| 6,354,996 B1 | 3/2002 | Drinan et al. |
| 6,363,609 B1 | 4/2002 | Pickren |
| 6,368,314 B1 | 4/2002 | Kipfer et al. |
| 6,375,627 B1 | 4/2002 | Mauze et al. |
| 6,375,638 B2 | 4/2002 | Nason et al. |
| 6,379,301 B1 | 4/2002 | Worthington et al. |
| 6,379,339 B1 | 4/2002 | Klitgaard et al. |
| 6,381,496 B1 | 4/2002 | Meadows et al. |
| 6,402,689 B1 | 6/2002 | Scarantino et al. |
| 6,404,098 B1 | 6/2002 | Kayama et al. |
| D460,053 S | 7/2002 | Choi |
| 6,413,244 B1 | 7/2002 | Bestetti et al. |
| 6,427,088 B1 | 7/2002 | Bowman et al. |
| D461,241 S | 8/2002 | Moberg et al. |
| D461,891 S | 8/2002 | Moberg |
| 6,436,072 B1 | 8/2002 | Kullas et al. |
| 6,461,331 B1 | 10/2002 | Van Antwerp |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| D469,107 S | 1/2003 | Miller et al. |
| 6,508,788 B2 | 1/2003 | Preuthun |
| 6,512,937 B2 | 1/2003 | Blank et al. |
| 6,520,936 B1 | 2/2003 | Mann |
| 6,524,280 B2 | 2/2003 | Hansen et al. |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,533,183 B2 | 3/2003 | Aasmul et al. |
| 6,537,249 B2 | 3/2003 | Kriesell et al. |
| 6,537,251 B2 | 3/2003 | Klitmose |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,544,229 B1 | 4/2003 | Danby et al. |
| 6,546,268 B1 | 4/2003 | Ishikawa et al. |
| 6,546,269 B1 | 4/2003 | Kurnik |
| 6,547,764 B2 | 4/2003 | Larsen et al. |
| 6,551,276 B1 | 4/2003 | Mann et al. |
| 6,552,693 B1 | 4/2003 | Leisten |
| 6,553,841 B1 | 4/2003 | Blouch |
| 6,554,798 B1 | 4/2003 | Mann et al. |
| 6,554,800 B1 | 4/2003 | Nezhadian et al. |
| 6,556,850 B1 | 4/2003 | Braig et al. |
| D474,778 S | 5/2003 | Barnes |
| 6,558,320 B1 | 5/2003 | Causey et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,011 B1 | 5/2003 | Buch-Rasmussen et al. |
| 6,562,014 B2 | 5/2003 | Lin et al. |
| 6,564,105 B2 | 5/2003 | Starkweather et al. |
| 6,569,115 B1 | 5/2003 | Barker et al. |
| 6,569,125 B2 | 5/2003 | Jepson et al. |
| 6,569,126 B1 | 5/2003 | Poulsen et al. |
| 6,571,128 B2 | 5/2003 | Lebel et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,577,899 B2 | 6/2003 | Lebel et al. |
| 6,580,934 B1 | 6/2003 | Braig et al. |
| 6,582,404 B1 | 6/2003 | Klitgaard et al. |
| 6,583,699 B2 | 6/2003 | Yokoyama |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,595,956 B1 | 7/2003 | Gross et al. |
| 6,605,067 B1 | 8/2003 | Larsen |
| 6,611,419 B1 | 8/2003 | Chakravorty |
| 6,613,019 B2 | 9/2003 | Munk |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,641,533 B2 | 11/2003 | Causey et al. |
| 6,642,908 B2 | 11/2003 | Pleva et al. |
| 6,645,142 B2 | 11/2003 | Braig et al. |
| 6,648,821 B2 | 11/2003 | Lebel et al. |
| 6,650,303 B2 | 11/2003 | Kim et al. |
| 6,650,951 B1 | 11/2003 | Jones et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,662,030 B2 | 12/2003 | Khalil et al. |
| 6,663,602 B2 | 12/2003 | Moeller |
| 6,668,196 B1 | 12/2003 | Villegas et al. |

(56) References Cited

U.S. PATENT DOCUMENTS

| | | |
|---|---|---|
| 6,669,663 B1 | 12/2003 | Thompson |
| 6,669,669 B2 | 12/2003 | Flaherty et al. |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,687,546 B2 | 2/2004 | Lebel et al. |
| 6,690,192 B1 | 2/2004 | Wing |
| 6,690,336 B1 | 2/2004 | Leisten et al. |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,702,779 B2 | 3/2004 | Connelly et al. |
| 6,715,516 B2 | 4/2004 | Ohms et al. |
| 6,716,198 B2 | 4/2004 | Larsen |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,446 B2 | 5/2004 | Lebel et al. |
| 6,733,890 B2 | 5/2004 | Imanaka et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,744,350 B2 | 6/2004 | Blomquist |
| 6,749,587 B2 | 6/2004 | Flaherty |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,752,787 B1 | 6/2004 | Causey et al. |
| 6,753,745 B2 | 6/2004 | Killen et al. |
| 6,753,814 B2 | 6/2004 | Killen et al. |
| 6,758,810 B2 | 7/2004 | Lebel et al. |
| 6,758,835 B2 | 7/2004 | Close et al. |
| 6,762,237 B2 | 7/2004 | Glatkowski et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,787,181 B2 | 9/2004 | Uchiyama et al. |
| 6,791,496 B1 | 9/2004 | Killen et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,826,031 B2 | 11/2004 | Nagai et al. |
| 6,827,702 B2 | 12/2004 | Lebel et al. |
| 6,830,558 B2 | 12/2004 | Flaherty et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,852,104 B2 | 2/2005 | Blomquist |
| 6,853,288 B2 | 2/2005 | Ahn et al. |
| 6,854,620 B2 | 2/2005 | Ramey |
| 6,854,653 B2 | 2/2005 | Eilersen |
| 6,855,129 B2 | 2/2005 | Jensen et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,878,871 B2 | 4/2005 | Scher et al. |
| 6,883,778 B1 | 4/2005 | Newton et al. |
| 6,890,291 B2 | 5/2005 | Robinson et al. |
| 6,893,415 B2 | 5/2005 | Madsen et al. |
| 6,899,695 B2 | 5/2005 | Herrera |
| 6,899,699 B2 | 5/2005 | Enggaard |
| 6,905,989 B2 | 6/2005 | Ellis et al. |
| 6,906,674 B2 | 6/2005 | Mckinzie et al. |
| 6,914,566 B2 | 7/2005 | Beard |
| 6,919,119 B2 | 7/2005 | Kalkan et al. |
| 6,922,590 B1 | 7/2005 | Whitehurst |
| 6,928,298 B2 | 8/2005 | Furutani et al. |
| 6,936,006 B2 | 8/2005 | Sabra |
| 6,936,029 B2 | 8/2005 | Mann et al. |
| 6,943,430 B2 | 9/2005 | Kwon |
| 6,943,731 B2 | 9/2005 | Killen et al. |
| 6,945,961 B2 | 9/2005 | Miller et al. |
| 6,948,918 B2 | 9/2005 | Hansen |
| 6,949,081 B1 | 9/2005 | Chance |
| 6,950,708 B2 | 9/2005 | Bowman et al. |
| 6,956,572 B2 | 10/2005 | Zaleski |
| 6,958,809 B2 | 10/2005 | Sterling et al. |
| 6,960,192 B1 | 11/2005 | Flaherty et al. |
| 6,963,259 B2 | 11/2005 | Killen et al. |
| 6,979,326 B2 | 12/2005 | Mann et al. |
| 6,989,891 B2 | 1/2006 | Braig et al. |
| 6,990,366 B2 | 1/2006 | Say et al. |
| 6,997,911 B2 | 2/2006 | Klitmose |
| 6,997,920 B2 | 2/2006 | Mann et al. |
| 7,002,436 B2 | 2/2006 | Ma et al. |
| 7,005,078 B2 | 2/2006 | Van et al. |
| 7,008,399 B2 | 3/2006 | Larsen et al. |
| 7,008,404 B2 | 3/2006 | Nakajima |
| 7,009,180 B2 | 3/2006 | Sterling et al. |
| 7,014,625 B2 | 3/2006 | Bengtsson |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,029,455 B2 | 4/2006 | Flaherty |
| 7,043,288 B2 | 5/2006 | Davis et al. |
| 7,047,637 B2 | 5/2006 | Derochemont et al. |
| 7,054,836 B2 | 5/2006 | Christensen et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,096,431 B2 | 8/2006 | Tambata et al. |
| 7,104,972 B2 | 9/2006 | Moller et al. |
| 7,109,878 B2 | 9/2006 | Mann et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,133,329 B2 | 11/2006 | Skyggebjerg et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,230,316 B2 | 6/2007 | Yamazaki et al. |
| 7,232,423 B2 | 6/2007 | Mernoee |
| D545,837 S | 7/2007 | Haldimann et al. |
| 7,241,265 B2 | 7/2007 | Cummings et al. |
| 7,248,912 B2 | 7/2007 | Gough et al. |
| D550,227 S | 9/2007 | Sato et al. |
| 7,267,665 B2 | 9/2007 | Steil et al. |
| 7,271,912 B2 | 9/2007 | Sterling et al. |
| D553,625 S | 10/2007 | Burns et al. |
| D554,140 S | 10/2007 | Armendariz |

(56) References Cited

U.S. PATENT DOCUMENTS

| | | |
|---|---|---|
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,343,197 B2 | 3/2008 | Shusterman |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | De Rochemont |
| 7,429,255 B2 | 9/2008 | Thompson |
| 7,454,359 B2 | 11/2008 | Rosenfeld et al. |
| 7,460,130 B2 | 12/2008 | Salganicoff |
| 7,479,949 B2 | 1/2009 | Jobs et al. |
| 7,481,787 B2 | 1/2009 | Gable et al. |
| 7,491,187 B2 | 2/2009 | Van et al. |
| 7,500,949 B2 | 3/2009 | Gottlieb et al. |
| 7,509,156 B2 | 3/2009 | Flanders |
| D590,415 S | 4/2009 | Ball et al. |
| 7,522,124 B2 | 4/2009 | Smith et al. |
| D592,223 S | 5/2009 | Neuhaus |
| 7,534,226 B2 | 5/2009 | Mernoe et al. |
| 7,547,281 B2 | 6/2009 | Hayes et al. |
| 7,553,281 B2 | 6/2009 | Hellwig et al. |
| 7,553,512 B2 | 6/2009 | Kodas et al. |
| 7,555,727 B2 | 6/2009 | Hawkins et al. |
| 7,564,887 B2 | 7/2009 | Wang et al. |
| 7,569,030 B2 | 8/2009 | Lebel et al. |
| 7,570,980 B2 | 8/2009 | Ginsberg |
| D600,341 S | 9/2009 | Loerwald |
| 7,595,623 B2 | 9/2009 | Bennett |
| 7,608,042 B2 | 10/2009 | Goldberger et al. |
| D603,421 S | 11/2009 | Ebeling et al. |
| D607,099 S | 12/2009 | Loerwald |
| 7,647,237 B2 | 1/2010 | Malave et al. |
| 7,651,845 B2 | 1/2010 | Doyle et al. |
| 7,652,901 B2 | 1/2010 | Kirchmeier et al. |
| 7,680,529 B2 | 3/2010 | Kroll |
| D614,587 S | 4/2010 | Yodfat et al. |
| D614,634 S | 4/2010 | Nilsen |
| 7,695,434 B2 | 4/2010 | Malecha |
| 7,708,717 B2 | 5/2010 | Estes et al. |
| 7,714,794 B2 | 5/2010 | Tavassoli Hozouri |
| 7,717,903 B2 | 5/2010 | Estes et al. |
| 7,734,323 B2 | 6/2010 | Blomquist et al. |
| 7,751,907 B2 | 7/2010 | Blomquist |
| 7,763,917 B2 | 7/2010 | De Rochemont |
| 7,766,829 B2 | 8/2010 | Sloan et al. |
| 7,771,391 B2 | 8/2010 | Carter |
| 7,785,258 B2 | 8/2010 | Braig et al. |
| D623,753 S | 9/2010 | Saffer et al. |
| 7,789,859 B2 | 9/2010 | Estes et al. |
| 7,806,854 B2 | 10/2010 | Damiano et al. |
| 7,806,886 B2 | 10/2010 | Kanderian et al. |
| 7,812,774 B2 | 10/2010 | Friman et al. |
| D628,107 S | 11/2010 | Lee |
| 7,828,528 B2 | 11/2010 | Estes et al. |
| 7,837,647 B2 | 11/2010 | Estes et al. |
| 7,850,641 B2 | 12/2010 | Lebel et al. |
| 7,871,376 B2 | 1/2011 | Brown |
| D632,699 S | 2/2011 | Judy et al. |
| 7,878,975 B2 | 2/2011 | Liljeryd et al. |
| 7,887,512 B2 | 2/2011 | Estes et al. |
| 7,918,825 B2 | 4/2011 | O'Connor et al. |
| 7,931,613 B2 | 4/2011 | Haueter et al. |
| 7,938,797 B2 | 5/2011 | Estes |
| 7,946,985 B2 | 5/2011 | Mastrototaro et al. |
| D640,269 S | 6/2011 | Chen |
| 7,956,845 B2 | 6/2011 | Lee |
| D642,191 S | 7/2011 | Barnett et al. |
| 7,972,296 B2 | 7/2011 | Braig et al. |
| D644,242 S | 8/2011 | Matas |
| D644,243 S | 8/2011 | Matas |
| 8,012,119 B2 | 9/2011 | Estes et al. |
| D648,804 S | 11/2011 | Coulter |
| 8,066,805 B2 | 11/2011 | Zuercher et al. |
| 8,069,690 B2 | 12/2011 | Desantolo et al. |
| D652,426 S | 1/2012 | Anzures |
| 8,114,489 B2 | 2/2012 | Nemat-Nasser et al. |
| 8,132,101 B2 | 3/2012 | Buck et al. |
| D656,950 S | 4/2012 | Shallcross et al. |
| 8,156,070 B2 | 4/2012 | Buck et al. |
| D660,315 S | 5/2012 | Anzures |
| 8,178,457 B2 | 5/2012 | De Rochemont |
| D661,701 S | 6/2012 | Brown et al. |
| 8,193,873 B2 | 6/2012 | Kato et al. |
| 8,202,249 B2 | 6/2012 | Iio et al. |
| 8,217,946 B2 | 7/2012 | Halpern et al. |
| 8,219,222 B2 | 7/2012 | Blomquist |
| 8,221,345 B2 | 7/2012 | Blomquist |
| 8,221,359 B2 | 7/2012 | Kristensen et al. |
| 8,231,562 B2 | 7/2012 | Buck et al. |
| D665,409 S | 8/2012 | Gupta et al. |
| 8,237,715 B2 | 8/2012 | Buck et al. |
| 8,250,483 B2 | 8/2012 | Blomquist |
| 8,251,907 B2 | 8/2012 | Sterling et al. |
| 8,257,652 B2 | 9/2012 | Drucker et al. |
| 8,257,653 B2 | 9/2012 | Drucker et al. |
| 8,262,616 B2 | 9/2012 | Grant et al. |
| 8,267,921 B2 | 9/2012 | Yodfat et al. |
| 8,273,296 B2 | 9/2012 | Drucker et al. |
| D669,165 S | 10/2012 | Estes et al. |
| D669,166 S | 10/2012 | Estes et al. |
| D669,167 S | 10/2012 | Estes et al. |
| 8,279,226 B2 | 10/2012 | Krieftewirth |
| 8,310,415 B2 | 11/2012 | Mclaughlin et al. |
| 8,337,469 B2 | 12/2012 | Eberhart et al. |
| D674,405 S | 1/2013 | Guastella et al. |
| 8,350,657 B2 | 1/2013 | Derochemont |
| 8,354,294 B2 | 1/2013 | De et al. |
| 8,357,091 B2 | 1/2013 | Say et al. |
| 8,365,065 B2 | 1/2013 | Gejdos et al. |
| 8,372,005 B2 | 2/2013 | Say et al. |
| D677,685 S | 3/2013 | Simmons et al. |
| D682,289 S | 5/2013 | Dijulio et al. |
| D682,304 S | 5/2013 | Mierau et al. |
| D682,305 S | 5/2013 | Mierau et al. |
| 8,439,834 B2 | 5/2013 | Schmelzeisen-Redeker et al. |
| 8,449,524 B2 | 5/2013 | Braig et al. |
| 8,452,359 B2 | 5/2013 | Rebec et al. |
| D683,738 S | 6/2013 | Wujcik et al. |
| 8,454,576 B2 | 6/2013 | Mastrototaro et al. |
| 8,467,980 B2 | 6/2013 | Campbell et al. |
| D687,062 S | 7/2013 | Gardner et al. |
| 8,478,557 B2 | 7/2013 | Hayter et al. |
| D687,541 S | 8/2013 | Estes et al. |
| D688,686 S | 8/2013 | Rhee et al. |
| 8,514,086 B2 | 8/2013 | Harper et al. |
| D689,087 S | 9/2013 | Fymat |
| D689,089 S | 9/2013 | Impas et al. |
| D689,090 S | 9/2013 | Impas et al. |
| D689,523 S | 9/2013 | Galbraith et al. |
| D689,874 S | 9/2013 | Brinda et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| D690,717 S | 10/2013 | Thomsen et al. |
| D690,718 S | 10/2013 | Thomsen et al. |
| D691,258 S | 10/2013 | Estes et al. |
| D691,259 S | 10/2013 | Estes et al. |
| 8,547,239 B2 | 10/2013 | Peatfield et al. |
| D693,114 S | 11/2013 | Lemanski, Sr. |
| D693,365 S | 11/2013 | Gardner et al. |
| D693,837 S | 11/2013 | Bouchier |
| D694,262 S | 11/2013 | Jang et al. |
| 8,579,815 B2 | 11/2013 | Galley et al. |
| 8,593,819 B2 | 11/2013 | De Rochemont |
| D695,757 S | 12/2013 | Ray et al. |
| 8,597,274 B2 | 12/2013 | Sloan et al. |
| 8,601,005 B2 | 12/2013 | Bousamra et al. |
| 8,615,366 B2 | 12/2013 | Galley et al. |

(56) References Cited

U.S. PATENT DOCUMENTS

| | | |
|---|---|---|
| D697,204 S | 1/2014 | Maier et al. |
| D697,519 S | 1/2014 | Thomsen et al. |
| 8,622,906 B2 | 1/2014 | Say et al. |
| 8,622,988 B2 | 1/2014 | Hayter |
| D698,808 S | 2/2014 | Funabashi et al. |
| D699,741 S | 2/2014 | Wantland et al. |
| 8,657,779 B2 | 2/2014 | Blomquist |
| D701,879 S | 4/2014 | Foit et al. |
| D702,258 S | 4/2014 | Wantland et al. |
| D705,261 S | 5/2014 | Holz et al. |
| 8,715,839 B2 | 5/2014 | De Rochemont |
| 8,719,945 B2 | 5/2014 | Birtwhistle et al. |
| 8,743,662 B2 | 6/2014 | Sjolund et al. |
| 8,756,074 B2 | 6/2014 | Brzustowicz |
| 8,761,940 B2 | 6/2014 | Long et al. |
| D709,080 S | 7/2014 | Kim |
| D709,183 S | 7/2014 | Kemlein |
| D709,917 S | 7/2014 | Faulkner et al. |
| 8,774,887 B2 | 7/2014 | Say et al. |
| D710,879 S | 8/2014 | Elston et al. |
| 8,810,394 B2 | 8/2014 | Kalpin |
| 8,816,862 B2 | 8/2014 | Harper et al. |
| 8,839,106 B2 | 9/2014 | Lee et al. |
| D714,816 S | 10/2014 | Varon |
| D714,822 S | 10/2014 | Capua et al. |
| D715,315 S | 10/2014 | Wood |
| D715,815 S | 10/2014 | Bortman et al. |
| D715,835 S | 10/2014 | Montgomery et al. |
| D716,340 S | 10/2014 | Bresin et al. |
| D717,822 S | 11/2014 | Brotman et al. |
| D717,823 S | 11/2014 | Brotman et al. |
| D717,830 S | 11/2014 | Brinda et al. |
| D718,438 S | 11/2014 | Davis et al. |
| 8,895,315 B2 | 11/2014 | Batman et al. |
| D718,779 S | 12/2014 | Hang et al. |
| D719,186 S | 12/2014 | Kim |
| D720,366 S | 12/2014 | Hiltunen et al. |
| D720,765 S | 1/2015 | Xie et al. |
| 8,929,823 B2 | 1/2015 | Mears et al. |
| 8,939,935 B2 | 1/2015 | O'Connor et al. |
| 8,961,465 B2 | 2/2015 | Blomquist |
| D724,616 S | 3/2015 | Jou |
| 8,992,464 B2 | 3/2015 | Bashan et al. |
| D726,760 S | 4/2015 | Yokota et al. |
| D727,336 S | 4/2015 | Allison et al. |
| D727,928 S | 4/2015 | Allison et al. |
| 9,008,803 B2 | 4/2015 | Blomquist |
| D730,378 S | 5/2015 | Xiong et al. |
| 9,022,996 B2 | 5/2015 | Eberhart et al. |
| 9,033,877 B2 | 5/2015 | Werner et al. |
| 9,041,730 B2 | 5/2015 | Johnson et al. |
| D730,929 S | 6/2015 | Yu et al. |
| D731,525 S | 6/2015 | Myers |
| D733,175 S | 6/2015 | Bae |
| D733,179 S | 6/2015 | Kwon |
| 9,050,409 B2 | 6/2015 | Haueter et al. |
| 9,056,165 B2 | 6/2015 | Steil et al. |
| 9,061,097 B2 | 6/2015 | Holt et al. |
| D734,356 S | 7/2015 | Xiong et al. |
| 9,072,477 B2 | 7/2015 | Say et al. |
| 9,076,107 B2 | 7/2015 | Cameron et al. |
| D736,792 S | 8/2015 | Brinda et al. |
| D736,811 S | 8/2015 | Teichner et al. |
| D737,278 S | 8/2015 | Shin et al. |
| D737,305 S | 8/2015 | Scazafavo et al. |
| D737,831 S | 9/2015 | Lee |
| D737,832 S | 9/2015 | Lim et al. |
| D738,901 S | 9/2015 | Amin |
| D738,907 S | 9/2015 | Cabrera-Cordon et al. |
| D738,913 S | 9/2015 | Cabrera-Cordon et al. |
| D738,914 S | 9/2015 | Torres et al. |
| D739,878 S | 9/2015 | Baxley |
| 9,134,823 B2 | 9/2015 | Grant et al. |
| 9,136,939 B2 | 9/2015 | Galley et al. |
| 9,144,204 B2 | 9/2015 | Redmond et al. |
| D740,301 S | 10/2015 | Soegiono et al. |
| D740,308 S | 10/2015 | Kim et al. |
| D740,311 S | 10/2015 | Drozd et al. |
| D741,354 S | 10/2015 | Lee et al. |
| D741,359 S | 10/2015 | Ji-Hye et al. |
| D741,891 S | 10/2015 | Gardner et al. |
| 9,159,148 B2 | 10/2015 | Boyer et al. |
| 9,171,343 B1 | 10/2015 | Fischell et al. |
| D743,431 S | 11/2015 | Pal et al. |
| D743,435 S | 11/2015 | Herold et al. |
| D743,991 S | 11/2015 | Pal et al. |
| 9,180,224 B2 | 11/2015 | Moseley et al. |
| 9,180,244 B2 | 11/2015 | Anderson et al. |
| 9,186,113 B2 | 11/2015 | Harper et al. |
| 9,192,716 B2 | 11/2015 | Jugl et al. |
| D744,505 S | 12/2015 | Wilberding et al. |
| D744,514 S | 12/2015 | Shin et al. |
| D744,517 S | 12/2015 | Pal et al. |
| D745,032 S | 12/2015 | Pal et al. |
| D745,034 S | 12/2015 | Pal et al. |
| D745,035 S | 12/2015 | Pal et al. |
| D745,050 S | 12/2015 | Kwon |
| D745,543 S | 12/2015 | Kim et al. |
| D746,314 S | 12/2015 | Jung et al. |
| 9,198,623 B2 | 12/2015 | Fern et al. |
| D746,827 S | 1/2016 | Jung et al. |
| D746,828 S | 1/2016 | Arai et al. |
| D746,848 S | 1/2016 | Bovet et al. |
| D747,352 S | 1/2016 | Lee et al. |
| 9,233,204 B2 | 1/2016 | Booth et al. |
| D748,646 S | 2/2016 | Kim et al. |
| D749,097 S | 2/2016 | Zou et al. |
| D749,118 S | 2/2016 | Wang |
| D750,663 S | 3/2016 | Mariet et al. |
| D751,081 S | 3/2016 | Kim et al. |
| D751,090 S | 3/2016 | Hu et al. |
| D751,100 S | 3/2016 | Lindn et al. |
| D751,585 S | 3/2016 | Kaufthal et al. |
| D751,586 S | 3/2016 | Kaufthal et al. |
| D752,604 S | 3/2016 | Zhang |
| D752,736 S | 3/2016 | Chandrasenan et al. |
| D753,134 S | 4/2016 | Vazquez |
| D753,139 S | 4/2016 | Bovet |
| D753,177 S | 4/2016 | Mierau et al. |
| D753,685 S | 4/2016 | Zimmerman et al. |
| D754,150 S | 4/2016 | Oh et al. |
| D754,670 S | 4/2016 | Park |
| D754,685 S | 4/2016 | Carlton et al. |
| D754,689 S | 4/2016 | Lee |
| D754,713 S | 4/2016 | Zhang et al. |
| D754,714 S | 4/2016 | Zhang et al. |
| D754,718 S | 4/2016 | Zhou |
| D755,193 S | 5/2016 | Sun et al. |
| D755,206 S | 5/2016 | Lee et al. |
| D755,799 S | 5/2016 | Finnis et al. |
| D755,820 S | 5/2016 | Wang |
| D755,830 S | 5/2016 | Chaudhri et al. |
| D756,387 S | 5/2016 | Chang et al. |
| D757,026 S | 5/2016 | Lim et al. |
| D757,032 S | 5/2016 | Sabia et al. |
| D757,035 S | 5/2016 | Raskin et al. |
| D757,047 S | 5/2016 | Cornwell et al. |
| D758,391 S | 6/2016 | Suarez |
| D758,422 S | 6/2016 | Zhao |
| D758,433 S | 6/2016 | Lee et al. |
| D759,032 S | 6/2016 | Amin et al. |
| D759,078 S | 6/2016 | Iwamoto |
| D759,678 S | 6/2016 | Jung et al. |
| D759,687 S | 6/2016 | Chang et al. |
| D760,752 S | 7/2016 | Anzures et al. |
| D761,812 S | 7/2016 | Motamedi |
| D761,843 S | 7/2016 | Kim |
| D762,234 S | 7/2016 | Li et al. |
| D762,675 S | 8/2016 | Lim et al. |
| D763,285 S | 8/2016 | Chan et al. |
| D763,308 S | 8/2016 | Wang et al. |
| D763,860 S | 8/2016 | Sunshine et al. |
| D763,868 S | 8/2016 | Lee et al. |
| D763,921 S | 8/2016 | Dharwada et al. |

(56) References Cited

U.S. PATENT DOCUMENTS

| | | |
|---|---|---|
| D765,092 S | 8/2016 | Chaudhri et al. |
| D765,110 S | 8/2016 | Liang |
| D765,124 S | 8/2016 | Minks-Brown et al. |
| 9,402,950 B2 | 8/2016 | Dilanni et al. |
| D765,707 S | 9/2016 | Gomez |
| D765,710 S | 9/2016 | Anzures et al. |
| D766,257 S | 9/2016 | Zhang et al. |
| D766,286 S | 9/2016 | Lee et al. |
| D766,424 S | 9/2016 | Anderson et al. |
| D767,586 S | 9/2016 | Kwon et al. |
| D768,144 S | 10/2016 | Kim et al. |
| D768,154 S | 10/2016 | Kim et al. |
| D768,188 S | 10/2016 | Li et al. |
| D768,660 S | 10/2016 | Wielgosz |
| D768,685 S | 10/2016 | Lee et al. |
| D768,687 S | 10/2016 | Bae et al. |
| D769,314 S | 10/2016 | Piroddi et al. |
| D769,315 S | 10/2016 | Scotti |
| D769,322 S | 10/2016 | Rajeswaran et al. |
| D769,325 S | 10/2016 | Casalegno et al. |
| D770,507 S | 11/2016 | Umezawa et al. |
| D770,515 S | 11/2016 | Cho et al. |
| D771,073 S | 11/2016 | Choi et al. |
| D771,076 S | 11/2016 | Butcher et al. |
| D771,672 S | 11/2016 | Tanabe et al. |
| D771,690 S | 11/2016 | Yin et al. |
| D772,241 S | 11/2016 | Capano |
| D772,911 S | 11/2016 | Lee et al. |
| D772,924 S | 11/2016 | Begin et al. |
| 9,486,571 B2 | 11/2016 | Rosinko |
| D773,510 S | 12/2016 | Foss et al. |
| D773,531 S | 12/2016 | Toth et al. |
| D775,184 S | 12/2016 | Song et al. |
| D775,196 S | 12/2016 | Huang et al. |
| 9,520,649 B2 | 12/2016 | De Rochemont |
| D775,658 S | 1/2017 | Luo et al. |
| D776,126 S | 1/2017 | Lai et al. |
| D776,137 S | 1/2017 | Chaudhri et al. |
| D776,253 S | 1/2017 | Li |
| D776,687 S | 1/2017 | Wick et al. |
| D776,702 S | 1/2017 | Huang et al. |
| D777,191 S | 1/2017 | Polimeni |
| D777,200 S | 1/2017 | Luo et al. |
| D777,204 S | 1/2017 | Lee et al. |
| D777,735 S | 1/2017 | Kim et al. |
| D777,758 S | 1/2017 | Kisselev et al. |
| D777,906 S | 1/2017 | Anderson et al. |
| 9,579,456 B2 | 2/2017 | Budiman et al. |
| D781,305 S | 3/2017 | Lau |
| D781,323 S | 3/2017 | Green et al. |
| D781,781 S | 3/2017 | Schimmoeller, Jr. |
| D781,877 S | 3/2017 | Ko et al. |
| D781,878 S | 3/2017 | Butcher et al. |
| D781,879 S | 3/2017 | Butcher et al. |
| D781,903 S | 3/2017 | Reichle et al. |
| D781,905 S | 3/2017 | Nakaguchi et al. |
| D781,908 S | 3/2017 | Bhandari et al. |
| D782,506 S | 3/2017 | Kim et al. |
| D783,652 S | 4/2017 | Guan et al. |
| D783,672 S | 4/2017 | Rajasankar et al. |
| D784,372 S | 4/2017 | Kovchiy |
| D785,010 S | 4/2017 | Bachman et al. |
| D785,656 S | 5/2017 | Bramer et al. |
| D786,266 S | 5/2017 | Van et al. |
| D786,270 S | 5/2017 | Barry et al. |
| D786,278 S | 5/2017 | Motamedi |
| D786,898 S | 5/2017 | Hall |
| D788,126 S | 5/2017 | Evnin et al. |
| D788,138 S | 5/2017 | Lee et al. |
| D788,140 S | 5/2017 | Hemsley et al. |
| D788,145 S | 5/2017 | Sullivan et al. |
| 9,656,017 B2 | 5/2017 | Greene |
| D788,621 S | 6/2017 | Shallice et al. |
| D788,652 S | 6/2017 | Mutsuro et al. |
| D788,808 S | 6/2017 | Chaudhri et al. |
| D789,402 S | 6/2017 | Dye et al. |
| D789,419 S | 6/2017 | Chaudhri et al. |
| D789,967 S | 6/2017 | Kaplan et al. |
| D789,982 S | 6/2017 | Christiana et al. |
| D790,560 S | 6/2017 | Inose et al. |
| D790,562 S | 6/2017 | Nageli et al. |
| D790,583 S | 6/2017 | Kay et al. |
| D791,781 S | 7/2017 | Donarski et al. |
| D791,805 S | 7/2017 | Segars |
| D791,806 S | 7/2017 | Brewington et al. |
| D791,812 S | 7/2017 | Bistoni et al. |
| 9,707,336 B2 | 7/2017 | Dang et al. |
| D793,412 S | 8/2017 | Chaudhri et al. |
| D794,649 S | 8/2017 | Niijima et al. |
| D795,284 S | 8/2017 | Miller et al. |
| D795,294 S | 8/2017 | Faulkner et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,717,849 B2 | 8/2017 | Mhatre et al. |
| 9,743,224 B2 | 8/2017 | San et al. |
| D796,530 S | 9/2017 | Mcmillan et al. |
| D796,540 S | 9/2017 | Mclean et al. |
| D797,116 S | 9/2017 | Chapman et al. |
| D797,123 S | 9/2017 | Lee et al. |
| D797,763 S | 9/2017 | Kim et al. |
| D797,771 S | 9/2017 | Caporal et al. |
| D797,772 S | 9/2017 | Mizono et al. |
| D797,774 S | 9/2017 | Park et al. |
| D797,788 S | 9/2017 | Havranek, Jr. |
| D797,797 S | 9/2017 | Gandhi et al. |
| D798,310 S | 9/2017 | Golden et al. |
| D798,311 S | 9/2017 | Golden et al. |
| D798,318 S | 9/2017 | Ferguson et al. |
| D798,895 S | 10/2017 | Kim et al. |
| D799,536 S | 10/2017 | Eder |
| D800,757 S | 10/2017 | Mullen et al. |
| D800,765 S | 10/2017 | Stoksik |
| D800,769 S | 10/2017 | Hennessy et al. |
| D801,383 S | 10/2017 | Park et al. |
| D801,519 S | 10/2017 | Sabin et al. |
| D801,990 S | 11/2017 | Reissner et al. |
| D802,011 S | 11/2017 | Friedman et al. |
| D802,088 S | 11/2017 | Bos et al. |
| D802,607 S | 11/2017 | Apodaca et al. |
| D803,232 S | 11/2017 | Leigh et al. |
| D803,242 S | 11/2017 | Mizono et al. |
| D803,850 S | 11/2017 | Chang et al. |
| D804,502 S | 12/2017 | Amini et al. |
| D804,505 S | 12/2017 | Hoffman et al. |
| D804,516 S | 12/2017 | Dye et al. |
| D805,525 S | 12/2017 | Dascola et al. |
| D805,541 S | 12/2017 | Juliano |
| D806,117 S | 12/2017 | Springer |
| D806,716 S | 1/2018 | Pahwa et al. |
| D806,748 S | 1/2018 | Van et al. |
| D806,749 S | 1/2018 | Van et al. |
| D806,750 S | 1/2018 | Van et al. |
| D807,376 S | 1/2018 | Mizono et al. |
| D807,391 S | 1/2018 | Seemakurty et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,417 S | 1/2018 | Mander et al. |
| D808,423 S | 1/2018 | Jiang et al. |
| D808,974 S | 1/2018 | Chiappone et al. |
| D808,983 S | 1/2018 | Narinedhat et al. |
| D809,134 S | 1/2018 | Crothall |
| 9,857,090 B2 | 1/2018 | Golden et al. |
| 9,878,097 B2 | 1/2018 | Estes |
| D809,535 S | 2/2018 | Park et al. |
| D810,095 S | 2/2018 | Vali et al. |
| D810,116 S | 2/2018 | Mclean et al. |
| D810,771 S | 2/2018 | Gandhi et al. |
| D812,072 S | 3/2018 | Hoffman |
| 9,907,515 B2 | 3/2018 | Doyle et al. |

(56) References Cited

U.S. PATENT DOCUMENTS

| | | |
|---|---|---|
| D815,131 S | 4/2018 | Thompson et al. |
| D815,665 S | 4/2018 | Li et al. |
| D816,090 S | 4/2018 | Stonecipher et al. |
| D816,093 S | 4/2018 | Mazur et al. |
| 9,931,454 B2 | 4/2018 | Lo et al. |
| D816,708 S | 5/2018 | Riedel et al. |
| D816,709 S | 5/2018 | Riedel et al. |
| D816,713 S | 5/2018 | Kang |
| D817,339 S | 5/2018 | Nanjappan et al. |
| D818,491 S | 5/2018 | Timmer et al. |
| D819,057 S | 5/2018 | Huang |
| D819,059 S | 5/2018 | O'Toole |
| D819,065 S | 5/2018 | Xie et al. |
| D819,067 S | 5/2018 | Behzadi et al. |
| 9,980,140 B1 | 5/2018 | Spencer et al. |
| 9,984,773 B2 | 5/2018 | Gondhalekar et al. |
| D819,646 S | 6/2018 | Jow et al. |
| D820,304 S | 6/2018 | Coffman et al. |
| D820,311 S | 6/2018 | Cabrera et al. |
| D820,862 S | 6/2018 | Alfonzo et al. |
| D821,437 S | 6/2018 | Chaudhri et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D822,708 S | 7/2018 | Ghosh |
| D823,859 S | 7/2018 | Boyd |
| D823,862 S | 7/2018 | Chung et al. |
| D824,400 S | 7/2018 | Chang et al. |
| D824,951 S | 8/2018 | Kolbrener et al. |
| D826,956 S | 8/2018 | Pillalamarri et al. |
| D826,957 S | 8/2018 | Pillalamarri et al. |
| D826,969 S | 8/2018 | Goyette et al. |
| D828,375 S | 9/2018 | Mok et al. |
| D828,377 S | 9/2018 | Dhide |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,658 S | 12/2018 | Chan et al. |
| D835,659 S | 12/2018 | Anzures et al. |
| D835,666 S | 12/2018 | Saleh et al. |
| D836,123 S | 12/2018 | Pillalamarri et al. |
| D837,807 S | 1/2019 | Baber et al. |
| D837,809 S | 1/2019 | Kagatsume et al. |
| D838,731 S | 1/2019 | Pillalamarri et al. |
| D839,287 S | 1/2019 | Hersh et al. |
| D839,294 S | 1/2019 | Mazlish et al. |
| D840,418 S | 2/2019 | Saad et al. |
| D840,419 S | 2/2019 | Saad et al. |
| D841,660 S | 2/2019 | Mercado |
| D844,022 S | 3/2019 | Amin |
| D845,317 S | 4/2019 | Wellmeier et al. |
| 10,248,839 B2 | 4/2019 | Levy et al. |
| 10,263,802 B2 | 4/2019 | Burns et al. |
| D848,459 S | 5/2019 | Li |
| D851,099 S | 6/2019 | Uppala et al. |
| D851,658 S | 6/2019 | Pillalamarri et al. |
| D852,816 S | 7/2019 | Baekelandt et al. |
| D852,817 S | 7/2019 | Aoshima |
| D852,837 S | 7/2019 | Mazlish et al. |
| D853,441 S | 7/2019 | Khandelwal |
| 10,335,464 B1 | 7/2019 | Michelich et al. |
| D857,724 S | 8/2019 | Clediere et al. |
| D858,566 S | 9/2019 | Bacchus |
| D858,567 S | 9/2019 | Bacchus |
| 10,410,538 B2 | 9/2019 | Simpson et al. |
| D863,343 S | 10/2019 | Mazlish et al. |
| D864,239 S | 10/2019 | Hisada et al. |
| 10,426,896 B2 | 10/2019 | Desborough et al. |
| D865,795 S | 11/2019 | Koo |
| D865,813 S | 11/2019 | Lee et al. |
| D866,584 S | 11/2019 | Burroughs et al. |
| D867,601 S | 11/2019 | Henry et al. |
| D870,767 S | 12/2019 | Villafane |
| D872,746 S | 1/2020 | Laborde |
| D874,471 S | 2/2020 | Pillalamarri et al. |
| D875,111 S | 2/2020 | Clediere |
| D875,114 S | 2/2020 | Clediere |
| D875,124 S | 2/2020 | Yan |
| 10,572,107 B1 | 2/2020 | Beebe et al. |
| D879,118 S | 3/2020 | Chen et al. |
| 10,583,250 B2 | 3/2020 | Mazlish et al. |
| D880,497 S | 4/2020 | Boyd |
| D880,498 S | 4/2020 | Shahidi et al. |
| D883,319 S | 5/2020 | Caro et al. |
| D884,007 S | 5/2020 | Uppala et al. |
| D884,716 S | 5/2020 | Tan et al. |
| D886,850 S | 6/2020 | Kim et al. |
| D888,070 S | 6/2020 | Yusupov et al. |
| D888,748 S | 6/2020 | Valladares et al. |
| D890,206 S | 7/2020 | Felkins et al. |
| 10,737,024 B2 | 8/2020 | Schmid |
| D894,918 S | 9/2020 | Hopper et al. |
| D895,652 S | 9/2020 | Langan et al. |
| 10,773,032 B2 | 9/2020 | Cirillo et al. |
| D904,426 S | 12/2020 | Paul |
| D905,091 S | 12/2020 | Henry et al. |
| 10,871,889 B2 | 12/2020 | Ballantyne et al. |
| 10,904,270 B2 | 1/2021 | Muddu et al. |
| D910,063 S | 2/2021 | Brooks |
| D910,654 S | 2/2021 | Eder |
| D910,669 S | 2/2021 | Lin |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| 10,987,468 B2 | 4/2021 | Mazlish et al. |
| D918,261 S | 5/2021 | Ramamurthy et al. |
| D920,349 S | 5/2021 | Clements et al. |
| D920,351 S | 5/2021 | Zhang |
| D923,033 S | 6/2021 | Smith et al. |
| D927,527 S | 8/2021 | Bragdon et al. |
| D927,533 S | 8/2021 | Clymer |
| D928,199 S | 8/2021 | Mazlish et al. |
| D929,459 S | 8/2021 | Uppala et al. |
| D931,898 S | 9/2021 | Demar |
| D937,312 S | 11/2021 | Ding et al. |
| D938,447 S | 12/2021 | Holland |
| D939,570 S | 12/2021 | Dye et al. |
| 11,197,964 B2 | 12/2021 | Sjolund et al. |
| D940,156 S | 1/2022 | Butcher et al. |
| D944,772 S | 3/2022 | Kim |
| D944,824 S | 3/2022 | Wang et al. |
| 11,260,169 B2 | 3/2022 | Estes |
| D954,078 S | 6/2022 | Rahate et al. |
| 2001/0021803 A1 | 9/2001 | Blank et al. |
| 2001/0034023 A1 | 10/2001 | Stanton et al. |
| 2001/0034502 A1 | 10/2001 | Moberg et al. |
| 2001/0041869 A1 | 11/2001 | Causey et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0091358 A1 | 7/2002 | Klitmose |

(56) References Cited

U.S. PATENT DOCUMENTS

| | | |
|---|---|---|
| 2002/0123740 A1 | 9/2002 | Flaherty et al. |
| 2002/0126036 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0175931 A1 | 11/2002 | Holtz et al. |
| 2002/0177810 A1 | 11/2002 | Reilly et al. |
| 2002/0190818 A1 | 12/2002 | Endou et al. |
| 2003/0023148 A1 | 1/2003 | Lorenz et al. |
| 2003/0023152 A1 | 1/2003 | Abbink et al. |
| 2003/0028089 A1 | 2/2003 | Galley et al. |
| 2003/0034124 A1 | 2/2003 | Sugaya et al. |
| 2003/0040715 A1 | 2/2003 | D'Antonio et al. |
| 2003/0050621 A1 | 3/2003 | Lebel et al. |
| 2003/0055380 A1 | 3/2003 | Flaherty |
| 2003/0060692 A1 | 3/2003 | L. Ruchti et al. |
| 2003/0065308 A1 | 4/2003 | Lebel et al. |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0088238 A1 | 5/2003 | Poulsen et al. |
| 2003/0090649 A1 | 5/2003 | Sterling et al. |
| 2003/0100040 A1 | 5/2003 | Bonnecaze et al. |
| 2003/0122647 A1 | 7/2003 | Ou |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0167035 A1 | 9/2003 | Flaherty et al. |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0198558 A1 | 10/2003 | Nason et al. |
| 2003/0199825 A1 | 10/2003 | Flaherty |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0216683 A1 | 11/2003 | Shekalim |
| 2003/0220605 A1 | 11/2003 | Bowman et al. |
| 2003/0221621 A1 | 12/2003 | Pokharna et al. |
| 2004/0001027 A1 | 1/2004 | Killen et al. |
| 2004/0010207 A1 | 1/2004 | Flaherty et al. |
| 2004/0019325 A1 | 1/2004 | Shekalim |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064096 A1 | 4/2004 | Flaherty et al. |
| 2004/0064259 A1 | 4/2004 | Haaland et al. |
| 2004/0068224 A1 | 4/2004 | Couvillon et al. |
| 2004/0069004 A1 | 4/2004 | Gist et al. |
| 2004/0069044 A1 | 4/2004 | Lavi et al. |
| 2004/0078028 A1 | 4/2004 | Flaherty et al. |
| 2004/0087894 A1 | 5/2004 | Flaherty |
| 2004/0087904 A1 | 5/2004 | Langley et al. |
| 2004/0092865 A1 | 5/2004 | Flaherty et al. |
| 2004/0092878 A1 | 5/2004 | Flaherty |
| 2004/0093331 A1 | 5/2004 | Garner et al. |
| 2004/0097796 A1 | 5/2004 | Berman et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0127844 A1 | 7/2004 | Flaherty |
| 2004/0133166 A1 | 7/2004 | Moberg et al. |
| 2004/0147034 A1 | 7/2004 | Gore et al. |
| 2004/0153032 A1 | 8/2004 | Garribotto et al. |
| 2004/0153257 A1 | 8/2004 | Munk |
| 2004/0171983 A1 | 9/2004 | Sparks et al. |
| 2004/0176727 A1 | 9/2004 | Shekalim |
| 2004/0203357 A1 | 10/2004 | Nassimi |
| 2004/0204673 A1 | 10/2004 | Flaherty |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0220551 A1 | 11/2004 | Flaherty et al. |
| 2004/0235446 A1 | 11/2004 | Flaherty et al. |
| 2004/0241736 A1 | 12/2004 | Hendee et al. |
| 2004/0249308 A1 | 12/2004 | Forssell |
| 2004/0260233 A1 | 12/2004 | Garibotto et al. |
| 2005/0003470 A1 | 1/2005 | Nelson et al. |
| 2005/0020980 A1 | 1/2005 | Inoue et al. |
| 2005/0021005 A1 | 1/2005 | Flaherty et al. |
| 2005/0022274 A1 | 1/2005 | Campbell et al. |
| 2005/0033148 A1 | 2/2005 | Haueter et al. |
| 2005/0038674 A1 | 2/2005 | Braig et al. |
| 2005/0044500 A1 | 2/2005 | Orimoto et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0065760 A1 | 3/2005 | Murtfeldt et al. |
| 2005/0075624 A1 | 4/2005 | Miesel |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0105095 A1 | 5/2005 | Pesach et al. |
| 2005/0114374 A1 | 5/2005 | Juszkiewicz et al. |
| 2005/0134609 A1 | 6/2005 | Yu |
| 2005/0137573 A1 | 6/2005 | Mclaughlin |
| 2005/0160858 A1 | 7/2005 | Mernoe |
| 2005/0171503 A1 | 8/2005 | Van et al. |
| 2005/0171512 A1 | 8/2005 | Flaherty |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0192561 A1 | 9/2005 | Mernoe |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0245878 A1 | 11/2005 | Mernoe et al. |
| 2005/0251097 A1 | 11/2005 | Mernoe |
| 2005/0261660 A1 | 11/2005 | Choi |
| 2005/0262451 A1 | 11/2005 | Remignanti et al. |
| 2005/0267402 A1 | 12/2005 | Stewart et al. |
| 2005/0272640 A1 | 12/2005 | Doyle et al. |
| 2005/0273059 A1 | 12/2005 | Mernoe et al. |
| 2005/0277912 A1 | 12/2005 | John |
| 2006/0009727 A1 | 1/2006 | O'Mahony et al. |
| 2006/0041229 A1 | 2/2006 | Garibotto et al. |
| 2006/0064053 A1 | 3/2006 | Bollish et al. |
| 2006/0069382 A1 | 3/2006 | Pedersen |
| 2006/0074381 A1 | 4/2006 | Malave et al. |
| 2006/0079765 A1 | 4/2006 | Neer et al. |
| 2006/0079809 A1 | 4/2006 | Goldberger et al. |
| 2006/0086994 A1 | 4/2006 | Viefers et al. |
| 2006/0095014 A1 | 5/2006 | Ethelfeld |
| 2006/0100494 A1 | 5/2006 | Kroll |
| 2006/0134323 A1 | 6/2006 | O'Brien |
| 2006/0134491 A1 | 6/2006 | Hilchenko et al. |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0184119 A1 | 8/2006 | Remde et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0200073 A1 | 9/2006 | Radmer et al. |
| 2006/0204535 A1 | 9/2006 | Johnson |
| 2006/0206054 A1 | 9/2006 | Shekalim |
| 2006/0229531 A1 | 10/2006 | Goldberger et al. |
| 2006/0247581 A1 | 11/2006 | Pedersen et al. |
| 2006/0253085 A1 | 11/2006 | Geismar et al. |

(56) References Cited

U.S. PATENT DOCUMENTS

| | | |
|---|---|---|
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0083160 A1 | 4/2007 | Hall et al. |
| 2007/0088271 A1 | 4/2007 | Richards |
| 2007/0100635 A1 | 5/2007 | Mahajan et al. |
| 2007/0106135 A1 | 5/2007 | Sloan et al. |
| 2007/0106218 A1 | 5/2007 | Yodfat et al. |
| 2007/0116601 A1 | 5/2007 | Patton |
| 2007/0118405 A1 | 5/2007 | Campbell et al. |
| 2007/0124002 A1 | 5/2007 | Estes et al. |
| 2007/0129690 A1 | 6/2007 | Rosenblatt et al. |
| 2007/0142720 A1 | 6/2007 | Ridder et al. |
| 2007/0156092 A1 | 7/2007 | Estes et al. |
| 2007/0166453 A1 | 7/2007 | Van et al. |
| 2007/0167905 A1 | 7/2007 | Estes et al. |
| 2007/0167912 A1 | 7/2007 | Causey et al. |
| 2007/0171087 A1 | 7/2007 | Shimazu et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0179444 A1 | 8/2007 | Causey et al. |
| 2007/0191716 A1 | 8/2007 | Goldberger et al. |
| 2007/0197163 A1 | 8/2007 | Robertson |
| 2007/0213657 A1 | 9/2007 | Jennewine et al. |
| 2007/0225675 A1 | 9/2007 | Robinson et al. |
| 2007/0239116 A1 | 10/2007 | Follman et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0033320 A1 | 2/2008 | Racchini et al. |
| 2008/0051716 A1 | 2/2008 | Stutz |
| 2008/0051738 A1 | 2/2008 | Griffin |
| 2008/0051764 A1 | 2/2008 | Dent et al. |
| 2008/0058625 A1 | 3/2008 | Mcgarraugh et al. |
| 2008/0059158 A1 | 3/2008 | Matsuo et al. |
| 2008/0065050 A1 | 3/2008 | Sparks et al. |
| 2008/0071157 A1 | 3/2008 | Mcgarraugh et al. |
| 2008/0071158 A1 | 3/2008 | Mcgarraugh et al. |
| 2008/0078400 A1 | 4/2008 | Martens et al. |
| 2008/0097289 A1 | 4/2008 | Steil et al. |
| 2008/0097381 A1 | 4/2008 | Moberg et al. |
| 2008/0114304 A1 | 5/2008 | Nalesso et al. |
| 2008/0119705 A1 | 5/2008 | Patel et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0201325 A1 | 8/2008 | Doniger et al. |
| 2008/0206067 A1 | 8/2008 | De et al. |
| 2008/0208113 A1 | 8/2008 | Damiano et al. |
| 2008/0208627 A1 | 8/2008 | Skyggebjerg |
| 2008/0214919 A1 | 9/2008 | Harmon et al. |
| 2008/0220752 A1 | 9/2008 | Forstall et al. |
| 2008/0228056 A1 | 9/2008 | Blomquist et al. |
| 2008/0249386 A1 | 10/2008 | Besterman et al. |
| 2008/0262469 A1 | 10/2008 | Brister et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287755 A1 | 11/2008 | Sass et al. |
| 2008/0287906 A1 | 11/2008 | Burkholz et al. |
| 2008/0287922 A1 | 11/2008 | Panduro |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2008/0306434 A1 | 12/2008 | Dobbles et al. |
| 2008/0319383 A1 | 12/2008 | Byland et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054750 A1 | 2/2009 | Jennewine |
| 2009/0054753 A1 | 2/2009 | Robinson et al. |
| 2009/0058823 A1 | 3/2009 | Kocienda |
| 2009/0067989 A1 | 3/2009 | Estes et al. |
| 2009/0069743 A1 | 3/2009 | Krishnamoorthy et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0089710 A1 | 4/2009 | Wood et al. |
| 2009/0099521 A1 | 4/2009 | Gravesen et al. |
| 2009/0099523 A1 | 4/2009 | Grant et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0156990 A1 | 6/2009 | Wenger et al. |
| 2009/0163781 A1 | 6/2009 | Say et al. |
| 2009/0164239 A1 | 6/2009 | Hayter et al. |
| 2009/0197635 A1 | 8/2009 | Kim et al. |
| 2009/0198350 A1 | 8/2009 | Thiele |
| 2009/0204421 A1 | 8/2009 | Guimaraes |
| 2009/0212966 A1 | 8/2009 | Panduro |
| 2009/0221890 A1 | 9/2009 | Saffer et al. |
| 2009/0228214 A1 | 9/2009 | Say et al. |
| 2009/0253970 A1 | 10/2009 | Bashan et al. |
| 2009/0292247 A1 | 11/2009 | Basso et al. |
| 2009/0318791 A1 | 12/2009 | Kaastrup |
| 2009/0326343 A1 | 12/2009 | Gable et al. |
| 2009/0326472 A1 | 12/2009 | Carter et al. |
| 2010/0016700 A1 | 1/2010 | Sieh et al. |
| 2010/0017141 A1 | 1/2010 | Campbell et al. |
| 2010/0036326 A1 | 2/2010 | Matusch |
| 2010/0048358 A1 | 2/2010 | Tchao et al. |
| 2010/0057042 A1 | 3/2010 | Hayter |
| 2010/0064243 A1 | 3/2010 | Buck et al. |
| 2010/0077198 A1 | 3/2010 | Buck et al. |
| 2010/0114026 A1 | 5/2010 | Karratt et al. |
| 2010/0118037 A1 | 5/2010 | Sheikh et al. |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0174266 A1 | 7/2010 | Estes |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0273610 A1 | 10/2010 | Johnson |
| 2010/0280329 A1 | 11/2010 | Pedersen et al. |
| 2010/0286601 A1 | 11/2010 | Yodfat et al. |
| 2010/0295686 A1 | 11/2010 | Sloan et al. |
| 2010/0298765 A1 | 11/2010 | Budiman et al. |
| 2010/0305965 A1 | 12/2010 | Benjamin et al. |
| 2010/0315359 A1 | 12/2010 | Seong et al. |
| 2011/0009846 A1 | 1/2011 | Istoc et al. |
| 2011/0021584 A1 | 1/2011 | Berggren et al. |

(56) References Cited

U.S. PATENT DOCUMENTS

| | | |
|---|---|---|
| 2011/0028817 A1 | 2/2011 | Jin et al. |
| 2011/0040247 A1 | 2/2011 | Mandro et al. |
| 2011/0049394 A1 | 3/2011 | De Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0092788 A1 | 4/2011 | Long et al. |
| 2011/0124996 A1 | 5/2011 | Reinke et al. |
| 2011/0144586 A1 | 6/2011 | Michaud et al. |
| 2011/0152657 A1 | 6/2011 | Bielawa et al. |
| 2011/0160555 A1 | 6/2011 | Reifman et al. |
| 2011/0160652 A1 | 6/2011 | Yodfat et al. |
| 2011/0178472 A1 | 7/2011 | Cabiri |
| 2011/0190694 A1 | 8/2011 | Lanier et al. |
| 2011/0201911 A1 | 8/2011 | Johnson et al. |
| 2011/0202005 A1 | 8/2011 | Yodfat et al. |
| 2011/0205065 A1 | 8/2011 | Strachan et al. |
| 2011/0218495 A1 | 9/2011 | Remde |
| 2011/0230833 A1 | 9/2011 | Landman et al. |
| 2011/0238520 A1 | 9/2011 | Selley |
| 2011/0251509 A1 | 10/2011 | Beyhan et al. |
| 2011/0273388 A1 | 11/2011 | Joo et al. |
| 2011/0313349 A1 | 12/2011 | Krulevitch et al. |
| 2011/0313680 A1 | 12/2011 | Doyle et al. |
| 2011/0316562 A1 | 12/2011 | Cefai et al. |
| 2011/0319322 A1 | 12/2011 | Bashan et al. |
| 2012/0003935 A1 | 1/2012 | Lydon et al. |
| 2012/0010594 A1 | 1/2012 | Holt et al. |
| 2012/0022496 A1 | 1/2012 | Causey et al. |
| 2012/0030393 A1 | 2/2012 | Ganesh et al. |
| 2012/0053556 A1 | 3/2012 | Lee |
| 2012/0053560 A1 | 3/2012 | Kawamura |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0150556 A1 | 6/2012 | Galasso et al. |
| 2012/0159328 A1 | 6/2012 | Millington et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0215201 A1 | 8/2012 | Brauker et al. |
| 2012/0225134 A1 | 9/2012 | Komorowski |
| 2012/0226124 A1 | 9/2012 | Blomquist |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0238999 A1 | 9/2012 | Estes et al. |
| 2012/0250449 A1 | 10/2012 | Nakano |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2012/0330270 A1 | 12/2012 | Colton |
| 2013/0030358 A1 | 1/2013 | Yodfat et al. |
| 2013/0158503 A1 | 6/2013 | Kanderian et al. |
| 2013/0165901 A1 | 6/2013 | Ruchti et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0184547 A1 | 7/2013 | Taub et al. |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0318439 A1 | 11/2013 | Landis et al. |
| 2013/0324941 A1 | 12/2013 | Mann et al. |
| 2013/0331659 A1 | 12/2013 | Koski et al. |
| 2013/0332874 A1 | 12/2013 | Rosinko et al. |
| 2013/0332952 A1 | 12/2013 | Anandpura et al. |
| 2013/0332958 A1 | 12/2013 | Yang |
| 2013/0338453 A1 | 12/2013 | Duke et al. |
| 2013/0338576 A1 | 12/2013 | O'Connor et al. |
| 2013/0346858 A1 | 12/2013 | Neyrinck |
| 2014/0005633 A1 | 1/2014 | Finan |
| 2014/0012117 A1 | 1/2014 | Mensinger et al. |
| 2014/0018730 A1 | 1/2014 | Mueller-Pathle |
| 2014/0025400 A1 | 1/2014 | Galley et al. |
| 2014/0031786 A1 | 1/2014 | Kircher, Jr. et al. |
| 2014/0032549 A1 | 1/2014 | Mcdaniel et al. |
| 2014/0039383 A1 | 2/2014 | Dobbles et al. |
| 2014/0058749 A1 | 2/2014 | Galley et al. |
| 2014/0066859 A1 | 3/2014 | Ogawa et al. |
| 2014/0066886 A1 | 3/2014 | Roy et al. |
| 2014/0068487 A1 | 3/2014 | Steiger et al. |
| 2014/0073892 A1 | 3/2014 | Randloev et al. |
| 2014/0074033 A1 | 3/2014 | Sonderegger et al. |
| 2014/0088428 A1 | 3/2014 | Yang et al. |
| 2014/0108046 A1 | 4/2014 | Echeverria et al. |
| 2014/0121635 A1 | 5/2014 | Hayter |
| 2014/0127048 A1 | 5/2014 | Diianni et al. |
| 2014/0128839 A1 | 5/2014 | Diianni et al. |
| 2014/0129951 A1 | 5/2014 | Amin et al. |
| 2014/0135880 A1 | 5/2014 | Baumgartner et al. |
| 2014/0142508 A1 | 5/2014 | Diianni et al. |
| 2014/0146202 A1 | 5/2014 | Boss et al. |
| 2014/0154987 A1 | 6/2014 | Lee et al. |
| 2014/0160078 A1 | 6/2014 | Seo et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0317546 A1 | 10/2014 | Jacobson et al. |
| 2014/0325065 A1 | 10/2014 | Birtwhistle et al. |
| 2014/0344280 A1 | 11/2014 | Wei et al. |
| 2014/0358082 A1 | 12/2014 | Ohzawa |
| 2014/0380218 A1 | 12/2014 | Johnnie |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025498 A1 | 1/2015 | Estes |
| 2015/0025503 A1 | 1/2015 | Searle et al. |
| 2015/0041498 A1 | 2/2015 | Kakiuchi et al. |
| 2015/0067527 A1 | 3/2015 | Gardner et al. |
| 2015/0073337 A1 | 3/2015 | Saint et al. |
| 2015/0073754 A1 | 3/2015 | Okkonen et al. |
| 2015/0080842 A1 | 3/2015 | Mathys |
| 2015/0112264 A1 | 4/2015 | Kamen et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0141912 A1 | 5/2015 | Estes |
| 2015/0142325 A1 | 5/2015 | Thomson |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0277722 A1 | 10/2015 | Masterson et al. |
| 2015/0301691 A1 | 10/2015 | Qin |
| 2015/0306314 A1 | 10/2015 | Doyle et al. |
| 2015/0331995 A1 | 11/2015 | Zhao et al. |

(56) References Cited

U.S. PATENT DOCUMENTS

| | | |
|---|---|---|
| 2015/0351671 A1 | 12/2015 | Vanslyke et al. |
| 2015/0351672 A1 | 12/2015 | Vanslyke et al. |
| 2015/0356250 A1 | 12/2015 | Polimeni |
| 2015/0366945 A1 | 12/2015 | Greene |
| 2016/0000998 A1 | 1/2016 | Estes |
| 2016/0015891 A1 | 1/2016 | Papiorek |
| 2016/0019352 A1 | 1/2016 | Cohen et al. |
| 2016/0038673 A1 | 2/2016 | Morales |
| 2016/0038675 A1 | 2/2016 | Estes et al. |
| 2016/0038689 A1 | 2/2016 | Lee et al. |
| 2016/0051749 A1 | 2/2016 | Istoc |
| 2016/0058939 A1 | 3/2016 | Brewer et al. |
| 2016/0072841 A1 | 3/2016 | Caporal et al. |
| 2016/0082187 A1 | 3/2016 | Schaible et al. |
| 2016/0089491 A1 | 3/2016 | Smith |
| 2016/0089494 A1 | 3/2016 | Guerrini |
| 2016/0110064 A1 | 4/2016 | Shapira |
| 2016/0139671 A1 | 5/2016 | Jun et al. |
| 2016/0175520 A1 | 6/2016 | Palerm et al. |
| 2016/0220181 A1 | 8/2016 | Rigoard et al. |
| 2016/0228641 A1 | 8/2016 | Gescheit et al. |
| 2016/0235913 A1 | 8/2016 | Smith et al. |
| 2016/0243318 A1 | 8/2016 | Despa et al. |
| 2016/0250422 A1 | 9/2016 | Koch et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0317743 A1 | 11/2016 | Estes |
| 2016/0331310 A1 | 11/2016 | Kovatchev |
| 2016/0354543 A1 | 12/2016 | Cinar et al. |
| 2016/0357371 A1 | 12/2016 | Lee |
| 2016/0361494 A1 | 12/2016 | Jurg et al. |
| 2017/0003848 A1 | 1/2017 | Wakayanagi et al. |
| 2017/0007882 A1 | 1/2017 | Werner |
| 2017/0017374 A1 | 1/2017 | Herz |
| 2017/0021096 A1 | 1/2017 | Cole et al. |
| 2017/0049386 A1 | 2/2017 | Abraham et al. |
| 2017/0049957 A1 | 2/2017 | Michaud |
| 2017/0056591 A1 | 3/2017 | Breton et al. |
| 2017/0100538 A1 | 4/2017 | Mhatre et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0165416 A1 | 6/2017 | Saint |
| 2017/0173261 A1 | 6/2017 | O'Connor et al. |
| 2017/0173262 A1 | 6/2017 | Veltz |
| 2017/0176952 A1 | 6/2017 | Misaki et al. |
| 2017/0188943 A1 | 7/2017 | Braig et al. |
| 2017/0189614 A1 | 7/2017 | Mazlish et al. |
| 2017/0189625 A1 | 7/2017 | Cirillo et al. |
| 2017/0193184 A1 | 7/2017 | Hayter et al. |
| 2017/0199985 A1 | 7/2017 | Mazlish et al. |
| 2017/0203030 A1 | 7/2017 | Brewer et al. |
| 2017/0203036 A1 | 7/2017 | Mazlish et al. |
| 2017/0203037 A1 | 7/2017 | Desborough et al. |
| 2017/0203038 A1 | 7/2017 | Desborough et al. |
| 2017/0203039 A1 | 7/2017 | Desborough et al. |
| 2017/0216524 A1 | 8/2017 | Haider et al. |
| 2017/0224910 A1 | 8/2017 | Yodfat et al. |
| 2017/0232195 A1 | 8/2017 | Desborough et al. |
| 2017/0239415 A1 | 8/2017 | Hwang et al. |
| 2017/0242975 A1 | 8/2017 | Kahlbaugh |
| 2017/0255771 A1 | 9/2017 | Miyakawa |
| 2017/0258987 A1 | 9/2017 | Caspers |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0316592 A1 | 11/2017 | Kamath et al. |
| 2017/0332952 A1 | 11/2017 | Desborough et al. |
| 2017/0347971 A1 | 12/2017 | Davis et al. |
| 2017/0348482 A1 | 12/2017 | Duke et al. |
| 2017/0348484 A1 | 12/2017 | Duke et al. |
| 2017/0351842 A1 | 12/2017 | Booth et al. |
| 2018/0001006 A1 | 1/2018 | Schade et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0089395 A1 | 3/2018 | Desborough et al. |
| 2018/0092576 A1 | 4/2018 | Ambrsio |
| 2018/0101297 A1 | 4/2018 | Yang et al. |
| 2018/0126073 A1 | 5/2018 | Wu et al. |
| 2018/0133397 A1 | 5/2018 | Estes |
| 2018/0147362 A1 | 5/2018 | Arenas et al. |
| 2018/0150614 A1 | 5/2018 | Sokolovskyy et al. |
| 2018/0161499 A1 | 6/2018 | Al-Ali et al. |
| 2018/0169334 A1 | 6/2018 | Grosman et al. |
| 2018/0200434 A1 | 7/2018 | Mazlish et al. |
| 2018/0200435 A1 | 7/2018 | Mazlish et al. |
| 2018/0200436 A1 | 7/2018 | Mazlish et al. |
| 2018/0200437 A1 | 7/2018 | Mazlish et al. |
| 2018/0200438 A1 | 7/2018 | Mazlish et al. |
| 2018/0200439 A1 | 7/2018 | Mazlish et al. |
| 2018/0200441 A1 | 7/2018 | Desborough et al. |
| 2018/0204636 A1 | 7/2018 | Edwards et al. |
| 2018/0207380 A1 | 7/2018 | Lantz et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0361060 A9 | 12/2018 | Rosinko |
| 2018/0369479 A1 | 12/2018 | Hayter et al. |
| 2019/0001067 A1 | 1/2019 | Berey et al. |
| 2019/0015024 A1 | 1/2019 | Desborough et al. |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0175841 A1 | 6/2019 | Sjolund et al. |
| 2019/0183434 A1 | 6/2019 | Sjolund et al. |
| 2019/0184091 A1 | 6/2019 | Sjolund et al. |
| 2019/0184111 A1 | 6/2019 | Sjolund et al. |
| 2019/0240403 A1 | 8/2019 | Palerm et al. |
| 2019/0265871 A1 | 8/2019 | Eim et al. |
| 2019/0274624 A1 | 9/2019 | Mazlish et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0348166 A1 | 11/2019 | Booth et al. |
| 2019/0374714 A1 | 12/2019 | Rioux et al. |
| 2020/0001006 A1 | 1/2020 | Pizzochero et al. |
| 2020/0042166 A1 | 2/2020 | Burns et al. |
| 2020/0046268 A1 | 2/2020 | Patek et al. |
| 2020/0097131 A1 | 3/2020 | Bowden et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0201494 A1 | 6/2020 | Allington et al. |
| 2020/0219625 A1 | 7/2020 | Kahlbaugh |
| 2020/0236212 A1 | 7/2020 | Vinna et al. |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |

FOREIGN PATENT DOCUMENTS

| | | |
|---|---|---|
| CA | 1040271 A | 10/1978 |
| CA | 2543545 A1 | 5/2005 |
| CA | 3026851 A1 | 2/2020 |
| CN | 1297140 A | 5/2001 |
| CN | 101208699 A | 6/2008 |
| CN | 101610718 A | 12/2009 |
| CN | 101785702 A | 7/2010 |
| CN | 102300501 A | 12/2011 |
| CN | 104620244 A | 5/2015 |
| DE | 4200595 A1 | 7/1993 |

(56) References Cited

FOREIGN PATENT DOCUMENTS

| | | |
|---|---|---|
| DE | 19627619 | 1/1998 |
| DE | 19756872 A1 | 7/1999 |
| DE | 10236669 A1 | 2/2004 |
| EM | 0006276170001 | 1/2007 |
| EM | 0006276170002 | 1/2007 |
| EM | 0006276170003 | 1/2007 |
| EM | 0007326490001 | 6/2007 |
| EM | 0007326490002 | 6/2007 |
| EM | 0031267050001 | 7/2016 |
| EM | 0031267050002 | 7/2016 |
| EM | 0031267050003 | 7/2016 |
| EM | 0031267050004 | 7/2016 |
| EP | 0026056 A1 | 4/1981 |
| EP | 0062974 A1 | 10/1982 |
| EP | 0275213 A2 | 7/1988 |
| EP | 0341049 A2 | 11/1989 |
| EP | 0496141 A1 | 7/1992 |
| EP | 0496305 A2 | 7/1992 |
| EP | 0549341 A1 | 6/1993 |
| EP | 0580723 A1 | 2/1994 |
| EP | 0612004 A1 | 8/1994 |
| EP | 0721358 A1 | 7/1996 |
| EP | 0867196 A2 | 9/1998 |
| EP | 0939451 A1 | 9/1999 |
| EP | 1045146 A2 | 10/2000 |
| EP | 1136698 A1 | 9/2001 |
| EP | 1177802 A1 | 2/2002 |
| EP | 1376759 A2 | 1/2004 |
| EP | 1491144 A1 | 12/2004 |
| EP | 1495775 A1 | 1/2005 |
| EP | 1527792 A1 | 5/2005 |
| EP | 1571582 A2 | 9/2005 |
| EP | 0801578 B1 | 7/2006 |
| EP | 1754498 A1 | 2/2007 |
| EP | 1818664 A1 | 8/2007 |
| EP | 2139382 A1 | 1/2010 |
| EP | 2397181 A1 | 12/2011 |
| EP | 2468338 A1 | 6/2012 |
| EP | 2585252 A1 | 5/2013 |
| EP | 2666520 A1 | 11/2013 |
| EP | 2695573 A2 | 2/2014 |
| EP | 2703024 A1 | 3/2014 |
| EP | 2830499 A1 | 2/2015 |
| EP | 2897071 A1 | 7/2015 |
| EP | 2943149 A1 | 11/2015 |
| EP | 3177344 A1 | 6/2017 |
| EP | 3193979 A1 | 7/2017 |
| EP | 3314548 A1 | 5/2018 |
| EP | 3607985 A1 | 2/2020 |
| FR | 2096275 A5 | 2/1972 |
| FR | 2585252 A1 | 1/1987 |
| GB | 0747701 | 4/1956 |
| GB | 1125897 A | 9/1968 |
| GB | 2218831 A | 11/1989 |
| GB | 2443261 A | 4/2008 |
| IN | 105899247 A | 8/2016 |
| JP | 51-125993 A | 11/1976 |
| JP | 02-131777 A | 5/1990 |
| JP | 2004-283378 A | 10/2004 |
| JP | 2005-326943 A | 11/2005 |
| JP | 2007-525276 A | 9/2007 |
| JP | 2008-513142 A | 5/2008 |
| JP | 2012-527981 A | 11/2012 |
| JP | 2017-516548 A | 6/2017 |
| JP | 2017-525451 A | 9/2017 |
| JP | 2018-153569 A | 10/2018 |
| JP | 2019-525276 A | 9/2019 |
| TW | 200740148 A | 10/2007 |
| TW | M452390 U | 5/2013 |
| WO | 86/06796 A1 | 11/1986 |
| WO | 90/15928 A1 | 12/1990 |
| WO | 95/09021 A1 | 4/1995 |
| WO | 97/21457 A1 | 6/1997 |
| WO | 98/00193 A1 | 1/1998 |
| WO | 98/04301 A1 | 2/1998 |
| WO | 98/11927 A1 | 3/1998 |
| WO | 98/55073 A1 | 12/1998 |
| WO | 98/57683 A1 | 12/1998 |
| WO | 99/10040 A1 | 3/1999 |
| WO | 99/10049 A1 | 3/1999 |
| WO | 99/21596 A1 | 5/1999 |
| WO | 99/39118 A1 | 8/1999 |
| WO | 99/48546 A1 | 9/1999 |
| WO | 99/56803 A1 | 11/1999 |
| WO | 99/62576 A1 | 12/1999 |
| WO | 00/30705 A1 | 6/2000 |
| WO | 00/32258 A1 | 6/2000 |
| WO | 00/48112 A2 | 8/2000 |
| WO | 01/72354 A2 | 10/2001 |
| WO | 01/72360 A1 | 10/2001 |
| WO | 01/78812 A1 | 10/2001 |
| WO | 01/91822 A1 | 12/2001 |
| WO | 01/91833 A1 | 12/2001 |
| WO | 02/15954 A1 | 2/2002 |
| WO | 02/26282 A2 | 4/2002 |
| WO | 02/40083 A2 | 5/2002 |
| WO | 02/43866 A2 | 6/2002 |
| WO | 02/57627 A1 | 7/2002 |
| WO | 02/68015 A2 | 9/2002 |
| WO | 02/76535 A1 | 10/2002 |
| WO | 02/82990 A1 | 10/2002 |
| WO | 02/84336 A2 | 10/2002 |
| WO | 2002/100469 A2 | 12/2002 |
| WO | 03/16882 A1 | 2/2003 |
| WO | 03/26726 A1 | 4/2003 |
| WO | 03/39362 A1 | 5/2003 |
| WO | 03/45233 A1 | 6/2003 |
| WO | 03/97133 A1 | 11/2003 |
| WO | 2003/103763 A1 | 12/2003 |
| WO | 2004/043250 A1 | 5/2004 |
| WO | 2004/056412 A2 | 7/2004 |
| WO | 2004/092715 A1 | 10/2004 |
| WO | 2004/110526 A1 | 12/2004 |
| WO | 2005/002652 A2 | 1/2005 |
| WO | 2005/039673 A2 | 5/2005 |
| WO | 2005/051170 A2 | 6/2005 |
| WO | 2005/072794 A2 | 8/2005 |
| WO | 2005/072795 A2 | 8/2005 |
| WO | 2005/082436 A1 | 9/2005 |
| WO | 2005/110601 A1 | 11/2005 |
| WO | 2005/113036 A1 | 12/2005 |
| WO | 2006/053007 A2 | 5/2006 |
| WO | 2006/067217 A2 | 6/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |
| WO | 2007/064835 A1 | 6/2007 |
| WO | 2007/066152 A2 | 6/2007 |
| WO | 2007/078937 A2 | 7/2007 |
| WO | 2007/141786 A1 | 12/2007 |
| WO | 2008/024810 A2 | 2/2008 |
| WO | 2008/029403 A1 | 3/2008 |
| WO | 2008/133702 A1 | 11/2008 |
| WO | 2009/039203 A2 | 3/2009 |
| WO | 2009/045462 A1 | 4/2009 |
| WO | 2009/049252 A1 | 4/2009 |
| WO | 2009/066287 A2 | 5/2009 |
| WO | 2009/066288 A1 | 5/2009 |
| WO | 2009/098648 A2 | 8/2009 |
| WO | 2009/134380 A2 | 11/2009 |
| WO | 2010/022069 A2 | 2/2010 |
| WO | 2010/053702 A1 | 5/2010 |
| WO | 2010/077279 A1 | 7/2010 |
| WO | 2010/091102 A1 | 8/2010 |
| WO | 2010/132077 A1 | 11/2010 |
| WO | 2010/138848 A1 | 12/2010 |
| WO | 2010/139793 A1 | 12/2010 |
| WO | 2010/147659 A2 | 12/2010 |
| WO | 2011/031458 A1 | 3/2011 |
| WO | 2011/075042 A1 | 6/2011 |
| WO | 2011/095483 A1 | 8/2011 |
| WO | 2011/133823 A1 | 10/2011 |
| WO | 2011/163450 A1 | 12/2011 |

(56) References Cited

FOREIGN PATENT DOCUMENTS

| | | |
|---|---|---|
| WO | 2012/045667 A2 | 4/2012 |
| WO | 2012/073032 A1 | 6/2012 |
| WO | 2012/108959 A1 | 8/2012 |
| WO | 2012/134588 A1 | 10/2012 |
| WO | 2012/177353 A1 | 12/2012 |
| WO | 2012/178134 A2 | 12/2012 |
| WO | 2013/050535 A2 | 4/2013 |
| WO | 2013/078200 A1 | 5/2013 |
| WO | 2013/134486 A2 | 9/2013 |
| WO | 2013/149186 A1 | 10/2013 |
| WO | 2013/177565 A1 | 11/2013 |
| WO | 2013/182321 A1 | 12/2013 |
| WO | 2014/029416 A1 | 2/2014 |
| WO | 2014/035672 A2 | 3/2014 |
| WO | 2014/109898 A1 | 7/2014 |
| WO | 2014/110538 A1 | 7/2014 |
| WO | 2014/149357 A1 | 9/2014 |
| WO | 2014/179774 A1 | 11/2014 |
| WO | 2014/194183 A2 | 12/2014 |
| WO | 2015/056259 A1 | 4/2015 |
| WO | 2015/061493 A1 | 4/2015 |
| WO | 2015/073211 A1 | 5/2015 |
| WO | 2015/081337 A2 | 6/2015 |
| WO | 2015/117082 A1 | 8/2015 |
| WO | 2015/117854 A1 | 8/2015 |
| WO | 2015/167201 A1 | 11/2015 |
| WO | 2015/177082 A1 | 11/2015 |
| WO | 2015/187366 A1 | 12/2015 |
| WO | 2016/004088 A1 | 1/2016 |
| WO | 2016/022650 A1 | 2/2016 |
| WO | 2016019192 A1 | 2/2016 |
| WO | 2016/041873 A1 | 3/2016 |
| WO | 2016/089702 A1 | 6/2016 |
| WO | 2016/141082 A1 | 9/2016 |
| WO | 2016/161254 A1 | 10/2016 |
| WO | 2017/004278 A1 | 1/2017 |
| WO | 2017/009724 | 1/2017 |
| WO | 2017/091624 A1 | 6/2017 |
| WO | 2017/105600 A1 | 6/2017 |
| WO | 2017/184988 A1 | 10/2017 |
| WO | 2017/187177 A1 | 11/2017 |
| WO | 2017/205816 A1 | 11/2017 |
| WO | 2018/009614 A1 | 1/2018 |
| WO | 2018/067748 A1 | 4/2018 |
| WO | 2018/120104 A1 | 7/2018 |
| WO | 2018/136799 A1 | 7/2018 |
| WO | 2018/204568 A1 | 11/2018 |
| WO | 2019/077482 A1 | 4/2019 |
| WO | 2019/094440 A1 | 5/2019 |
| WO | 2019/213493 A1 | 11/2019 |
| WO | 2019/246381 A1 | 12/2019 |
| WO | 2020/081393 A1 | 4/2020 |
| WO | 2021/011738 A1 | 1/2021 |

OTHER PUBLICATIONS

Synchronise, IOS 7 Interface Symbol. By Flaticon. Freepik.com. Date: 2015. Retrieved from Internet: <https://www.freepik.com/free-icon/synchronise-ios-7-inlerface-symbol_751804.htm#term=arrows&page=69&position=14> (Year: 2015).
T:slimx2 Insulin Pump User Guide, Tandem Diabetes Care, Jul. 22, 2016, p. 50.
The Medtronic Diabetes Connection, 2006, 6 pages.
Three icons—Ready, Set and Go Nov. 29, 2015, depositphotos, site visited Apr. 21, 2020: https://depositphotos.com/91436542/stock-illustration-countdown-ready-set-go-colorful.html (Year: 2015).
Vozeh et al., "Feedback Control Methods for Drug Dosage Optimisation, Concepts, Classification and Clinical Application, Clinical Pharmacokinetics", vol. 10, No. 6, pp. 457-476, Nov.-Dec. 1985.
Xilas Temp Touch, "The latest in high-tech and convenient devices," DOCNews, vol. 2, No. 7, Jul. 1, 2005, http://docnews.diabetesjournals.ordlcgi/contenl/foll/2/7i 13, 3 pages.
Zhang et al., Second Insulin Pump Safety Meeting: Summary Report, Journal of Diabetes Science and Technology 2010, pp. 488-493. (Year: 2010).
Chinese Search Report and Written Opinion from Chinese Application No. 201780068331.0, dated Apr. 23, 2021, 26 pages.
Accu-Chek Spirit, "Pump Therapy Made for You," Roche, 2006, 6 pages.
Ansyari, Nazurrudin. "Circle Badge Set." iconfinder.com. Added Aug. 15, 2016. Accessed Jan. 27, 2020. Available online at URL: https://www.iconfinder.com/iconsets/circle-badge-set (Year: 2016).
Arrow Repeat. By Flaticon. Freepik.com. Date: 2014. Retrieved from Internet: <https://www.freepik.com/free-icon/arrow-repeat 694329.htm#term=arrows&page=47&position=67> (Year: 2014).
Arrows Curves Forming an Oval Shape. By Flaticon. Freepik.com. Date: 2015. Retrieved from Internet: <https://www.freepik.com/free-icon/arrows-curves-forming-an-oval-shape_746143.htm> (Year: 2015).
Arrows, Couple, IOS 7 Interface Symbol. By Flaticon. Freepik.com. Date: 2015. Retrieved from Internet: <https://www.freepik.com/free-icon/arrows-couple-ios-7-interface symbo_751266.htm#term=arrows&page=68&position=43> (Year: 2015).
Baruah, Insulin Pens: The Modern Delivery Devices, Google Scholar 2011, pp. 38-40. (Year: 2011).
Bhalla, Raveesh, Understanding Material Design Part II, Sep. 28, 2014, Medium.com [online], [site visited Apr. 11, 2018], Available from Internet: https://medium.com/@raveeshbhalla/understanding-material-design-cf2d60a16de3 (Year: 2014).
Bigfoot Biomedical Reveals its Automated Insulin Delivery System, diaTribe, Date published: Jan. 25, 2016 <https://diatribe.org/bigfool-biomedical-reveals-its-automated-insulin-delivery-system>.
Bode et al., Diabetes Management in the New Millennium Using Insulin Pump Therapy, Wiley Inter Science 2002, pp. 514-520. (Year: 2002).
Centers for Disease Control and Prevention, Number (in Millions) of Adults with Diabetes by Diabetes Medication Status, United States, 1997-2011, http://www.cdc.gov/diabetes/statislics/meduse/fig1.him, 2013.
Clean Toggle Button Navigation Menu PSD Jan. 24, 2014, WeLoveSoLo, site visited Oct. 19, 2018: https://www.welovesolo.com/clean-toggle-button-navigation-menu-psd/.
Collins and Lee, "Microfluidic flow transducer based on the measurement of electrical admittance," Lab Chip, 2004, 4:7-10.
Copp et al., "Simultaneous Model Predictive Control and Moving Horizon Estimation for Blood Glucose Regulation in Type 1 Diabetes", Optimal Control Applications and Methods, Wiley InterScience, DOI: 10.1002/oca, pp. 1-15, Oct. 2016.
Curved Arrow to the Right. By Flaticon. Freepik.com. Date: 2015. Retrieved from Internet: <https://www.freepik.com/free-icon/curved-arrow-to-the-right 735735.htm#/term=arrows&page=59&position=69> (Year: 2015).
Dassau and Associates, "12-Week 24/7 Ambulatory Artificial Pancreas With Weekly Adaptation of Insulin Delivery Settings: Effect on Hemoglobin A1C and Hypoglycemia", Diabetes Care, Oct. 13, 2017.
Debiotech News Release, "Debiotech reveals its new miniaturized Disposable Insulin Nanopump (Trademark) for Diabetes therapy," available at http://www.debiotech.com/news/nw 159.html Apr. 24, 2006, 3 pages.
Delaney, Chelsey, "4 apps for tracking your fertility" Jun. 6, 2016, Bedsider, site visited Oct. 19, 2018: https://www.bedsider.org/features/647-4-apps-for-tracking-your-fertility.
Dreyfus, Henry. Symbol Source Book. New York, McGraw-Hill, 1972. pp. 52, 180, and 184. (Year: 1972).
Dreyfuss, Henry. Symbol Sourcebook. Van Nostrand Reinhold Company. Date published: 1984. p. 28. (Year: 1984).
E. Salzsieder, G. Albrecht, E. Jutzi, and U. Fischer, Estimation of Individually Adapted Control Parameten for an Artificial Beta Cell, Biomedica Biochimica Acta. 43(5) pp. 585-596, May 1984.
Eren-Oruklu et al., Adaptive Control Strategy for Regulation of Blood Glucose Levels in Patients with Type 1 Diabetes, ScienceDirect 2009, pp. 1333-1346. (Year: 2009).

(56) References Cited

OTHER PUBLICATIONS

European search report Mailed on Dec. 5, 2019 for EP Application No. 17882173.
Fischer et al., "In Vivo Comparison of Different Algorithms for the Artificial Beta-Cell", Artificial Organs, 9(2), International Society for Artificial Organs, May 1985, New York.
Grill et al., Exercise and Postprandial Lipid Metabolism: an Update on Potential Mechanisms and Interactions with High-Carbohydrate Diets/(Review), Elsevier 2003, pp. 122-132. (Year: 2003).
Guy A. Dumont, "Feedback Control for Clinicians, Springer Science+Media", Apr. 12, 2013, New York.
Harvey et al., Quest for the Artificial Pancreas, IEEE 2010, pp. 53-62. (Year: 2010).
Hoskins, Mike, News: Bigfoot Closed Loop, Jul. 17, 2017, Healthline.com [online], [visited Jan. 22, 2019]. Internet: https://web.archive.org/web/20170810052840/https://www.diabetesdaily.com/blog/bigfoot-biomedical-aims-to-take-multiple-daily-injections-to-the-next-level-with-timesulin-acquisition (Year: 2017).
Hurley, Dan. Artificial Pancreas Makers Race to Markel. Discover. Date published: Apr. 12, 2016. <http://discovermagazine.com/2016/may/13-priming-the-pump>.
International Search Report for International Application No. PCT/US17/065894, mailed Mar. 7, 2018, 2 pages.
International Written Opinion for International Application No. PCT/US17/065894, Mailed on Mar. 7, 2018, 7 pages.
JDRF, Statistics: JDRF and Diabetes, http://jdrf.org/aboul-jdrf/facl-sheels/jdrf-anddiabeles- statistics/, 2014.
Karnes, Chris. "Kids Mental Health App." dribbble.com. Feb. 1, 2020. Accessed May 7, 2020. Available online at URL: https://dribbble.com/shots/9841070-Kids-Mental-Health-App (Year: 2020).
Kumar, Rohit. "Health App." dribbble.com. May 14, 2015. Accessed May 7, 2020. Available online at URL: https://dribbble.com/shots/2062723-Health-App (Year: 2015).
Kuwayama, Yasaburo. Trademarks & Symbols. vol. 2: Symbolical Designs. Van Nostrand Reinhold Company. Date published: 1973. p. 136. (Year: 1973).
Medical Set. iconfinder.com. Added Apr. 7, 2017. Accessed Jan. 27, 2020. Available online at URL: https://www.iconfinder.com/iconsets/medical-set-5 (Year: 2017).
Medtronic News Release, "Medtronic Receives FDA Approval for World's First Insulin Pump with Real-time Continuous Glucose Monitoring," Apr. 13, 2006, 3 pages.
Omnipod Horizon: Automated Glucose Control Jun. 2017, 2 pages.
OmniPod Insulin Management System—Investor Relations—Press Release, Feb. 1, 2005, http://investors.insulet.com/phoenix.zhtml?c=209336&p=irol-newsArticle&ID=988708&highlight= 1 page.
OmniPod Quick Start Guide, 2007, 2 pages.
Owens et al., Run-to-Run Control of Blood Glucose Concentrations for People with Type 1 Diabetes Mellitus, IEEE 2006, pp. 996-1005. (Year: 2006).
Patent Abstracts of Japan, vol. 1999, No. 04, and JP 11 010036, Apr. 30, 1999 and Jan. 19, 1999, Toray Ind. Inc.
Pearson, Practical Aspect of Insulin Pen Devices, Journal of Diabetes Science and Technology 2010, pp. 522-531. (Year: 2010).
Refresh Arrow Loop. By Flaticon. Freepik.com. Date:2014. Retrieved from Internet: <https://www.freepik.com/free-icon/refresh-arrow-loop 705291 .htm#/term=arrows&page=49&position=43> (Year: 2014).
Refreshing. By Flaticon. Freepik.com. Date: 2016. Retrieved from Internet: <https://www.freepik.com/free-icon/refreshing_807573.htm#/term=arrows&page=26&position=26> (Year: 2016).
Sara Krugman, Bionic Pancreas User Interface (3/4): Interface Details, Tidepool.org, Jul. 20, 2015, pp. 4, 8.
Schiavon et al., "Quantitative Estimation of Insulin Sensitivity in Type 1 Diabetic Subjects Wearing a Sensor-augmented Insulin Pump", Diabetes Care, vol. 37, pp. 1216-1223, May 2014.

Shishir, Shahidl Islam. "Med-i App | Splash Home and Logo." dribbble.com. Jul. 28, 2019. Accessed May 7, 2020. Available online at URL: https://dribbble.com/shots/6852974-Med-i-App-I-Splash-Home-and-Logo (Year: 2019).
Simmons, Cory, "How to Make Your Own Button UI Kil with Super-Clean Syntax" Dec. 23, 2014, envato tuts+, site visited Sep. 19, 2019: https://webdesign.lutsplus.com/lutorials/how-lo-make-your-0wn-button-ui-kil-wilh-super-clean-syntax-cms-22946.
Sindaco et al., Use of the Short-acting Insulin Analogue Lispro in Intensive Treatment of Type 1 Diabetes Mellitus: Importance of Appropriate Replacement of Basal Insulin and Time-interval Injection-meal, Diabetic Medicine 1998, pp. 592-600. (Year: 1998).
Smart et al., "Can children with type 1 diabetes and their caregivers estimate the carbohydrate content of meals and snacks?" Diabetic Medicine, 27, No. 3 (2010) pp. 38-353.
Dreyfuss, Henry. Symbol Sourcebook: An Authoritative Guide to International Graphic Symbols. Van Nostrand Reinhold, 1984. p. 52. (Year: 1984).
European Communication pursuant to Article 94(3) EPC for European Application No. 17882173.2, dated Jun. 30, 2022, 7 pages.
Kumar, Rohit. "Health App." dribbble.com. May 14, 2015. Accessed 517/2020. Available online at URL: https://dribbble.com/shots/2062723-Health-App (Year: 2015).
U.S. Trademark U.S. Appl. No. 85/698,749 to Mmillenniumm Group Ing. Filed Aug. 8, 2012. Retrieved Mar. 7, 2022 online via Trademark Electronic Search System (TESS) at https://www.uspto.gov/trademarks-application-process/search-trademark-database. (Year: 2012).
U.S. Trademark U.S. Appl. No. 86/854,669 to DynoSense Corp. Filed Dec. 19, 2015. Retrieved Mar. 7, 2022 online via Trademark Electronic Search System (TESS) at https://www.uspto.gov/trademarks-application-process/search-trademark-database. (Year: 2015).
"LifeScan Receives FDA Clearance for One Touch VerioSync Bluetooth Blood Glucose Meter" Mar. 7, 2013, posted at medgadget.com, [site visited May 30, 2023]. https://www.medgadget.com/2013/03/lifescan-receives-fda-clearance-for-onetouch-veriosync-bluetooth-blood-glucose-meter.html (Year: 2013).
"SeebeckCell Technologies" Jul. 7, 2022, posted at greentownlabs.com, [site visited May 30, 2023]. https://web.archive.org/web/20220707134432/https://greentownlabs.com/members/seebeckcell-technologies (Year: 2022).
Canadian Requisition by the Examiner for Canadian Application No. 3,036,266, dated Mar. 30, 2023, 4 pages.
Chinese First Office Action for Chinese Application No. 201910969068.3 dated Nov. 21, 2022, 13 pages with translation.
Desborough et al. Insulin Delivery System and Methods with Risk Based Set Points, filed May 22, 2017, U.S. Appl. No. 15/601,282, 101 pages.
European Communication pursuant to Article 94(3) EPC for European Application No. 17857362.2, dated Mar. 20, 2023, 5 pages.
European Examination Report for EP Application No. 17857364.8, mailed Apr. 13, 2023, 5 pages.
Canadian Requisition by the Examiner for Canadian Application No. 3,037,432, dated Sep. 20, 2023, 4 pages.
Chinese Second Office Action for Chinese Application No. 201910969068.3, mailed Nov. 30, 2023, 15 pages with English translation.
Examination Report No. 1 for Australian Patent Application No. 2022202031, mailed Mar. 10, 2023, 3 pages.
Indepth—Icon set Jul. 25, 2014, posted at dribbble.com, [site visited Sep. 21, 2023]. https://dribbble.com/shots/1657115-Indepth-Icon-set-GIF (Year: 2014).
Insulcheck, "Eliminating the doubt for people with diabetes," Aug. 31, 2015, Innovation Zed Ltd., Available https://web.archive.org/web/20150831011744/http://www.insulcheck.com/profile (Year: 2015).
Timesulin, "How to use it," Oct. 13, 2011, Patients Pending Ltd,, Available https://web.archive.org/web/20111013145747/http://timesulin.com/how-to-use-it (Year: 2011).
Examination Report No. 1 for Australian Patent Application No. 2023202630, issued May 15, 2024, 3 pages.

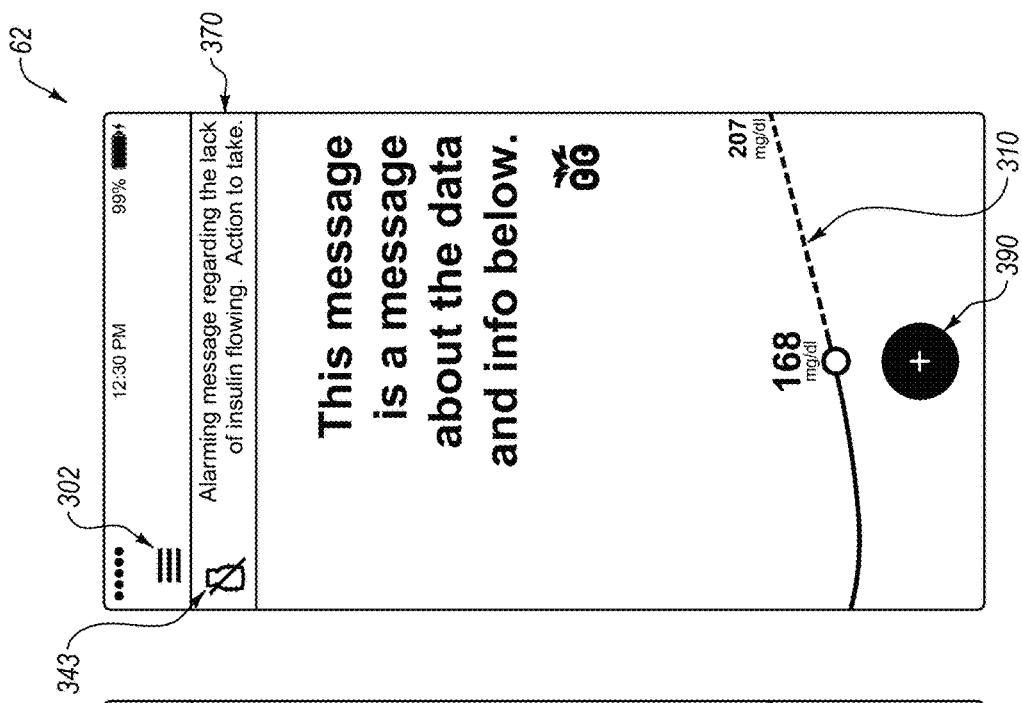
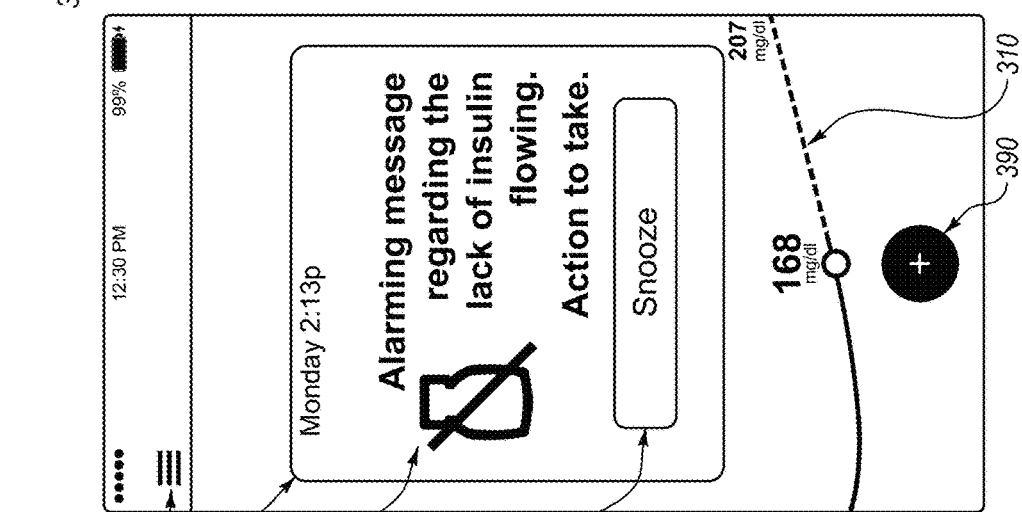
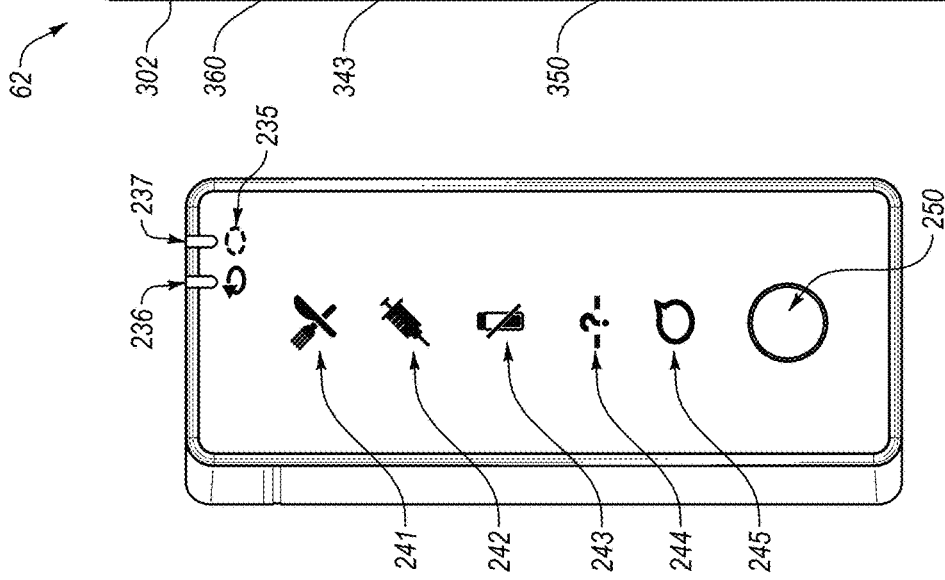

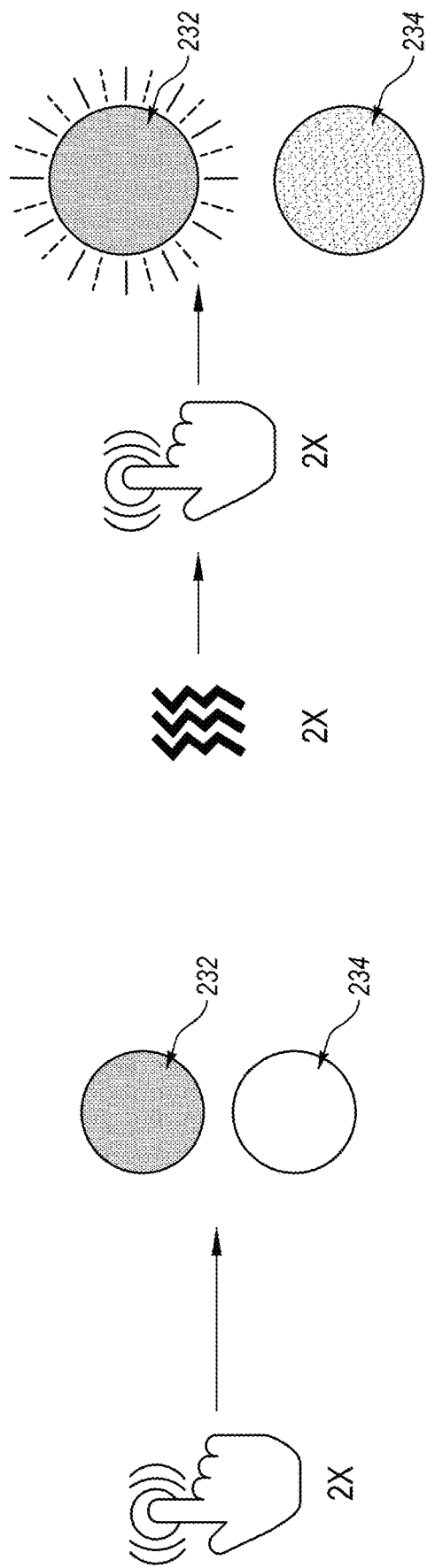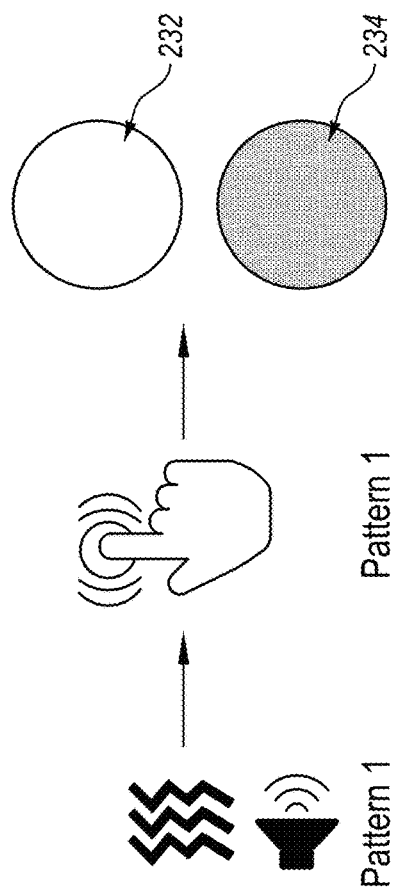
FIG. 15A
FIG. 15B
FIG. 15C

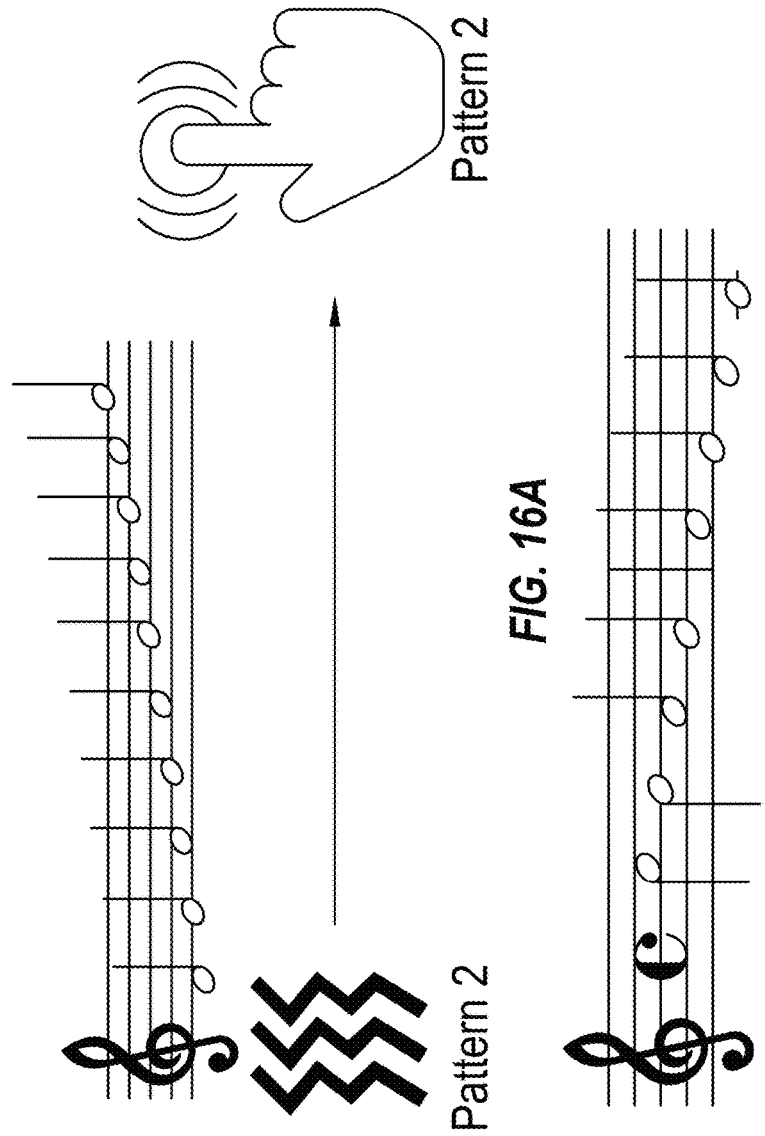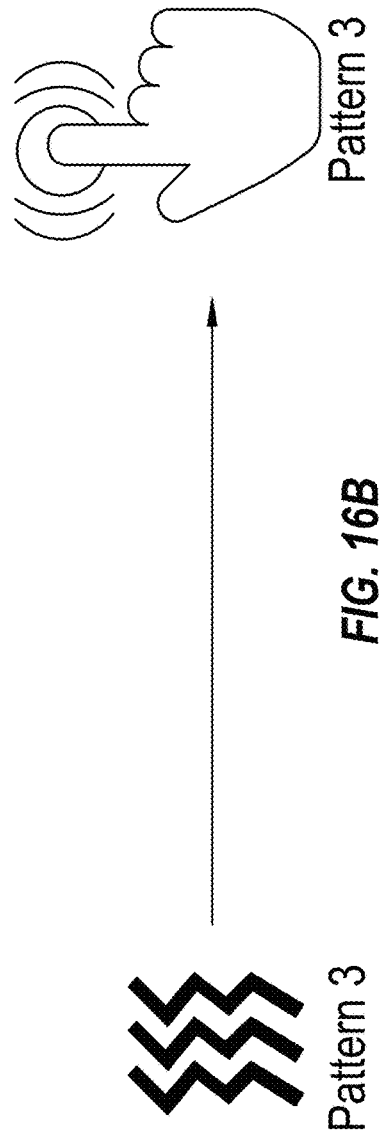

ALARMS AND ALERTS FOR MEDICATION DELIVERY DEVICES AND SYSTEMS

CROSS-REFERENCE TO RELATED APPLICATIONS

This application is a continuation of U.S. patent application Ser. No. 16/335,163 filed Mar. 20, 2019, now U.S. Pat. No. 11,096,624 issued Aug. 24, 2021, the disclosure of which is hereby incorporated herein in its entirety by this reference, which is a national phase entry under 35 U.S.C. § 371 of International Patent Application PCT/US2017/065894, filed Dec. 12, 2017, designating the United States of America and published in English as International Patent Publication WO2018/111927 A1 on Jun. 21, 2018, which claims the benefit under Article 8 of the Patent Cooperation Treaty to U.S. Provisional Patent Application Ser. No. 62/433,124, filed Dec. 12, 2016, the disclosure of each of which is hereby incorporated herein in its entirety by this reference.

TECHNICAL FIELD

This disclosure relates to alarms and alerts for medication delivery devices and systems, particularly for medication delivery systems that have a medication delivery device that communicates with a primary user-interface for the medication delivery device and related systems and methods.

BACKGROUND

People with Type I, Type II, or gestational diabetes must track their blood glucose levels and sometimes treat their condition to maintain appropriate blood glucose levels. Control of diabetes can include the monitoring of blood glucose levels using a blood glucose monitor (BGM) and sometimes a continuous glucose monitor (CGM). People with Type I, and some people with Type II or gestational diabetes, require insulin or an analog thereof. Because it cannot be taken orally, insulin is injected with a syringe or delivered subcutaneously by an external infusion pump. Excessive insulin delivery, however, can result in acute hypoglycemia, which can result in severe bodily injury and/or death. The failure to administer an appropriate amount of insulin to a person with diabetes, however, results in hyperglycemia, which can result in severe bodily injury and/or death. Because of the grave risks associated with diabetes, CGMs and insulin infusion pump systems typically provide a series of alarms and alerts that draw attention to the user's current glycemic condition, system conditions, and/or other potential issues, but these alarms and alerts can result in alert fatigue. Users having alert fatigue may start to ignore alarms or alerts or discontinue use of a CGM or insulin infusion pump, thus reducing the quality of their treatment. Moreover, users may wish to keep their external infusion pump or CGM concealed from view in order to avoid unwanted attention. Accordingly, there is a need for an improved system for providing diabetes-related information, alerts, and alarms.

BRIEF SUMMARY

Medication delivery systems, methods, and devices provided herein include at least a medication delivery device (e.g., an insulin delivery device) and a remote user-interface device (e.g., a smartphone having an installed app) in communication (e.g., wireless communication) with each other. In some cases, the remote user-interface device can serve as the primary user interface for interacting with the medication delivery device, but the medication delivery device can be adapted to provide audible, visual, or haptic feedback under certain conditions. In some cases, methods, devices, and systems provided herein can have a controller in the medication delivery device detect an alarm or alert condition and send a wireless communication intended for a remote user-interface device prior to issuing an alarm or alert on the medication delivery device. In some cases, methods, devices, and systems provided herein can include a controller in the medication delivery device adapted to receive and a remote user-interface device adapted to send a wireless communication indicating that a user has acknowledged an alarm or alert condition. In some cases, methods, devices, and systems provided herein can include a controller in the medication delivery device adapted to cause the medication delivery device to provide an audible, visual, and/or haptic alarm or alert if the controller does not receive a user acknowledgement within a predetermined period of time after sending the wireless communication, which can ensure that the user is able to receive communications from the remote user-interface device. For example, in some cases, a remote user-interface device can be programmed by the user to not provide audible alarms, or the remote user-interface device may be too far away from the medication delivery device or may have a depleted battery. In some cases, the user acknowledgement can come to the controller via a wireless communication from the remote user-interface device or via user interaction with the medication delivery device.

Devices, methods, and systems provided herein can permit a user to stop or quiet an alarm or alert on the remote user-interface device and/or the medication delivery device by pressing one or more appropriate keys or user-selectable icons on the remote user-interface device (e.g., a snooze button) or the medication delivery device, or taking some other interactive action with the remote user-interface device and/or the medication delivery device (e.g., moving the remote user-interface device in a predetermined motion or series of motions). After an alarm or alert is stopped, in some cases, a controller in the medication delivery device may wait a predetermined snooze period of time before re-triggering an alarm or alert by sending a wireless communication intended for the remote user-interface device for the same alarm or alert condition. In some cases, a user will take appropriate action so that the alarm or alert condition is resolved or resolving such that the alarm or alert condition will not be present after the snooze period. In some cases, different alarm or alert conditions will have different predetermined periods of time based on a danger associated with the alarm or alert condition. In some cases, each alarm or alert condition will have the same predetermined periods of time regardless of the danger associated with the alarm or alert condition. For example, in some cases, an alarm for severe hypoglycemia may only be snoozed for a limited amount of time (e.g., between 5 and 10 minutes), while an alarm for hypoglycemia may be snoozed for a relatively longer period of time (e.g., between 15 and 30 minutes). In some cases, a user can snooze and/or acknowledge an alarm or alert condition via a button on the housing of the medication delivery device. In some cases, medication delivery devices provided herein can include a tap detector and/or a proximity sensor and a user can snooze and/or acknowledge an alarm or alert condition by tapping on the housing of the medication delivery device and/or by motioning ((e.g., with the user's hand) within a selected proximity of the delivery device). In some cases, medication delivery devices provided herein will only recognize an acknowledgement via the medication delivery device if there is a predetermined number or pattern of taps, button pushes, or gestures, which can prevent inadvertent button presses or jostling of the medication delivery device from silencing an important alarm. In some cases, alarms or alerts on either the medication delivery device, the remote user-interface device, and/or another remote device can be acknowledged/silenced from one or more of the devices. For example, in some cases a user may hear an audible tone from their remote user-interface device and wish to silence it via quick button press or tap on the medication delivery device even before any audible, visual, or haptic alarm or alert is issued on the medication delivery device. In such cases, the controller in the medication delivery device can send a wireless communication of the acknowledgement to the remote user-interface device to stop the alarm tone. In some cases, the snooze period can depend on the type of alarm or alert. In cases, the snooze period can be the same length of time for all alarm or alert conditions. In some cases, the snooze period can be for a selected period of time, for example, between about 5 minutes and about 30 minutes, between about 10 minutes and about 20 minutes, or about 15 minutes.

A remote user-interface device of systems and methods provided herein can be an intended primary user interface, to provide users with the convenience and discretion offered by the use of remote user-interface devices, such as the user's smartphone. In some cases, methods and systems provided herein can limit the ability of a user to control the medication delivery device without the presence of the remote user-interface device. For example, in some cases, a user will not be able to instruct the medication delivery device to deliver additional medication (e.g., a bolus of medication) without the remote user-interface device. In some cases, the primary user interface can be an application downloadable onto a user's smartphone and adapted to be paired to the medication delivery devices provided herein. Restricting the ability of a user to control the medication delivery device directly may seem counter-intuitive, but redirecting the user's attention to a remote user-interface device can conserve the power supply in the medication delivery device by reducing the power needed to power a robust user interface, as the medication delivery device may be a medication infusion device, intended to be worn on the user's body to provide regular, near continuous, or continuous delivery of medication to the user based on the user's needs, which can make the recharging of a battery in the medication delivery device inconvenient to a user. Remote user-interface devices, such as a smartphone, however, can be more convenient to recharge, and thus can be used to provide better graphics, better sound, and a more intuitive user experience. Additionally, a more robust user experience provided on a remote user-interface device can reduce the opportunity for a user to make a mistake in the delivery of medication. Also, a remote user-interface device can permit users to check the status of a medication delivery system provided herein without needing to directly access their medication delivery devices.

In some cases, methods, devices, and systems provided herein can additionally include an analyte sensor. For example, in some cases, an insulin delivery system can include a continuous glucose monitor. In some cases, an analyte sensor can be in wireless communication with the medication delivery device and/or the remote user-interface device. In other cases, an analyte sensor can be part of a medication delivery device. In some cases, medication delivery methods, devices, and systems provided herein can automate the delivery of medication to the user based on data from one or more analyte sensors. Automating medication delivery based on feedback from an analyte sensor, however, is only possible if the analyte sensor is providing actionable data. Accordingly, in some cases, methods, devices, and systems provided herein can include a medication delivery device having multiple modes of operation including at least one automation mode (e.g., where medication dosages or rates are changed depending at least in part on data from the analyte sensor) and at least one non-automation mode (e.g., where medication is delivered according to a programmed rate or dosage schedule). Accordingly, medication delivery methods, devices, and systems provided herein can include a medication delivery device adapted to inform the user regarding a current mode of operation even without the presence of the remote user-interface device. For example, in the case of a person with diabetes (PWD) using an insulin delivery system having an automated mode that changes basal rates based on data from a continuous glucose monitor (CGM) and a mode that simply delivers according to a schedule, the PWD may want to be more cognizant of their blood glucose levels if that PWD knows that the system is not actively adjusting basal rates based on CGM data. Additionally, methods, devices, and systems provided herein can be configured to indicate whether actionable data from the CGM is being received by the medication delivery device on the medication delivery device. In some cases, a housing of the medication delivery device can include a light that indicates the current mode of the medication delivery device. In some cases, the light can be adjacent to a mode icon or can illuminate a mode icon.

In some cases, methods, devices, and systems provided herein can alert the user to a need to take additional action to correct for an analyte condition based on data from an analyte sensor. For example, in some cases, an insulin delivery system provided herein in wireless communication with a continuous glucose monitor can provide a PWD with a notice regarding a need to correct a current or anticipated hypoglycemic condition by consuming carbohydrates or a notice regarding a need to administer additional insulin to correct a current or anticipated hyperglycemic condition. In some cases, methods, devices, and systems provided herein may include a user interface on the medication delivery device that does not provide a specific or relative analyte concentration, but instead simply provides an indication regarding a recommended corrective action. In other cases, methods, devices, and systems provided herein can provide a generalized indication of whether the user has a high or low analyte concentration, but not display a specific concentration. In either case, methods and systems provided herein can permit the user to see more specific analyte sensor data, such as specific concentrations, by accessing the remote user-interface device. By limiting the ability of the medication delivery device to display specific analyte sensor data, medication delivery methods and systems provided herein can ensure that the remote user-interface device remains the primary user interface, yet ensure that a user is alerted to safety concerns in a timely manner so that the user can take appropriate corrective action. Additional information that may be displayed on the medication delivery device may include an indication that the amount of medication in the medication delivery device is below a threshold or completely depleted, an indication that an amount of power remaining in a battery in the medication delivery device is below a threshold, an indication that the fluid path for the medication is occluded, or an indication that a message is awaiting the user on the remote user-interface device.

In some cases, methods and systems provided herein can have icons on the medication delivery device that match icons used in the remote user-interface device for communicating alarm or alert conditions. Having matching icons on the medication delivery device and on the remote user-interface device can reinforce the meaning behind these icons as the user uses the system. Additionally, matching icons may provide a user with a more robust explanation of an icon at the remote user-interface device.

In some cases, a remote user-interface device can be adapted to permit the user to enter contextual information regarding the user (e.g., about their condition, about their physical attributes, etc.), and the remote user-interface device can wirelessly communicate the contextual information to a controller in the medication delivery device for use in automating the delivery of medication to the user when in an automated mode. For example, in the case of a person with diabetes (PWD) using an insulin delivery system provided herein, the remote user-interface device can be configured to permit the PWD to enter a meal (e.g., enter an amount of carbohydrates consumed by the PWD). In some cases, a PWD can issue a command for the insulin delivery device to deliver a bolus of insulin for a meal. In some cases, insulin delivery methods and systems provided herein can include a remote user-interface device adapted to permit a user to enter exercise, sickness, menses, other medications (e.g., acetaminophen), exogenous insulin, or any other condition that may impact blood glucose levels or the validity of glucose sensor data. In some cases, medication delivery devices provided herein may not permit the entry of such contextual information, which can reinforce the use of the remote user-interface device as the primary user interface.

Medication delivery devices provided herein can include the controller that determines an amount of medication to deliver, rather than merely being directed to deliver certain amounts of medication by a controller on a remote device, in order to minimize missed or inappropriate medication deliveries due to a faulty wireless connection between components of systems provided herein. Accordingly, in some cases, systems and methods provided herein can have a controller in the medication delivery device be the center of an on-body network and the source of truth such that any inconsistencies or conflicting instructions are resolved based on the controller in the medication delivery device. In some cases, a medication delivery device can include a programmed schedule of medication deliveries or rates and/or other user-specific dosage parameters that determine appropriate dosages of medication. In some cases, the controller in the medication delivery device can update or personalize these schedules and/or dosage parameters over time and send these updated schedules and/or dosage parameters to the remote user-interface device for viewing or use by the user. In some cases, a medication delivery device receiving a command to deliver a bolus of medication can double check the command to see if the dosage is appropriate and/or safe for the user and/or whether the remote user-interface device may have used the wrong schedule or dosage parameters in making a recommendation to the user based on user entered data. In some cases, methods, devices, and systems provided herein may require a user to confirm a desire to deliver a bolus by pushing a button or tapping the medication delivery device under certain conditions. For example, in an insulin delivery system provided herein, a user entering an extremely large meal bolus for that user, or entering multiple bolus amounts within a short period of time, may be required to confirm the bolus by pressing the button or tapping on the housing of the insulin delivery device.

Medication delivery devices provided herein can include a sound emitter adapted to play one or more alarm or alert tones, a vibration motor, and/or one or more indicator lights and/or illuminable icons, where the sound emitter, vibration motor, indicator lights or icons, or any combinations thereof are adapted to indicate whether the medication delivery device is delivering medication, whether a medication delivery rate or amount is being determined at least in part on real-time data from the analyte sensor, whether real-time data is available to the medication delivery device, whether the medication delivery device is low or out of medication, whether the medication delivery device is low on power, and/or whether a message is awaiting the user on the remote user-interface device. In some cases, the medication delivery device can be an insulin pump having a sound emitter, a vibration motor, indicator lights and/or icons, or any combinations thereof and can be adapted to indicate that the user needs to consume a meal and/or that the user should administer a bolus. For example, in some cases, a predictive algorithm in an insulin pump can predict a dangerously low blood glucose level that will not be corrected by suspending insulin delivery, and thus the insulin pump provided herein can indicate to the user that the user should consume carbohydrates. In some cases, an insulin pump provided herein can predict that a maximum administration of basal insulin allowed by the programming of the pump will not return the user to a target blood glucose value or range within a predetermined amount of time, and thus the insulin pump provided herein can indicate that the user should administer a corrective bolus. In some cases, an insulin pump provided herein may use data from a continuous glucose monitor to detect a possible meal that was not accompanied by a bolus, and may indicate that the user should administer a bolus.

In some cases, methods, systems, and devices provided herein can include a button on the medication delivery device, which can be used, in addition to acknowledging/snoozing alarms and alerts, to check the status of the medication delivery device (e.g., check to see if it is delivering medication, a current mode, and see if there are any outstanding messages). For example, if a user wishes to know the current mode of the medication delivery device, the user can double press the button, and an indication light or icon can illuminate to indicate the current mode of operation (e.g., automated mode or non-automated mode). In some cases, additional icons may illuminate or flash to indicate other conditions or messages awaiting the user on the remote user-interface device. For example, if an amount of medication remaining is below an alert threshold level, but not below an alarm threshold level (e.g., at a level where corrective action may be advisable, but not necessary), pressing the button may cause a message icon to light and/or for an insulin depleted or low icon to flash. In some cases, in order for a user to know that all of the lights or illuminable icons are working properly, certain conditions may cause all of the lights to flash on (e.g., an instruction from the remote user-interface device during a systems check process or whenever medication delivery device receives a new supply of medication). Moreover, the lights or illuminable icons can flash when a user acknowledges or snoozes an alarm using the medication delivery device. Additionally or alternatively, a tap detector can be used to detect a desire from the user to see the system status on the medication delivery device. In some cases, a tap detecting device can be an accelerometer.

In some cases, methods, systems, and devices provided herein can provide audible, visual, and/or haptic alarms via an analyte sensor worn by the user, which can be in addition to or instead of the alarms or alerts provided by the medication delivery device.

One or more cases of the present disclosure may include an on-body networked medication-delivery system. Such a system may include an analyte sensor adapted to generate analyte data for a user and wirelessly transmit the analyte data, and a medication delivery device in wireless communication with the analyte sensor. The medication delivery device can include a medication reservoir or a space to receive a medication reservoir, a drive system adapted to meter the administration of medication out of the medication delivery device, and a feedback feature or features to provide audible, visual, or haptic feedback to a user. The medication delivery device can include a controller adapted to change a dosage of medication based at least in part on the analyte sensor data and can be adapted to issue alarm and alert wireless communications based on a detection of an alarm or alert condition, and a tap detector or button adapted to permit the user to check the status of the medication delivery device or to acknowledge the alert or alarm conditions. The on-body networked medication-delivery system can include a remote user-interface device in wireless communication with the medication delivery device. The remote user-interface device can be adapted to receive the alarm and alert wireless communications from the controller and provide an audible, visual, or haptic alarm or alert message to the user and can permit the user to acknowledge an associated alarm or alert condition. In some cases, the remote user-interface device can be adapted to wirelessly communicate each acknowledgement to the controller. In some cases, the controller can be adapted to trigger an audible, visual, or haptic alarm or alert message via the feedback feature to provide audible, visual, or haptic feedback if the controller fails to receive an acknowledgement of the alert or alarm condition within a predetermined period of time after the controller issues the alarm and alert wireless communication.

In one or more methods, systems, or devices of the present disclosure, the system can be a diabetes management system, and the medication delivery device can be an insulin pump, and the analyte sensor can be a continuous glucose monitor.

In one or more methods, systems, or devices, of the present disclosure, the medication delivery device can be a patch pump.

In one or more methods, systems, or devices, of the present disclosure, the medication delivery device can be an insulin pen or pens.

In one or more methods, systems, or devices of the present disclosure, the medication delivery device can include a durable controller and a disposable pump body, each having a housing and being removably connectable. In such cases, the disposable pump body can include at least the medication reservoir or a space to receive a medication reservoir and the durable controller can include at least the feature to provide audible, visual, or haptic feedback, the controller, and the tap detector or button.

In one or more methods, systems, or devices of the present disclosure, the medication delivery device can include a button.

In one or more methods, systems, or devices of the present disclosure, the feature(s) to provide audible, visual, or haptic feedback to a user can include at least one light associated with an icon.

In one or more methods, systems, or devices of the present disclosure, the remote user-interface device can be adapted to present the icon for an alarm or alert condition.

In one or more methods, systems, or devices, of the present disclosure, the at least one light associated with the icon may not illuminate on the housing until the tap detector detects a tap, or the button is pressed, or until the predetermined period of time.

In one or more methods, systems, or devices of the present disclosure, a user can acknowledge an audible, visual, or haptic alarm or alert message provided by a remote user-interface device by tapping the medication delivery device or pressing the button on the medication delivery device even before the medication delivery device triggers the audible, visual, or haptic alarm or alert message via the feature(s) to provide audible, visual, or haptic feedback.

In one or more methods, systems, or devices of the present disclosure, feature(s) to provide audible, visual, or haptic feedback can include a vibration motor adapted to provide haptic feedback, and the controller can be adapted to provide haptic feedback or audible feedback, upon issuing the alarm and alert wireless communications. Additionally, the audible alarm or alert message that can be triggered if the controller fails to receive an acknowledgement of the alert or alarm condition within a predetermined period of time can be louder or longer in duration than the haptic feedback or audible feedback provided when the controller issues the alarm and alert wireless communications.

In one or more methods, systems, or devices of the present disclosure, the predetermined period of time can be at least 30 seconds and no greater than 1 hour, between 1 minute and 30 minutes, between 3 minutes and 20 minutes, or between 5 minutes and 15 minutes, and the predetermined period of time for an alarm or alert condition can depend on the alarm or alert condition.

In one or more methods, systems, or devices of the present disclosure, an acknowledgement of an alarm or alert may quiet audible or haptic feedback for the alarm or alert condition for a predetermined snooze period of time, and the controller can be adapted to issue new alarm and alert wireless communications after the predetermined snooze period of time if the alarm or alert condition is still detected as being present.

In one or more methods, systems, or devices of the present disclosure, the remote user-interface device can be adapted to present the user with troubleshooting instructions using text, audio, or video to remove the alarm or alert condition, and the medication delivery device may not present any troubleshooting instructions using text, audio, or video.

In one or more methods, systems, or devices of the present disclosure, the medication delivery device can include a housing that contains a non-rechargeable, non-replaceable battery.

In one or more methods, systems, or devices of the present disclosure, the remote user-interface device can be adapted to allow a user to send instructions to the medication delivery device using the remote user-interface device, and the remote user-interface device can prompt the user to confirm the instructions by pressing the button or tapping the controller under certain conditions.

In one or more methods, systems, or devices of the present disclosure, the controller can be adapted to require a user to confirm a bolus delivery by pressing the button or tapping the controller if the dosage is determined by the controller to be unusual based on typical dosage amounts administered by the user, based on the timing the dosage or the timing of a previous dosage, or based on a prediction of how the dosage will change analyte levels for the user.

In one or more methods, systems, or devices of the present disclosure, the medication delivery device can include one or more icons, and one or more lights associated with those one or more icons, indicating whether the medication is being delivered based on the analyte sensor or not or whether there is an error with the analyte sensor.

In one or more methods, systems, or devices of the present disclosure, the medication delivery device can include one or more icons, and one or more lights associated with those one or more icons, indicating that an amount of medication in the medication delivery device is below a threshold level.

In one or more methods, systems, or devices of the present disclosure, the medication delivery device can include one or more icons, and one or more lights associated with those one or more icons, indicating that the user should administer more medication or consume carbohydrates.

In one or more methods, systems, or devices of the present disclosure, the medication delivery device can include one or more icons, and one or more lights associated with those one or more icons, indicating that a more detailed message for the user is awaiting the user on the remote user-interface device.

One or more cases of the present disclosure can include a method for issuing alarms and alerts in an on-body networked diabetes management system. The method can include receiving glucose sensor data from a continuous glucose monitor, and determining a dosage of insulin delivery based at least in part on the glucose sensor data. The method can include detecting an alarm or alert condition, and sending a wireless communication regarding the alarm or alert condition to a remote user-interface device. The method can additionally include triggering an audible, visual, or haptic alarm or alert on the insulin delivery device if the insulin delivery device does not receive an acknowledgement of the alarm or alert condition within a predetermined period of time.

In one or more methods, systems, or devices of the present disclosure, the user can acknowledge the alarm by pressing a button on the insulin delivery device or by tapping the insulin delivery device and by interacting with the remote user-interface device, and the insulin delivery device can receive an acknowledgement of the alarm or alert condition as part of a wireless communication from the remote user-interface device.

In one or more methods, systems, or devices of the present disclosure, such a method can include triggering audible or haptic feedback of the insulin delivery device when sending the wireless communication regarding the alarm or alert condition to the remote user-interface device, and the audible, visual, or haptic alarm or alert on the insulin delivery device after the predetermined period of time can be louder or longer in duration than the feedback initiated when sending the wireless communication.

In one or more methods, systems, or devices of the present disclosure, such a method can include stopping the audible, visual, or haptic alarm or alert on the insulin delivery device when a button on the insulin delivery device is pressed.

In one or more methods, systems, or devices of the present disclosure, the button must be pressed at least twice during a predetermined period of time or according to a predetermined pattern for the audible, visual, or haptic alarm or alert to be stopped.

In one or more methods, systems, or devices of the present disclosure, stopping the audible, visual, or haptic alarm or alert on the insulin delivery device can prevent the triggering of any audible, visual, or haptic alarms or alerts regarding that alarm or alert condition or the sending of any wireless communication regarding the alarm or alert condition for a predetermined period of time. Additionally, one or more methods or processes of the present disclosure can repeat after the predetermined period of time if the alarm or alert condition is present after the predetermined period of time.

In one or more methods, systems, or devices of the present disclosure, the alarm or alert condition can indicate a change from a first mode of operation to a second mode of operation.

In one or more methods, systems, or devices of the present disclosure, the alarm or alert condition can be an indication of an amount of insulin remaining in the insulin delivery device being below a threshold level.

In one or more methods, systems, or devices of the present disclosure, the alarm or alert condition can be an indication of a low glucose condition or a high glucose condition.

In one or more methods, systems, or devices of the present disclosure, the audible, visual, haptic alarm or alert on the insulin delivery device can include the illumination of an icon or next to an icon indicating that the user should eat or should administer insulin.

In one or more methods, systems, or devices of the present disclosure, the alarm or alert condition can be a notice that the continuous glucose monitor is not working, not in range, or not reliable.

In one or more methods, systems, or devices of the present disclosure, the alarm or alert condition can be a notice about a possible occlusion, a possible air bubble, a possible missed meal announcement, a possible need to change an infusion set, a possible need to calibrate a CGM, a possible need to replace the CGM, or a possible need to check ketone levels, and the audible, visual, haptic alarm or alert on the insulin delivery device can include the illumination of an icon or next to an icon indicating that the user should check the remote user-interface device for information about the alert.

One or more cases of the present disclosure can include an insulin delivery device adapted for wireless communication with a continuous glucose monitor and a remote user-interface device. The insulin delivery device can include an insulin reservoir or a space to receive an insulin reservoir, and a drive system adapted to meter the administration of insulin out of the insulin delivery device. The insulin delivery device can include a wireless transmitter and receiver adapted to send and receive wireless communications from at least a continuous glucose monitor and a remote user-interface device, and a controller adapted to change a dosage of medication based at least in part on data from the continuous glucose monitor and adapted to issue alarm and alert wireless communications based on a detection of an alarm or alert condition. The insulin delivery device can additionally include a housing containing at least the controller and the wireless transmitter and receiver, a tap detector within the housing or a button on the housing adapted to permit the user to check the status of the insulin delivery device or to acknowledge alert or alarm conditions, and one or more lights adapted to illuminate icons or adjacent to icons on the housing indicating a mode of operation of the insulin delivery device and whether insulin is being delivered to the user.

In one or more methods, systems, or devices of the present disclosure, an insulin delivery device can include one or more lights or another visual or audio cue adapted to illuminate icons or adjacent to icons on the housing indicating that a message is awaiting the user on the remote user-interface device.

In one or more methods, systems, or devices of the present disclosure, an insulin delivery device can include one or more lights adapted to illuminate icons or adjacent to icons on the housing indicating that the user has a blood glucose condition requiring the consumption of carbohydrates or the administration of additional insulin.

In one or more methods, systems, or devices of the present disclosure, the user cannot administer additional insulin using the insulin delivery device without accessing the remote user-interface device.

In one or more methods, systems, or devices of the present disclosure, the controller can be adapted to evaluate whether a wireless communication from a remote user-interface device is within one or more predefined parameters.

In one or more methods, systems, or devices of the present disclosure, the controller can be adapted to send a wireless communication to the remote user-interface device indicating that a bolus is outside of one or more predefined parameters, or indicating the user must confirm the bolus on the insulin delivery device by tapping or pressing the button.

In one or more methods, systems, or devices of the present disclosure, an insulin delivery device can include one or more lights adapted to illuminate icons or adjacent to icons on the housing indicating that there is a problem with the data being received, or a lack of data being received, from the continuous glucose monitor.

One or more cases of the present disclosure can include a medication delivery system that includes a medication delivery device and a remote user-interface device, where the medication delivery device and the remote user-interface device can be in wireless communication. The medication delivery device can be adapted to automatically administer medication according to a programmed rate, a programmed schedule, or based on analyte sensor data without user input. The remote user-interface device can be adapted to receive user commands for the medication delivery device to administer additional doses of medication, adjust the programmed delivery rate or schedule, or adjust an algorithm that determines a dosage based on the analyte sensor data. Additionally, both the remote user-interface device and the medication delivery device can be adapted to provide audible, visual, or haptic feedback to issue an alarm or alert regarding the ability of the medication delivery device to deliver medication. The medication delivery device can be adapted to detect a condition that prevents the delivery of medication and send an alarm wireless communication to the remote user-interface device regarding the condition. The remote user-interface device can issue an audible, visual, or haptic alarm when the alarm wireless communication is received, and can provide a feature for the user to acknowledge the alarm. The remote user-interface device can send an acknowledgement wireless communication to the medication delivery device upon the user acknowledging the alarm, and the medication delivery device can be adapted to issue an audible, visual, or haptic alarm after a predetermined period of time after the alarm wireless communication is sent unless the medication delivery device receives the acknowledgement wireless communication during the predetermined period of time.

In one or more methods, systems, or devices of the present disclosure, the medication delivery device can include a feature to receive a user's acknowledgement an audible, visual, or haptic alarm to silence the alarm.

In one or more methods, systems, or devices of the present disclosure, the medication delivery device can include an insulin infusion pump, the medication can be insulin, and the remote user-interface device can be a smartphone.

In one or more methods, systems, or devices of the present disclosure, such a system can include a continuous glucose monitor in wireless communication with the insulin infusion pump, and the insulin infusion pump can deliver different amounts or rates of insulin based on glucose data from the continuous glucose monitor.

In one or more methods, systems, or devices of the present disclosure, the insulin infusion pump may not be adapted to display specific concentrations of the glucose data, but can be adapted to send glucose data wireless communications to the smartphone, and the smartphone can be adapted to display specific concentrations of the glucose data.

In one or more methods, systems, or devices of the present disclosure, the insulin infusion pump can be adapted to illuminate one or more icons, or a light next to one or more icons, that indicate that the user is in or expected to experience hypoglycemic state or a hyperglycemic state, that indicate that the user should administer more insulin, or that indicate that the user should consume food, and that light can become illuminated when the insulin infusion pump issues an issue an audible, visual, or haptic alarm or when the user acknowledges the alarm on the insulin infusion pump.

In one or more methods, systems, or devices of the present disclosure, the insulin infusion pump can be adapted to illuminate one or more icons, or a light next to one or more icons, that indicate that the user is in out of insulin, wherein the light becomes illuminated when the insulin infusion pump issues an issue an audible, visual, or haptic alarm or when the user acknowledges the alarm on the insulin infusion pump.

The details of one or more implementations of the disclosure are set forth in the accompanying drawings and the description below. Other features, objects, and advantages of the disclosure will be apparent from the description and drawings, and from the claims.

DESCRIPTION OF DRAWINGS

FIGS. 5A-5C depict example alarms for a lack of insulin flowing in an insulin delivery system provided herein. FIG. 5A depicts a visual indication for the alarm on an insulin delivery device. FIGS. 5B and 5C depict a visual indication for the alarm on a remote user-interface device.

FIGS. 15A-15C illustrate how example notification lights on an automated medication infusion pump can inform a user about the status of the medication delivery system.

FIGS. 16A and 16B illustrate example alarms and how a user can snooze the alarms.

Like reference symbols in the various drawings may indicate like elements.

DETAILED DESCRIPTION

Methods, devices, and systems provided herein can be used to deliver any appropriate medication for the treatment of any appropriate disease or condition. The embodiments described below relate to an insulin delivery system for the management of diabetes, however, the delivery of other types of medications for other diseases are also contemplated. For example, in addition to diabetes, methods, devices, and systems provided herein can be used to treat unresponsive infections, cancer, cancer-related pain, chronic pain, gastrointestinal diseases or disorders, congestive heart failure, hemophilia, immune deficiencies, multiple sclerosis, and rheumatoid arthritis. In some cases, methods, devices, and systems provided herein can use analyte sensor data to automate the delivery of medication. Although the example embodiments described below are specific to an insulin delivery device adapted to automate basal insulin deliveries based on data from a continuous glucose monitor, medication delivery systems that do not include and/or consider data from an analyte sensor are also contemplated.

As used herein, the term "substantially" in reference to a given parameter feature(s) and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

Figure 1A:
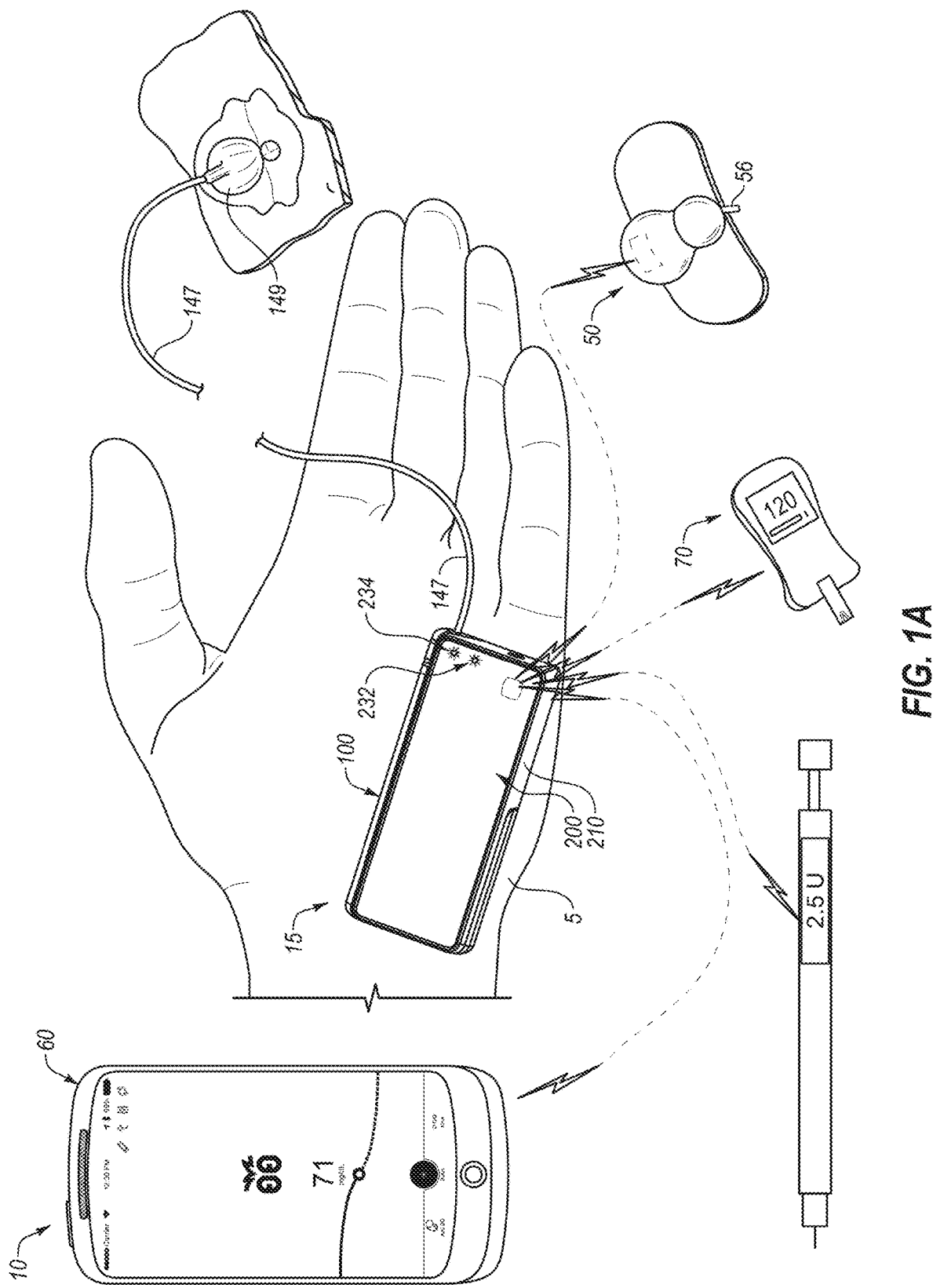
FIG. 1A is a perspective view of a first example medication delivery system including a module medication delivery device, at least one analyte sensor, and a remote user-interface device.

FIG. 1A depicts an example medication delivery system provided herein, which includes at least a medication delivery device 15 and a remote user-interface device 10. As shown, the medication delivery device 15 is an insulin delivery device, more specifically an insulin infusion pump. As shown, the medication delivery device 15 can be sized to fit within an adult human's hand 5. In some embodiments, the medication delivery system depicted in FIG. 1A may be similar to or the same as that disclosed in U.S. Patent Application Publication No. US 2017/0203037 A1, published Jul. 20, 2017, the disclosure of which is hereby incorporated herein in its entirety by this reference.

FIG. 1A further depicts analyte sensor 50, which are shown as both being in wireless communication with the medication delivery device 15. Analyte sensor 50 can be a continuous glucose monitor (CGM, and may be referred to as CGM 50) adapted to have a sensor probe 56 sit subcutaneously on a user's skin and provide regular (e.g., every 1 minute, every 3 minutes, every 5 minutes, every 10 minutes, every 30 minutes, or at some interval in between) or irregular (e.g., variable depending on one or more previous blood glucose readings) blood glucose readings. The medication delivery device 15 can then use the data from CGM 50 to alter medication dosages or delivery rates. Although the incorporated by reference U.S. Patent Application Publication No. US 2017/0203037 A1 describes certain techniques for changing between basal rates of 0×, 1×, and 2λ (and optionally 3× or other multipliers) of a baseline basal rate, other techniques for using CGM to automate basal insulin delivery rates or provide microboluses of insulin to a user are contemplated and known in the art. In some cases, the medication delivery device 15 can use the CGM data in a proportional-integral (PI) controller, a derivative controller, a proportional-integral-derivative (PID) controller, a model predictive controller, etc. Additionally, as described in the incorporated by reference U.S. Patent Application Publication No. US 2017/0203037 A1, the medication delivery device 15 can have multiple modes, including an automated mode and a non-automated mode (e.g., a personalized mode), which can be entered and exited based on the availability of actionable CGM data (and optionally other conditions) and/or one or more user preferences. Accordingly, the medication delivery device 15 can include indicator lights 232 and 234, which can be used to indicate a mode of operation, and optionally certain error conditions. Additional details about possible indicator lights and arrangements are described below in relationship to FIGS. 2-15.

Figure 1B:
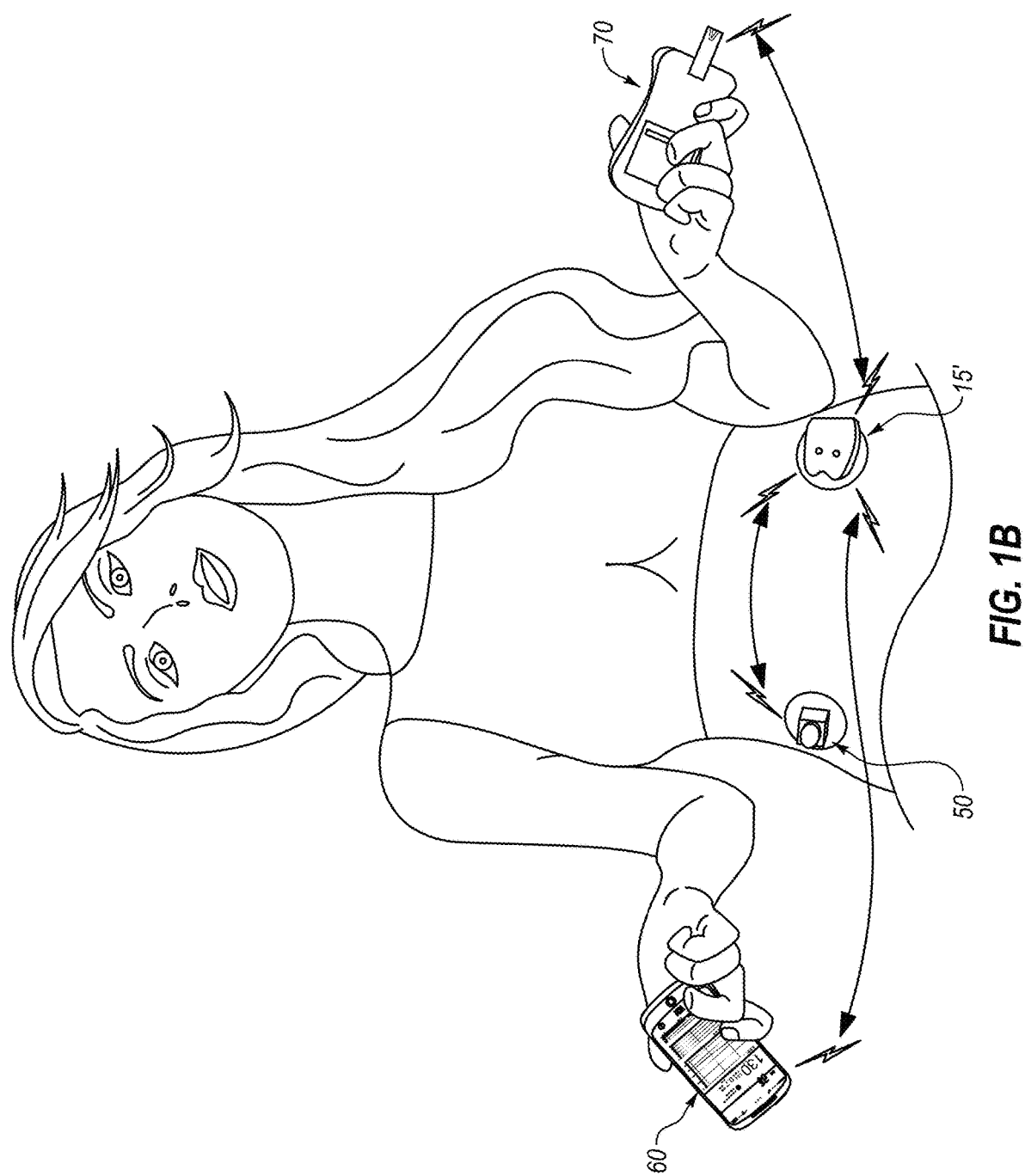
FIG. 1B is a perspective view of a second example medication delivery system including a patch pump-type medication delivery device, at least one sensor, and a remote user-interface device.

FIG. 1B depicts a medication delivery system according to a second embodiment where a medication delivery device is a patch pump 15', which also can be used to deliver insulin in an insulin delivery system and can use CGM data from CGM 50 to automate insulin dosages or rates. As shown, patch pump 15' also includes indicator lights. Although FIGS. 2-15 show a medication delivery device user interface on a medication delivery device similar to that of FIG. 1A, the features shown and described below are equally applicable to patch pumps or other suitable delivery devices. Also as shown, patch pump 15' can include a wireless receiver and transmitter to send and receive wireless communications from a remote user-interface device 60, the CGM 50, and a blood glucose meter 70, and can include a controller adapted to automate insulin based at least in part on CGM data using any appropriate control algorithm.

Figure 2:
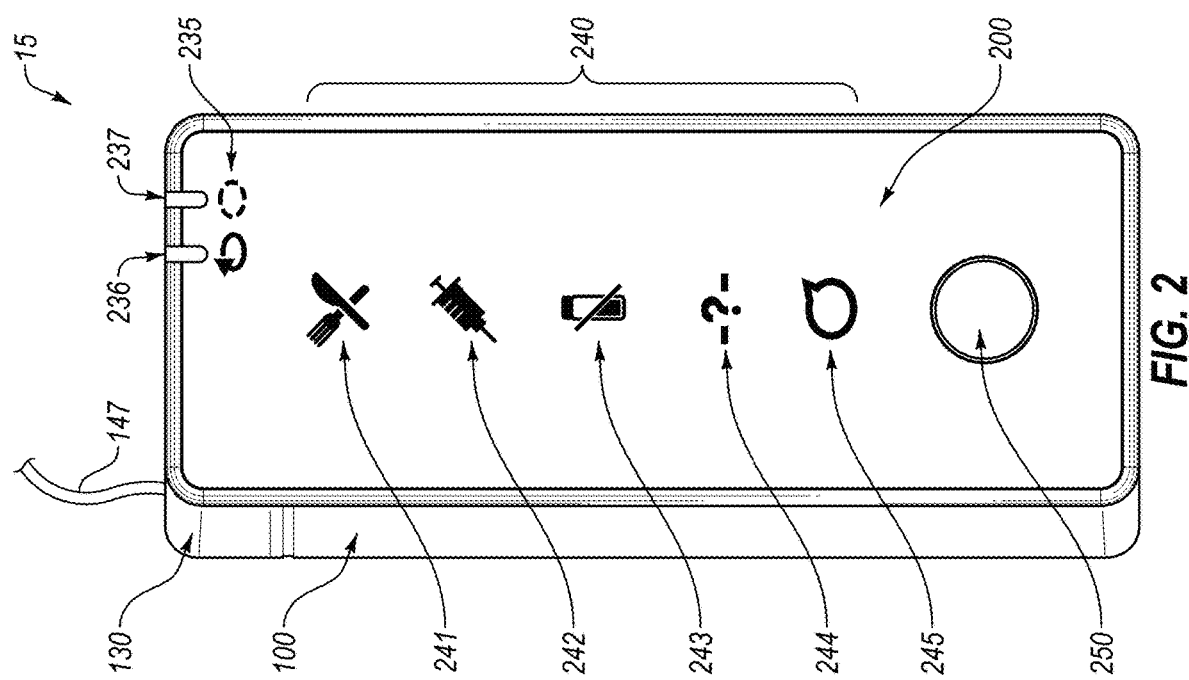
FIG. 2 is an example view of a module medication delivery device showing an example medication delivery device user interface.

FIG. 2 depicts an example user interface for the medication delivery device 15, specifically for an insulin infusion pump. In some cases, the medication delivery device 15 can be a modular medication delivery device including a disposable pump body 100 and a durable controller 200, as described in the incorporated by reference U.S. Patent Application Publication No. US 2017/0203037 A1. However, this user interface can be applied to unitary medication delivery devices, as well as to patch pumps (such as those shown in FIG. 1B) and any other suitable medication delivery device, particularly those used to deliver insulin. As shown, a front face of medication delivery device 15 can include a button 250. In some cases, medication delivery devices provided herein can include only one button. In some cases, medication delivery devices provided herein can have a plurality of buttons. In some cases, medication delivery devices provided herein can only have buttons capable of snoozing, quieting, or acknowledging alarms, alerts, or notifications and for checking the system status.

The user interface can additionally include a plurality of indicator lights and/or illuminable icons. As shown, indicator lights 236 and 237 can be positioned adjacent to icons 235. As shown, lights and icons 235-237 can inform the user whether the user is in an automated (e.g., closed-loop, open-loop, partially closed-loop, etc.) mode or a non-automated (e.g., personalized) mode. The illumination of light 236 indicates an automated mode and the illumination of light 237 indicates a non-automated mode. In some cases, additional mode lights can be used to indicate other modes. In some cases, a single light can be used to indicate a mode (e.g., a color, flashing pattern, or other light characteristic) can be used to indicate the current mode. In some cases, a plurality of alarm or alert illuminable icons 240 can be positioned on the housing to indicate the need for the user to take certain actions. Although the mode lights 236 and 237 are depicted as being adjacent to icons and icons 241-245 being indicated as being illuminable, the opposite is also a contemplated design, and all icons could have an adjacent light or all icons could be illuminable. As shown, illuminable icon 241 is illuminated, while the other icons 242-245 are not illuminated. Illuminable icon 241 represents a need to eat, illuminable icon 242 indicates a need to take insulin, illuminable icon 243 indicates a depletion of insulin in the medication delivery device 15, illuminable icon 244 indicates an error with CGM data, and illuminable icon 245 indicates that a message awaits the user on the remote user-interface device. Although specific icons are depicted, other icons are also contemplated.

Figure 3:
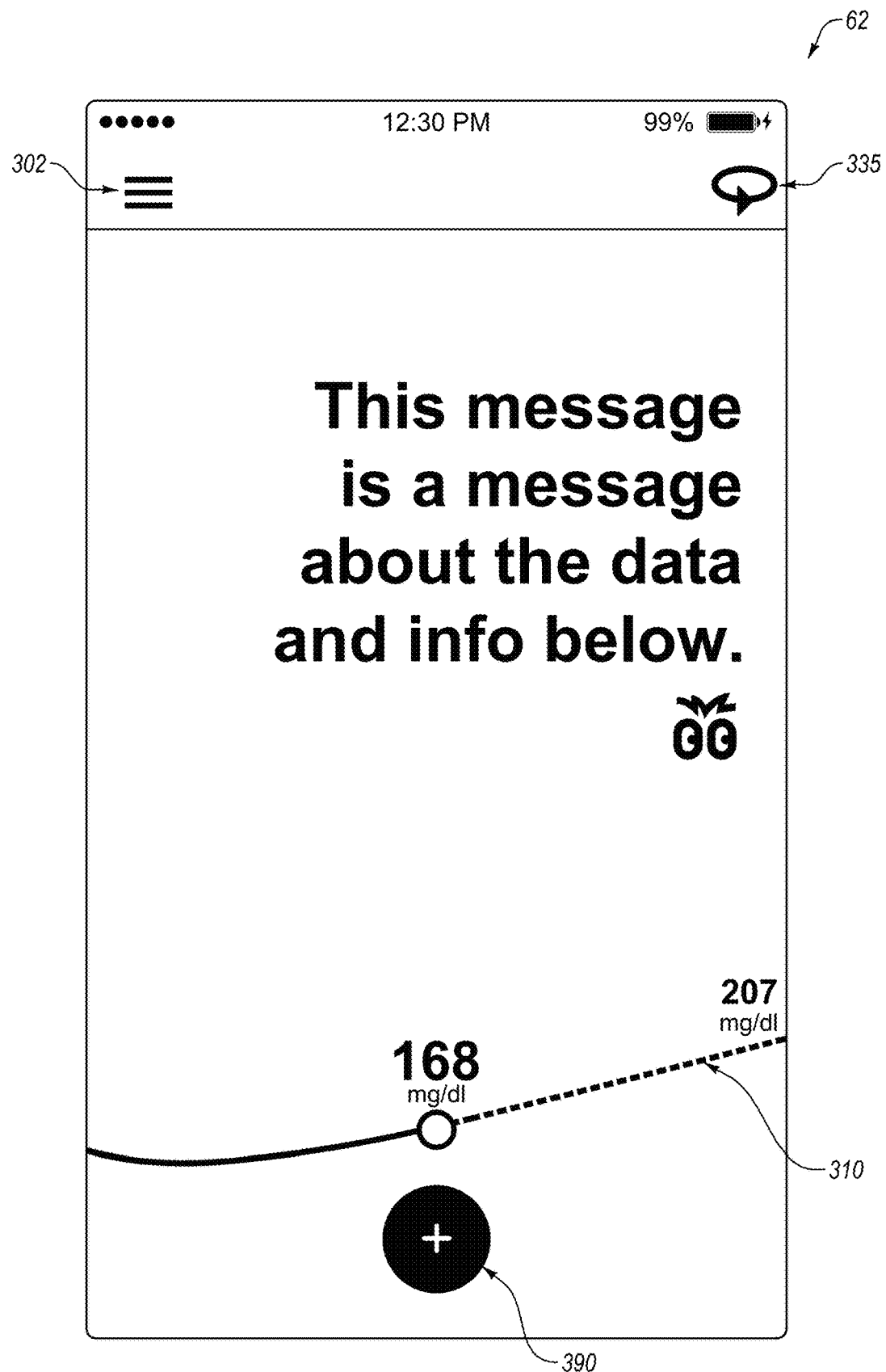
FIG. 3 depicts an example user interface landing home screen for a remote user-interface device.

FIG. 3 depicts an example home landing screen 62 for remote user-interface device 10. As described in the incorporated by reference U.S. Patent Application Publication No. US 2017/0203037 A1 (using a different name), remote user-interface device 10 can be a smartphone or any other suitable remote device having a suitable display and robust data entry capabilities (e.g., a PDA, a tablet computer, a music-playing device). In some cases, the remote user-interface device 10 has an application stored in memory to execute the user interfaces and user experience provided herein. As shown, the remote user interface 60 includes a navigation menu 302, a mode indicator icon 335, a message, blood glucose data display 310 illustrated with a blood glucose value, a blood glucose trend line, and a blood glucose prediction, and a bolus button/user-selectable icon 390. As shown, mode indicator icon 335 can resemble or match an icon 235 on the medication delivery device housing 210, which can reinforce the meaning of the icon. In some cases, if a user taps on the icon in the remote user interface 60, a message can appear explaining the meaning of the icon. If a user taps on the blood glucose data display 310, a message can appear providing an explanation of the display and/or bring the user to a more specific display of blood glucose data and/or insulin delivery data.

Examples of more detailed chart displays of blood glucose data aligned with insulin delivery data are depicted and described in the incorporated by reference U.S. Patent Application Publication No. US 2017/0203037 A1. Navigation menu 302 can be pressed or tapped by the user to access other functions of the remote user-interface device, such as instructional videos on performing certain tasks, entering other contextual information, setting up personal preferences, etc. Bolus button/user-selectable icon 390 can be prominent on the home screen because it can be one of the most important functionalities of the remote user-interface device 10 with respect to controlling the operation of the medication delivery device 15. An additional important function of the remote user-interface device 10 being to provide the user with actionable information regarding alarms, alerts, and other notifications useful for managing/treating diabetes. In some cases, pressing the bolus button 390 can bring the user to a bolus calculator that helps the user determine a bolus based on entered food information, blood glucose data, stored personal dosage parameters (e.g., an insulin sensitivity factor and a carbohydrate-to-insulin ratio), and an estimation of unacted insulin delivered (e.g., insulin on board (IOB)).

Figure 4:
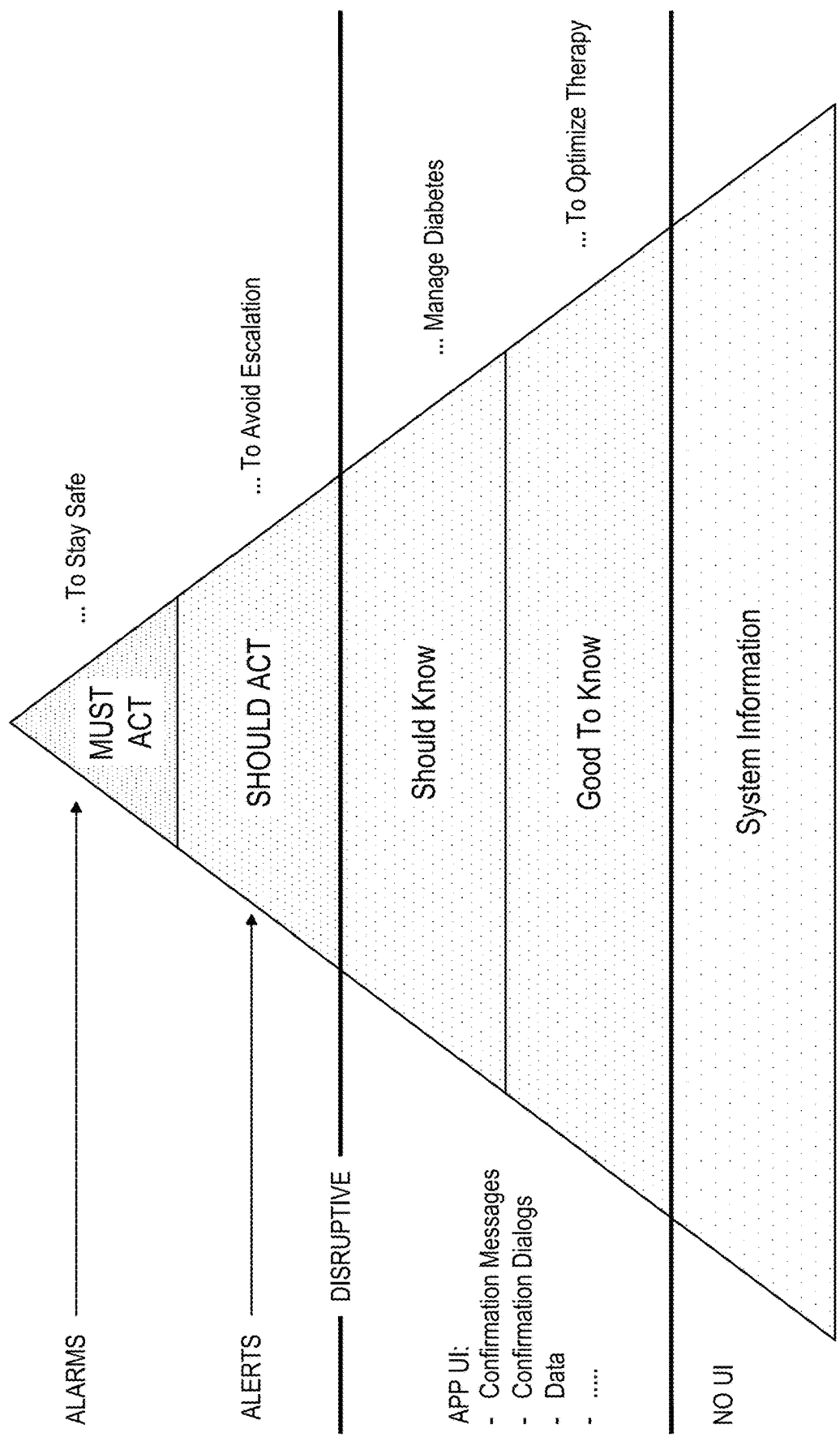
FIG. 4 is an infographic regarding alarms, alerts, and other notices used in a diabetes management system.

FIG. 4 depicts an infographic depicting conceptually a distinction between alarms, alerts, and notifications, as those terms are used in the present disclosure. In some cases, a notification regarding a condition, if not acted upon by a user, can result in that condition triggering an alert or an alarm. In general, an alarm condition is something that requires a user's attention to stay safe, or in other words, a condition that could result in personal injury or other health complications if the condition is not addressed. An example alarm might be triggered by a severe hypoglycemic event. An alarm event might also be triggered if the medication delivery device has a nearly dead battery or is totally depleted of insulin or if there is an occlusion in an infusion catheter 147. In many cases, an alarm condition may typically be avoided if a user takes action based on the triggering of alerts. An alert condition is something that could lead to an alarm condition, or that needs attention. However, an alert condition does not have the same urgency or immediacy as an alarm condition. For example, a predicted hypoglycemic event may trigger a potential hypoglycemic event alert using different threshold criteria than the severe hypoglycemic event condition so that a user can take corrective action before blood glucose levels drop to a level triggering an alarm event. Other possible alerts may include hyperglycemic events, a failure to receive actionable CGM data, a need to calibrate the CGM, an amount of insulin being below a higher alert threshold, and/or a need to conduct system maintenance or replace system components based on their recommended user life. Alarms and alerts should be disruptive to the user because the user should or must act to remain safe, thus methods, systems, and devices provided herein ensure that a user receives prompt notice of these alarm or alert conditions even if the remote user-interface device is not immediately available to the user. The non-disruptive notifications, however, are things that a user can use to better manage or optimize their treatment of diabetes, but are not urgent, thus they can remain accessible upon demand by the user on the remote user-interface device. Such information might be data about past, current, or predicted blood glucose values that are in a safe range, past and current insulin doses and basal delivery rates, previously entered meal sizes, etc. Additionally, there is system information unrelated to the treatment of diabetes, which can be hidden from the user.

FIGS. 5A, 5B, and 5C illustrate how an alarm condition related to a lack of insulin flowing can be displayed on the medication delivery device 15 (FIG. 5A) and on the remote user-interface device (FIGS. 5B and 5C). In each case, the visual indicators shown can be accompanied with an audible alarm tone and/or haptic feedback. As shown, the icon 243 for this alarm condition on the medication delivery device 15 matches an icon 343 displayed on the remote user-interface device (FIGS. 5B and 5C). As shown in FIG. 5B, an alarm notification box 360 can pop up when the user accesses an app on a smartphone. By pressing snooze button 350, the user can stop the audible alarm tone and/or haptic feedback. Similarly, by pressing button 250 on medication delivery device 15, any audible alarm tone sounding from the medication delivery device 15 can be stopped. In some cases, pressing button 250 can result in the medication delivery device 15 sending a wireless communication to remote user-interface device 10 to stop an audible alarm tones or haptic feedback, and vice-versa regarding using button 350 to stop alarm tones and haptic feedback on the medication delivery device. Regarding FIG. 5A, illuminating icon 243 can in some cases be illuminated as soon as audible and/or haptic alarming occurs on the medication delivery device 15, or can be illuminated at the point in time when the user presses button 250 to silence the audible/haptic alarm to show the user the reason for the alarm. In either case, illuminating icon 243 can remain illuminated after snoozing the alarm for at least a predetermined period of time (e.g., between 1 second and 5 minutes, or between 2 seconds and 1 minute, or between 5 seconds and 30 seconds). Referring back to FIG. 5B, alarm notification box 360 can appear over the home landing screen of the remote user-interface device, but can appear over other screens of the user interface.

Figure 6:
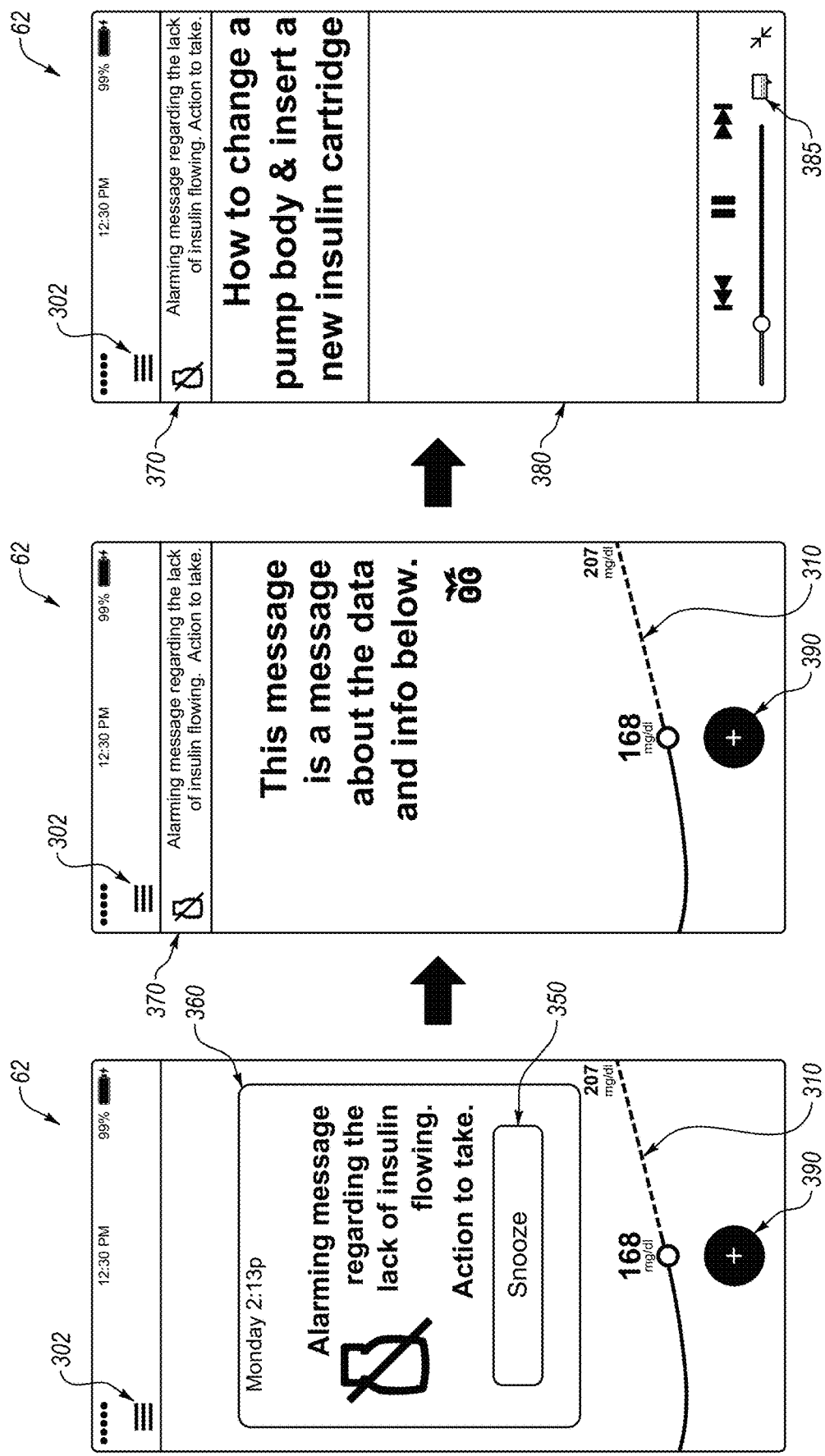
FIG. 6 depicts an example of how the alarms of FIGS. 5A-5C can progress on the remote user-interface device to a tutorial on how to resolve the alarm condition.

As shown in FIG. 6, after an alarm is snoozed by pressing button 350 on the user interface of remote user-interface device 10, the alarm notification box may become an alarm notification banner, still retaining the same icon 343. In some cases, a user may click on this banner 370 to find out additional information about how to resolve the alarm condition (as indicated in FIG. 6). FIG. 6 shows the flow of where a user may push or tap banner 370 to be taken to a screen that includes a troubleshooting view 380, which may optionally include a chat icon 385 to allow the user to live chat with an expert on using the medication delivery system to help the user troubleshoot the problem.

Figure 7B:
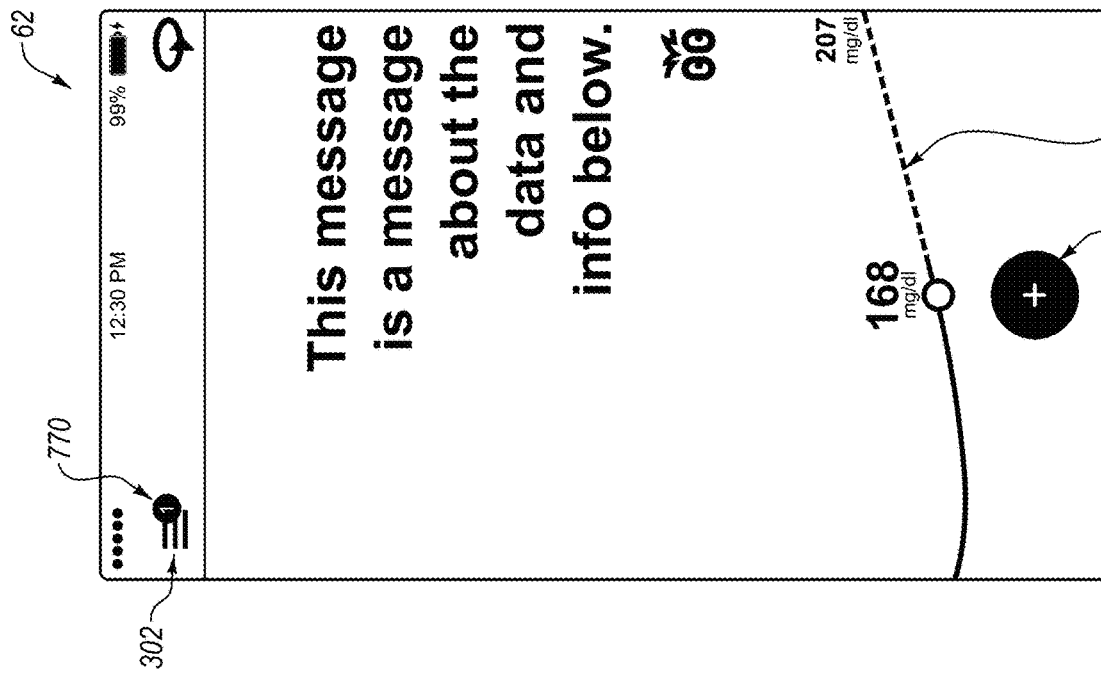
FIG. 7B depicts an example of how a notification may appear on a remote user-interface device.
Figure 7A:
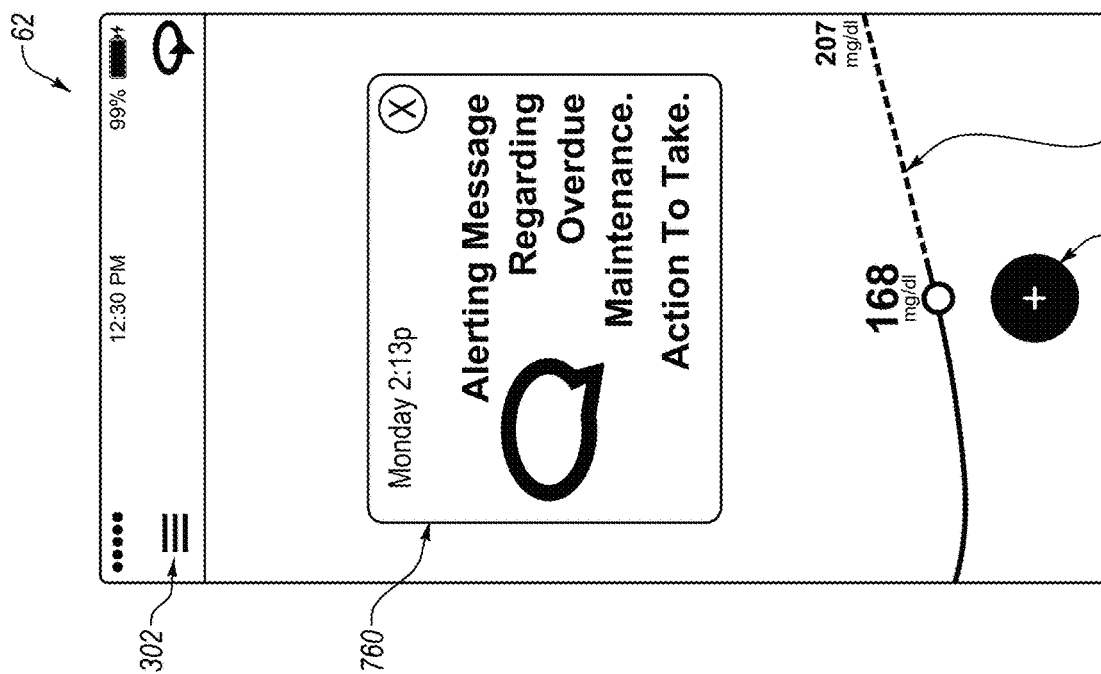
FIG. 7A depicts an example of how an alert may appear on a remote user-interface device.

FIG. 7A depicts an example of how an alert may appear on a remote user-interface device. As shown, an alert may appear as an alert box 760, which may be acknowledged by the user, similar to the way that an alarm can be acknowledged by a user. As shown, the icon in alert box 760 mirrors illuminable icon 245, which can indicate that there is a message available for the user on the remote user-interface device. By having icons mirrored between the remote user-interface and the medication delivery device, the messages associated with each of icons 241-245 can be reinforced in the user's mind. As shown, the message can be about an overdue maintenance task, such as changing any infusion set 149.

FIG. 7B depicts an example of how a notification may appear on a remote user-interface device. Because notifications do not require immediate action, they can appear as a notation 770 on the navigation menu 302 to indicate to the user that a non-urgent message is available for them. In some cases, a snoozed alert can become a notification message available as a notation 770 until such time as an alert snooze time period runs out or the alert condition escalates to a different alarm condition. In some cases, certain alert conditions can become banners after being snoozed.

Figure 8B:
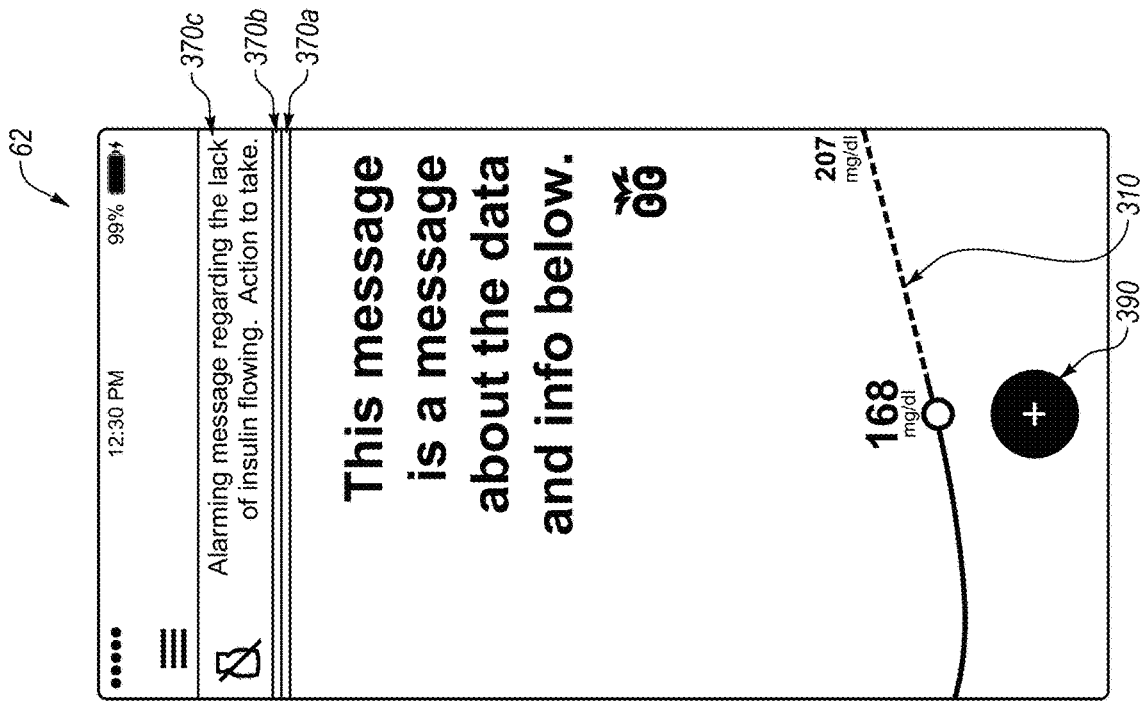
FIGS. 8A and 8B depict examples of how multiple alarms may appear on a remote user-interface device.
Figure 8A:
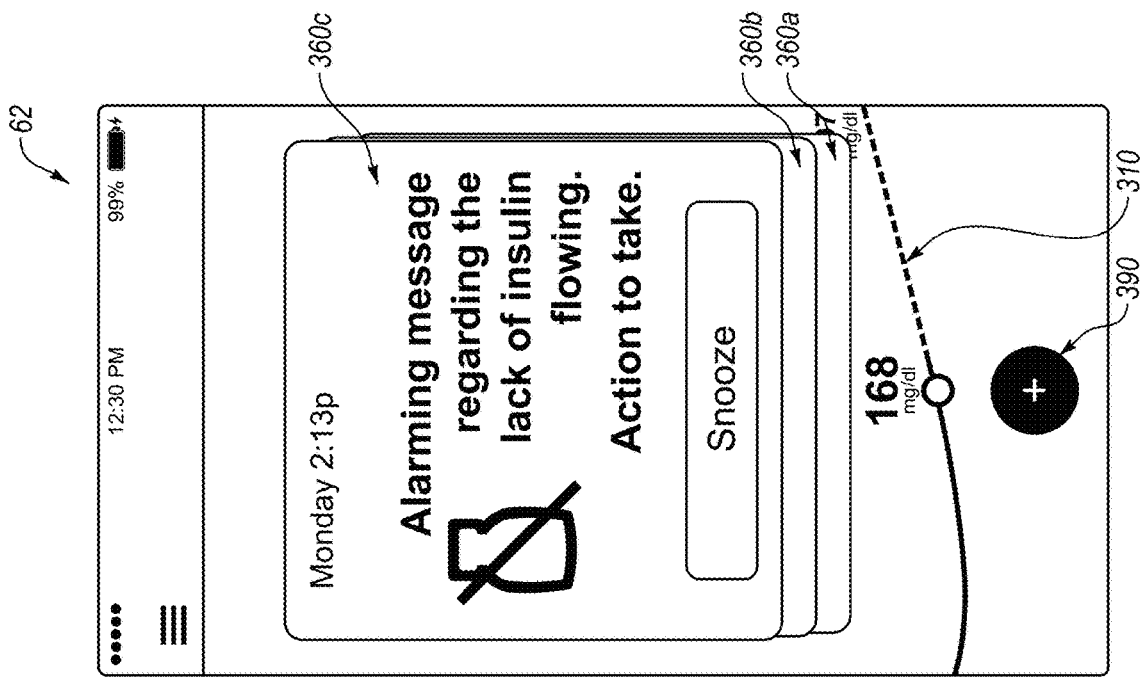

FIGS. 8A and 8B depict examples of how multiple alarms may appear on a remote user-interface device. FIG. 8A depicts multiple alarm boxes 360a, 360b, and 360c stacked on top of each other. As each is cleared, the box underneath is revealed, and each becomes a banner 370a, 370b, 370c, each stacked on top of each other until the user resolves the alarm condition. In some cases, the most recently triggered alarm is stacked on top. In some cases, alarm conditions can have an order of priority and the most urgent alarm condition can be stacked on top. In some cases, alert boxes 760 can be in a stack of boxes. In some cases, alarm and alert boxes can be distinguished by color and/or size. In some cases, the alert boxes 760 may be staggered along the screen (e.g., vertically staggered) such that at least a portion (e.g., an entirety) of each alert box 760 is visible.

Figure 9A:
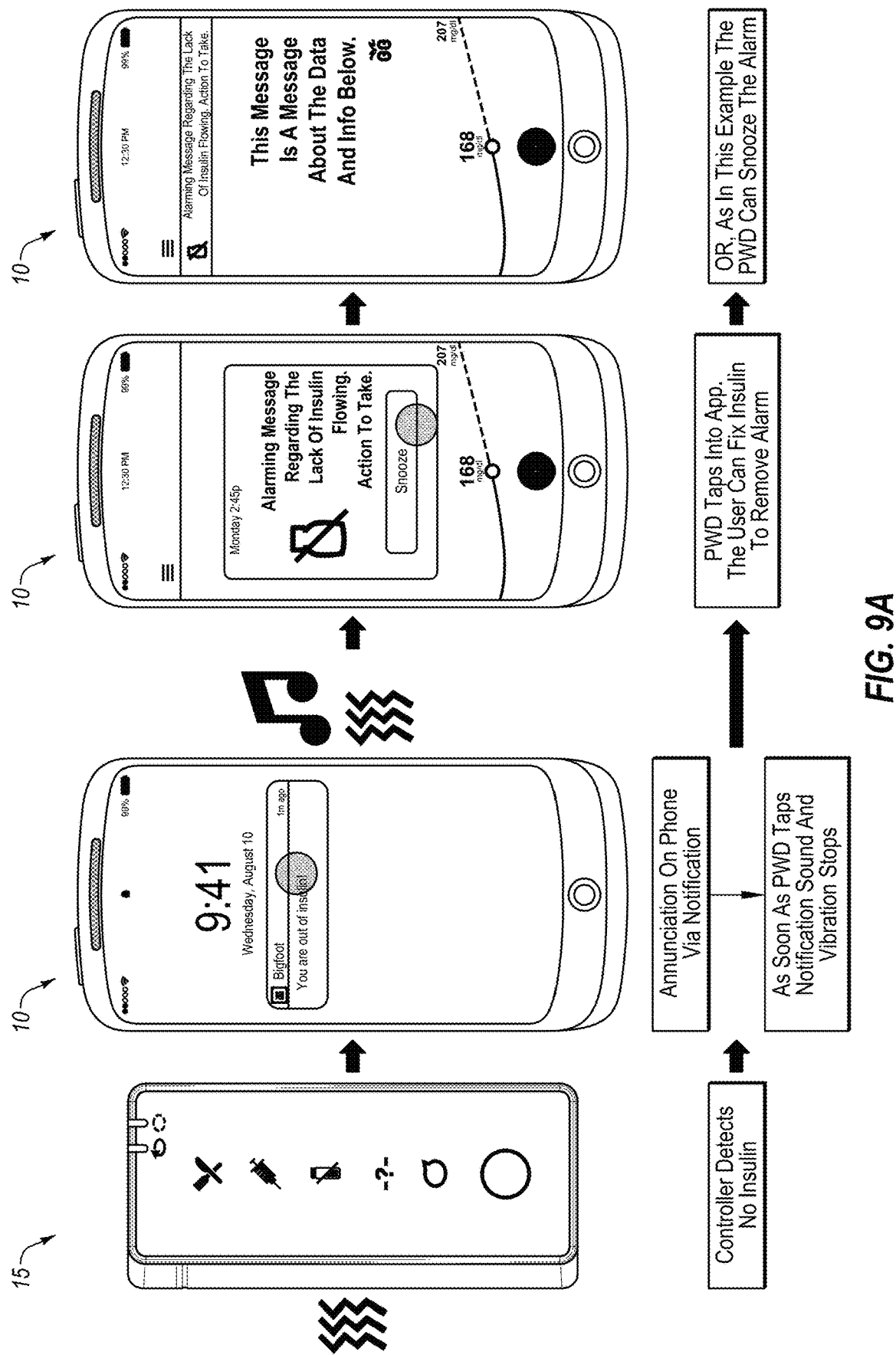
FIG. 9A depicts an example progression of alarm notifications for a lack of insulin flowing if the user acknowledges the alarm condition within a predetermined period of time.

FIG. 9A depicts an example progression of alarm notifications for a lack of insulin flowing if the user acknowledges the alarm condition within a predetermined period of time (where user clicks or acknowledgements are indicated with a circle). As shown, the medication delivery device 15 first detects that there is no insulin or a blockage of insulin and then sends a wireless message to remote user-interface device 10. In some cases, medication delivery device 15 can vibrate upon detecting the alarm condition and/or upon sending the wireless communication. This vibration may be short in duration, and be present in order to let the user know that a notification from the remote user-interface device 10 (e.g., a smartphone, such as an iPHONE®) is from the medication delivery device. After receiving the wireless communication, a message (e.g., an iOS message) can appear on a smartphone version of a remote user-interface device along with sound and/or vibration, assuming that the user permits such notices, vibrations, or sounds for the app of the medication delivery system. The user can then select the message to be brought to the app, where the user can snooze the message and click on the banner to learn how to resolve the issue. In some cases, the user will know how to resolve the issue from experience and not need to click on the banner to resolve the alarm condition.

Figure 9B:
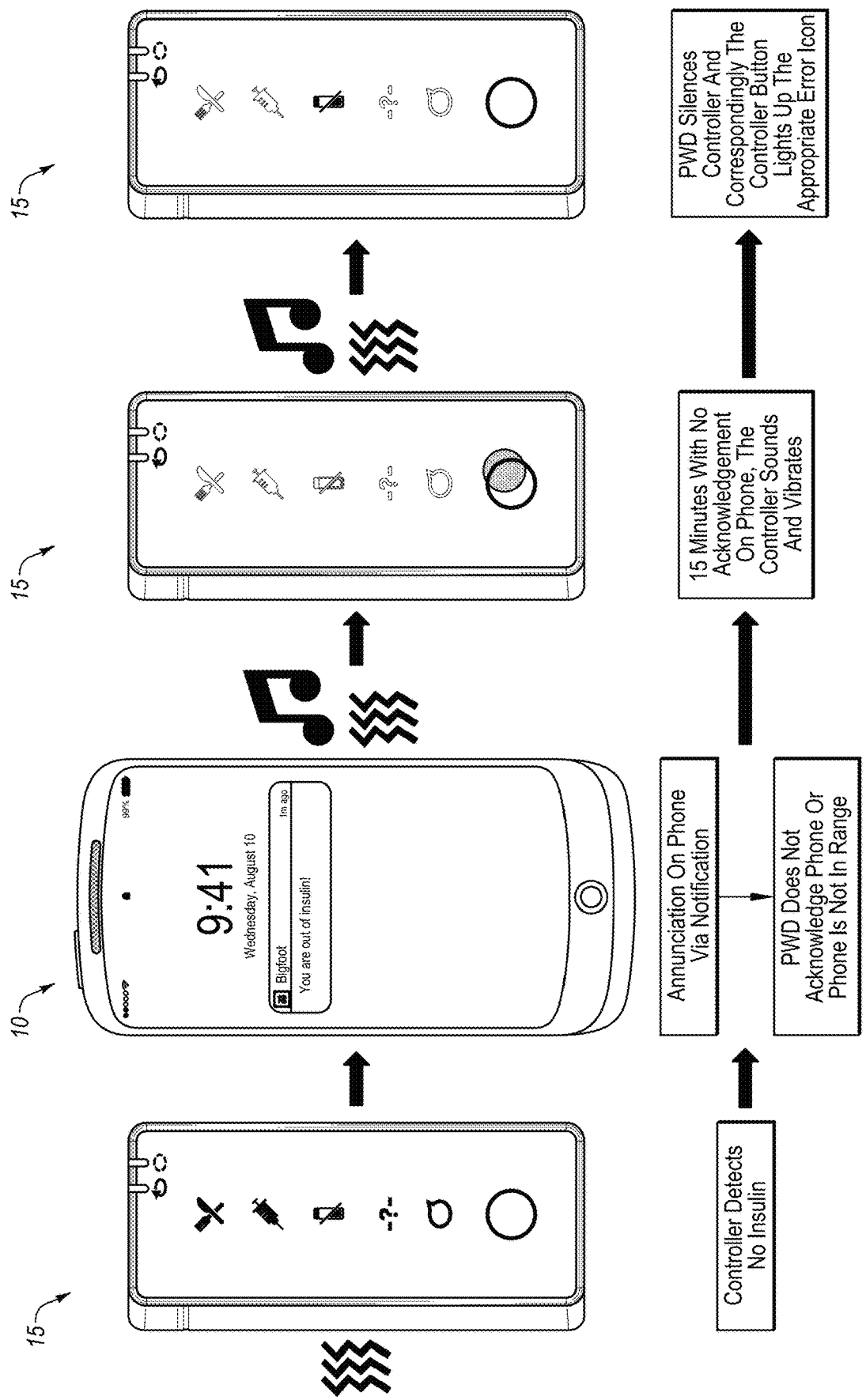
FIG. 9B depicts an example progression of alarm notifications for a lack of insulin flowing if the user fails to acknowledge the alarm condition within a predetermined period of time.

FIG. 9B depicts an example progression of alarm notifications for a lack of insulin flowing if the user fails to acknowledge the alarm condition within a predetermined period of time. This may be due to the smartphone being out of battery, left at home, or having settings on the smartphone that do not allow alarms to be announced. Regardless, if the medication delivery device 15 fails to receive an acknowledgement within a predetermined period of time, which may depend on the type of alarm condition, the medication delivery device can start to vibrate and sound an alarm tone, until the user presses the button to quiet the alarm sound and/or vibration, upon which an icon 243 will illuminate to tell the user that the alarm condition relates to the supply of insulin. In such a situation, an experienced user of the system may know to check to see if there is insulin remaining in the medication delivery device and/or to change out the insulin cartridge for a new cartridge and/or to check for occlusions. In some cases, a user will know to retrieve the remote user-interface device for help in determining how to resolve the alarm condition. After a predetermined period of time (e.g., between 5 seconds and 30 seconds) illuminated icon 243 may be turned off, but the user can again press the button to check the status of the medication delivery device. Additionally of note, neither of the mode lights 236 or 237 is illuminated, indicating that insulin is not being delivered. The alarm on the pump can have a greater duration and/or volume than any sound/vibration made on pump when pump first sends the wireless communication to the smartphone.

While FIGS. 9A-14B illustrate a smartphone as the remote user-interface device, it will be appreciated that any device with any notification scheme with locked devices, unlocked devices, messaging technologies, etc., are contemplated within the scope of the present disclosure. For example, the same approach may be used with ANDROID® devices, iPHONES®, other smartphones, music-playing devices such as an iPOD®, tablet computers, etc.

Figure 10A:
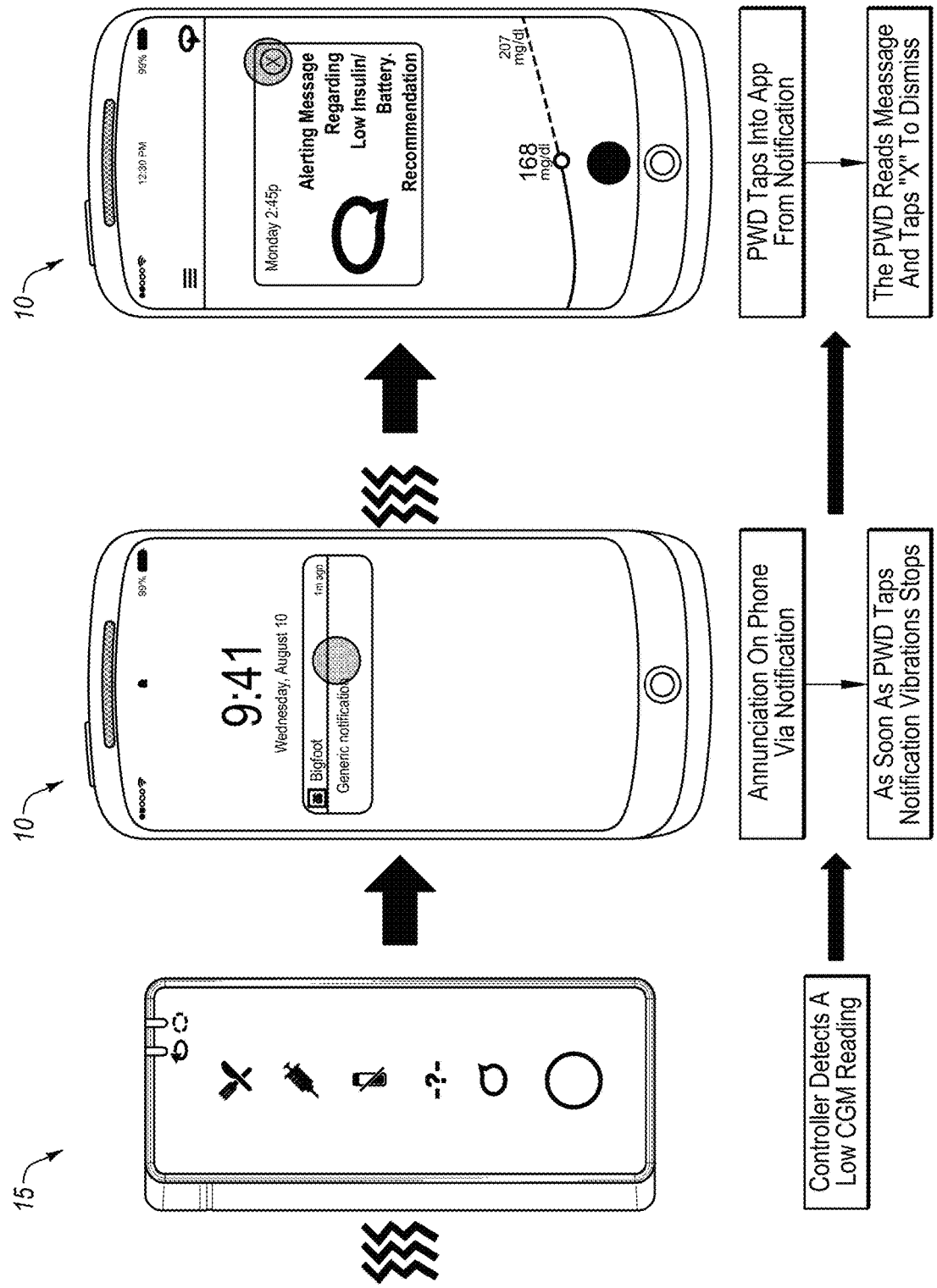
FIG. 10A depicts an example progression of an alert notification regarding battery or insulin levels if the user acknowledges the alert condition within a predetermined period of time.
Figure 10B:
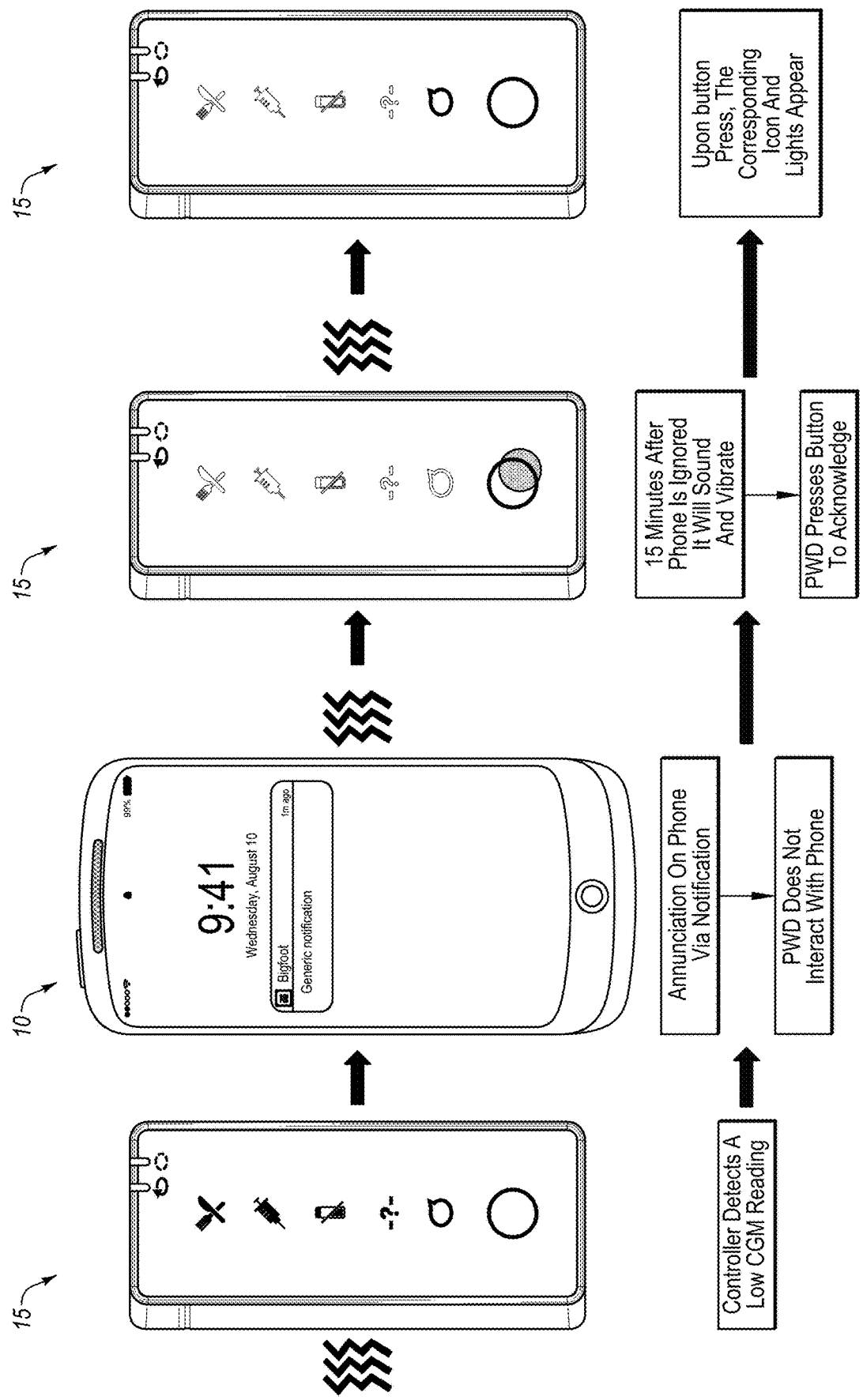
FIG. 10B depicts an example progression of an alert notification regarding battery or insulin levels if the user fails to acknowledge the alarm condition within a predetermined period of time.

FIG. 10A depicts an example progression of an alert notification regarding battery or insulin levels if the user acknowledges the alert condition within a predetermined period of time. FIG. 10B depicts an example progression of an alert notification regarding battery or insulin levels if the user fails to acknowledge the alarm condition within a predetermined period of time. These progressions are similar to that depicted in FIGS. 9A and 9B for an alarm, but involve an alert message, thus the message icon 245 illuminates, with the automation mode indicator light 236 still illuminated if the alarm is snoozed on the medication delivery device or the status is checked. As noted above, the icon displayed for the alert message on the remote user-interface device matches the icon illuminated on the medication delivery device.

Figure 11A:
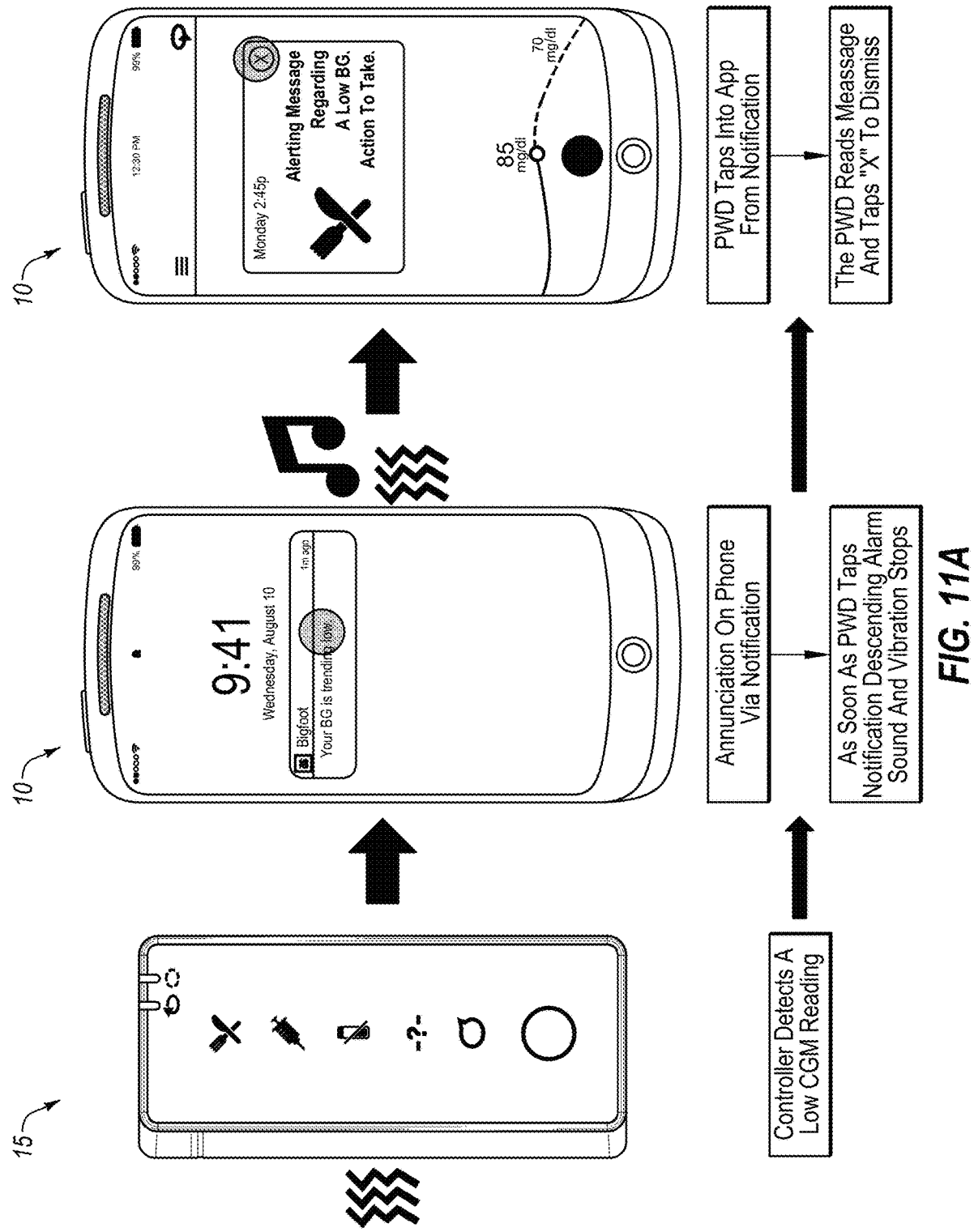
FIG. 11A depicts an example progression of an alert notification regarding a first blood glucose event if the user acknowledges the alert condition within a predetermined period of time.
Figure 11B:
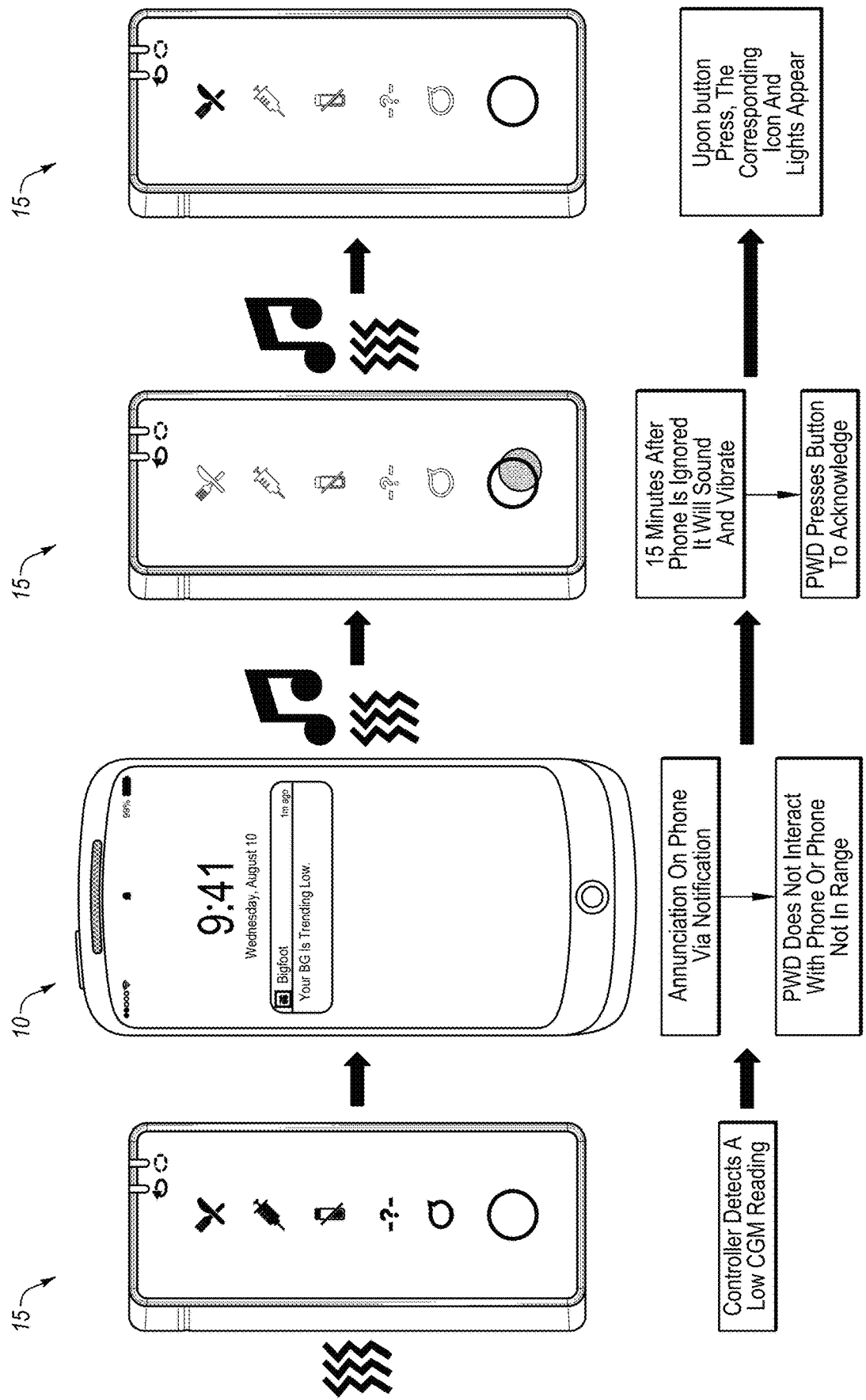
FIG. 11B depicts an example progression of an alert notification regarding a first blood glucose event if the user fails to acknowledge the alarm condition within a predetermined period of time.

FIG. 11A depicts an example progression of an alert notification regarding a first blood glucose event if the user acknowledges the alert condition within a predetermined period of time. FIG. 11B depicts an example progression of an alert notification regarding a first blood glucose event if the user fails to acknowledge the alarm condition within a predetermined period of time. FIGS. 11A and 11B involve an alert regarding a predicted low glucose event that indicates that the user should consume carbohydrates in order to avoid a hypoglycemic condition. Any suitable predictive technique can be used to trigger this alert, which may escalate to an alarm condition if the user reaches a hypoglycemia threshold. The illuminable icon 241 indicating a need to eat on the medication delivery device is again reinforced on the remote user-interface device by using the same icon in the message.

Figure 12A:
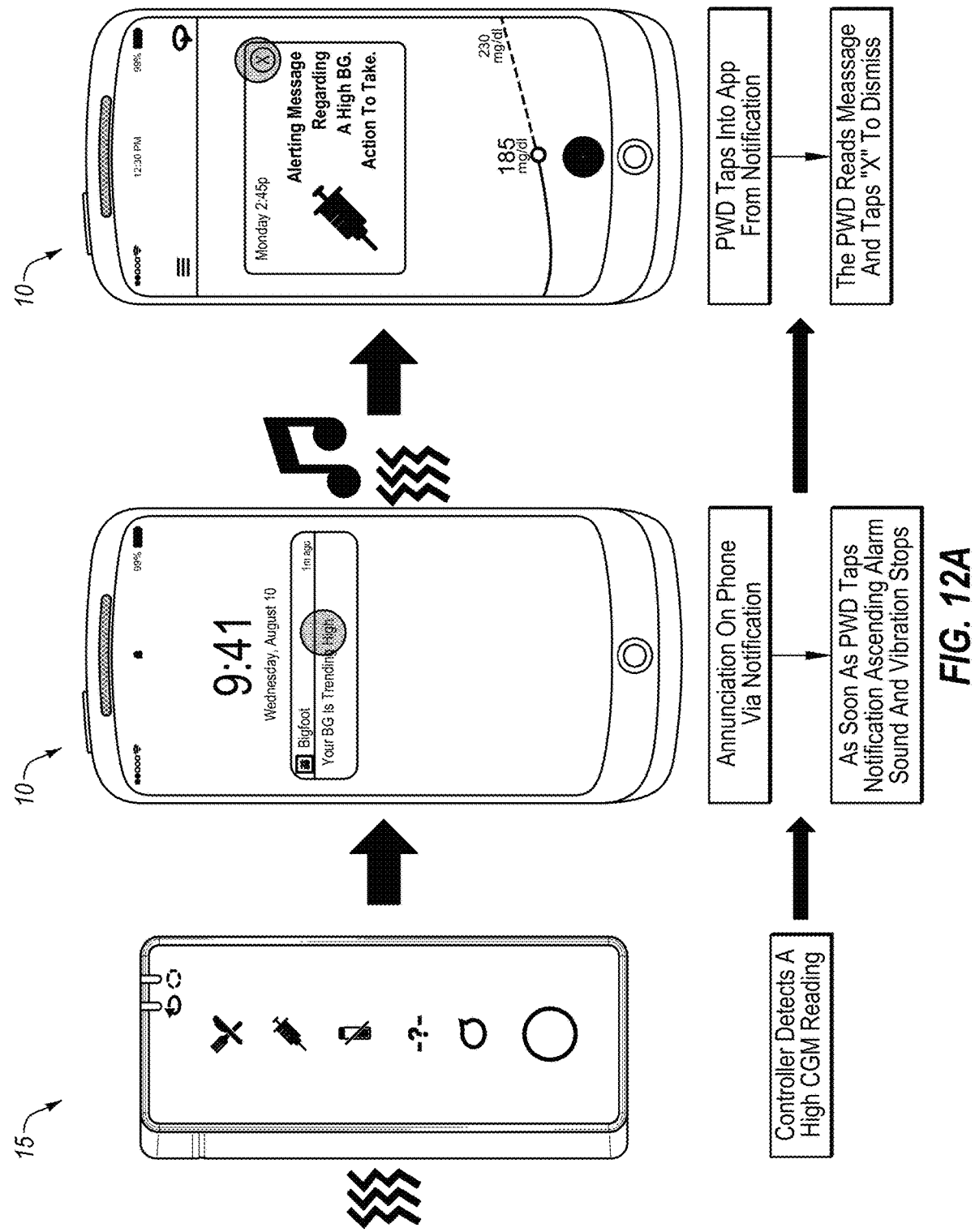
FIG. 12A depicts an example progression of an alert notification regarding a second blood glucose event if the user acknowledges the alert condition within a predetermined period of time.
Figure 12B:
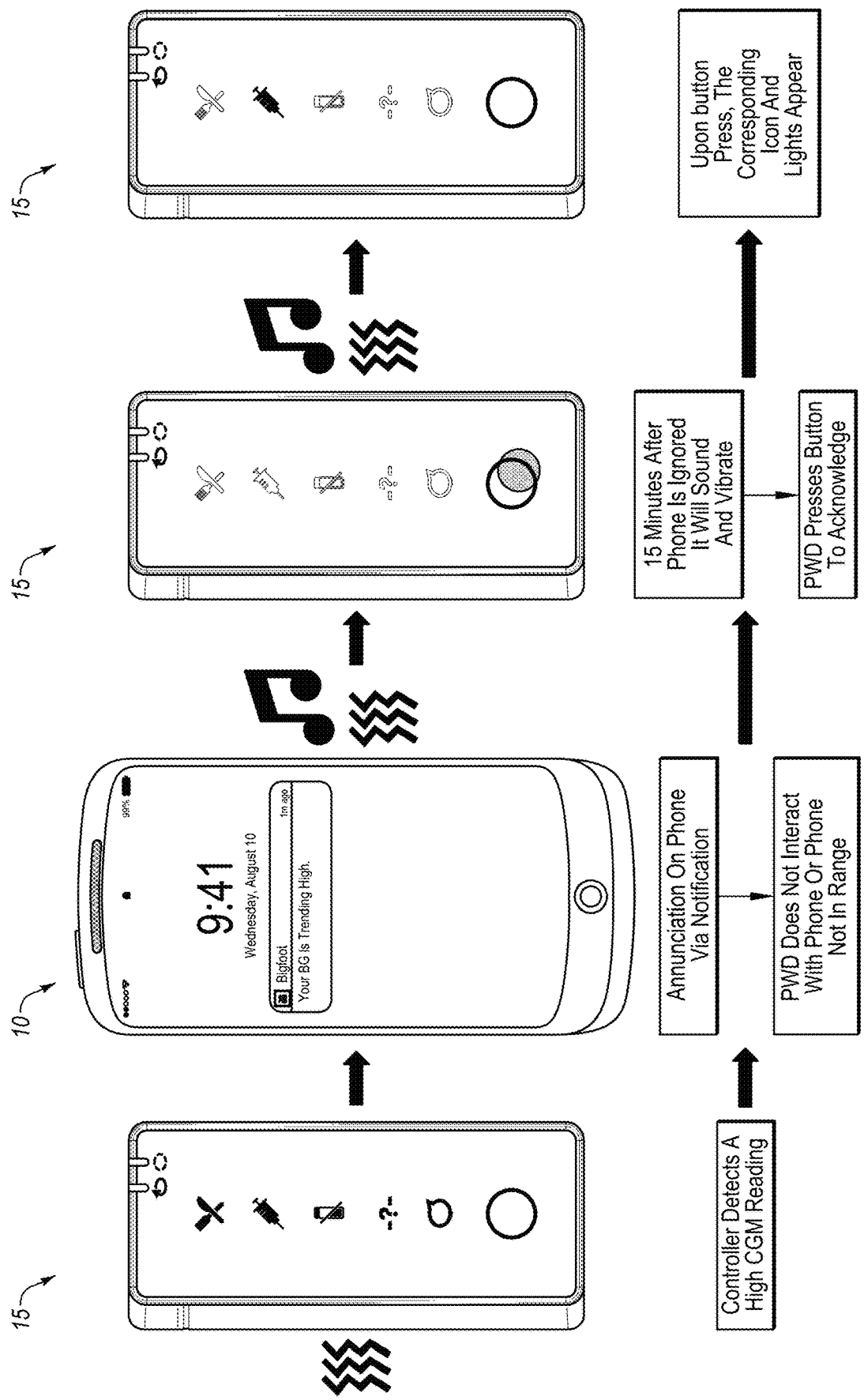
FIG. 12B depicts an example progression of an alert notification regarding a second blood glucose event if the user fails to acknowledge the alarm condition within a predetermined period of time.

FIG. 12A depicts an example progression of an alert notification regarding a second blood glucose event if the user acknowledges the alert condition within a predetermined period of time. FIG. 12B depicts an example progression of an alert notification regarding a second blood glucose event if the user fails to acknowledge the alarm condition within a predetermined period of time. FIGS. 12A and 12B involve an alert condition where the user is predicted to reach and/or stay in a hypoglycemic state without a corrective dose of insulin. In some cases, this alert condition can consider whether the user has announced and/or bolused for a meal. In some cases, this alert condition may be triggered if a meal is consumed and the user neglected to announce or bolus for the meal. Insulin injection icon 242 can indicate the need for the user to administer a bolus of insulin, and again the use of the same icon on the remote user-interface device 10 can reinforce the types of actions the user should take when seeing the icon when the remote user-interface device is not available.

Figure 13A:
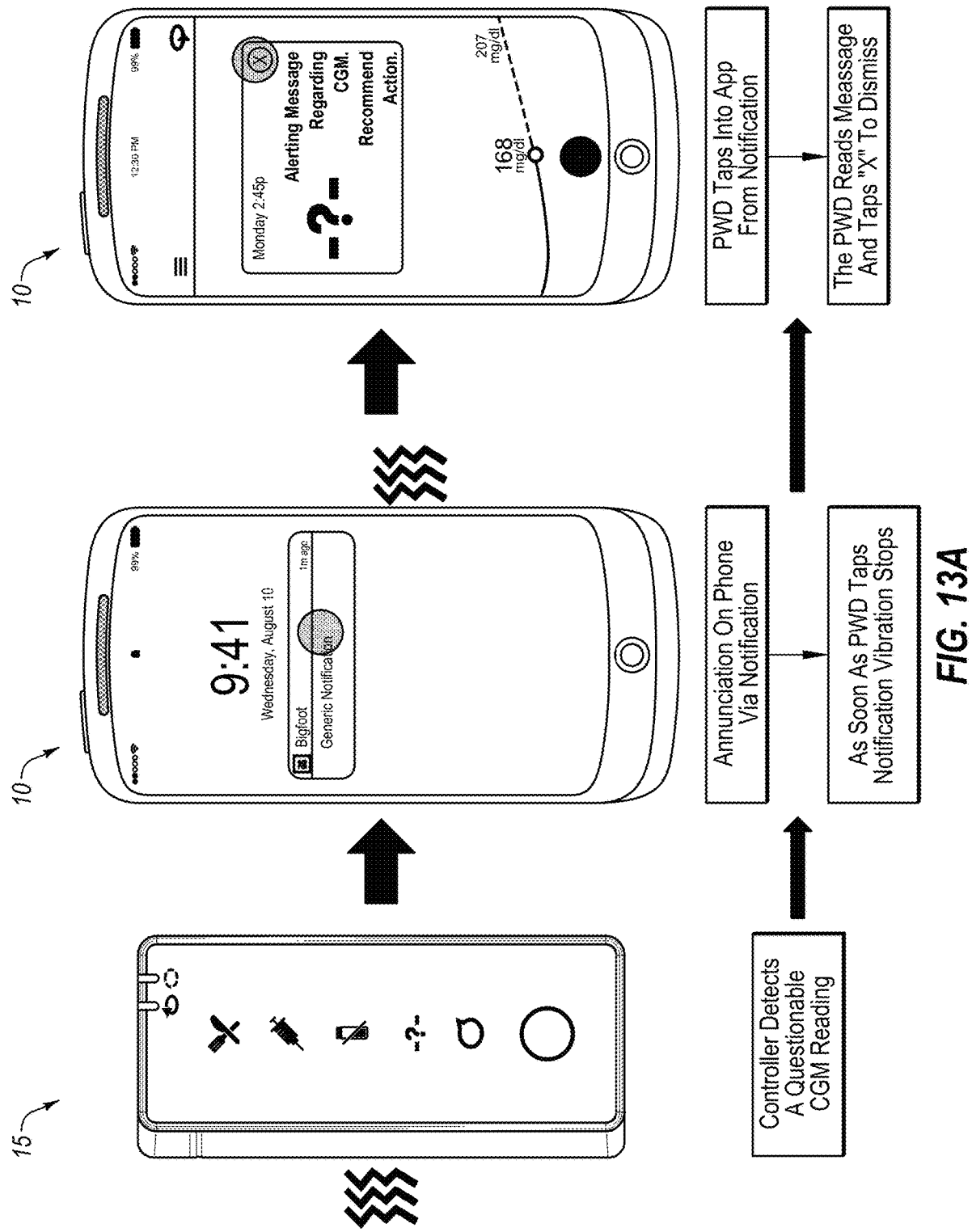
FIG. 13A depicts an example progression of an alert notification regarding a CGM event if the user acknowledges the alert condition within a predetermined period of time.

FIG. 13A depicts an example progression of an alert notification regarding a CGM event if the user acknowledges the alert condition within a predetermined period of time.

Figure 13B:
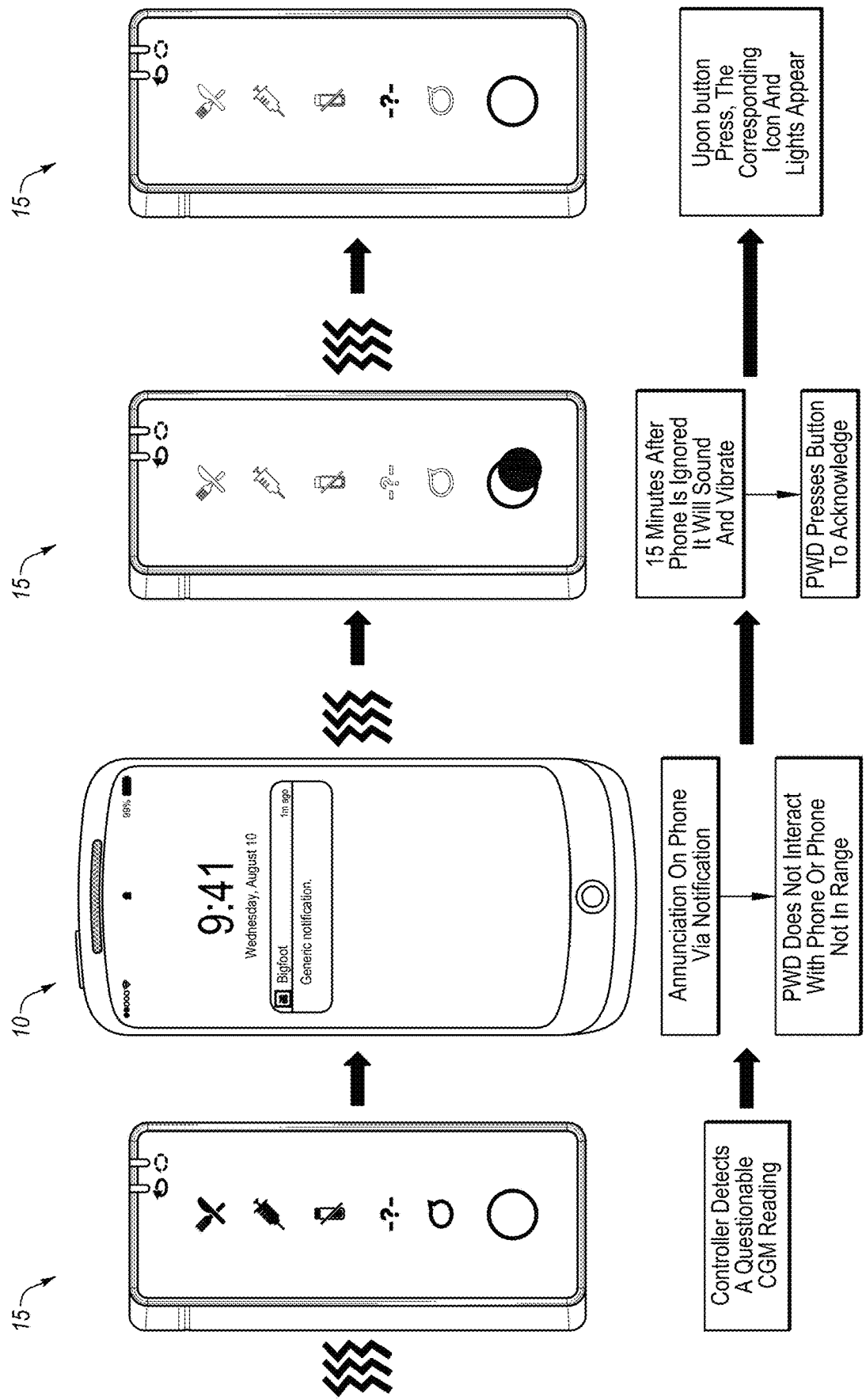
FIG. 13B depicts an example progression of an alert notification regarding a CGM event if the user fails to acknowledge the alarm condition within a predetermined period of time.

FIG. 13B depicts an example progression of an alert notification regarding a CGM event if the user fails to acknowledge the alarm condition within a predetermined period of time. The —?— icon 244 can indicate that the CGM is providing questionable or nonexistent data. In some cases, other icons, such as a triple question mark, can be used to indicate that the CGM is providing unreliable data. Again, the meaning of icon 244 is reinforced by the use of the same icon on the remote user-interface device.

Figure 14A:
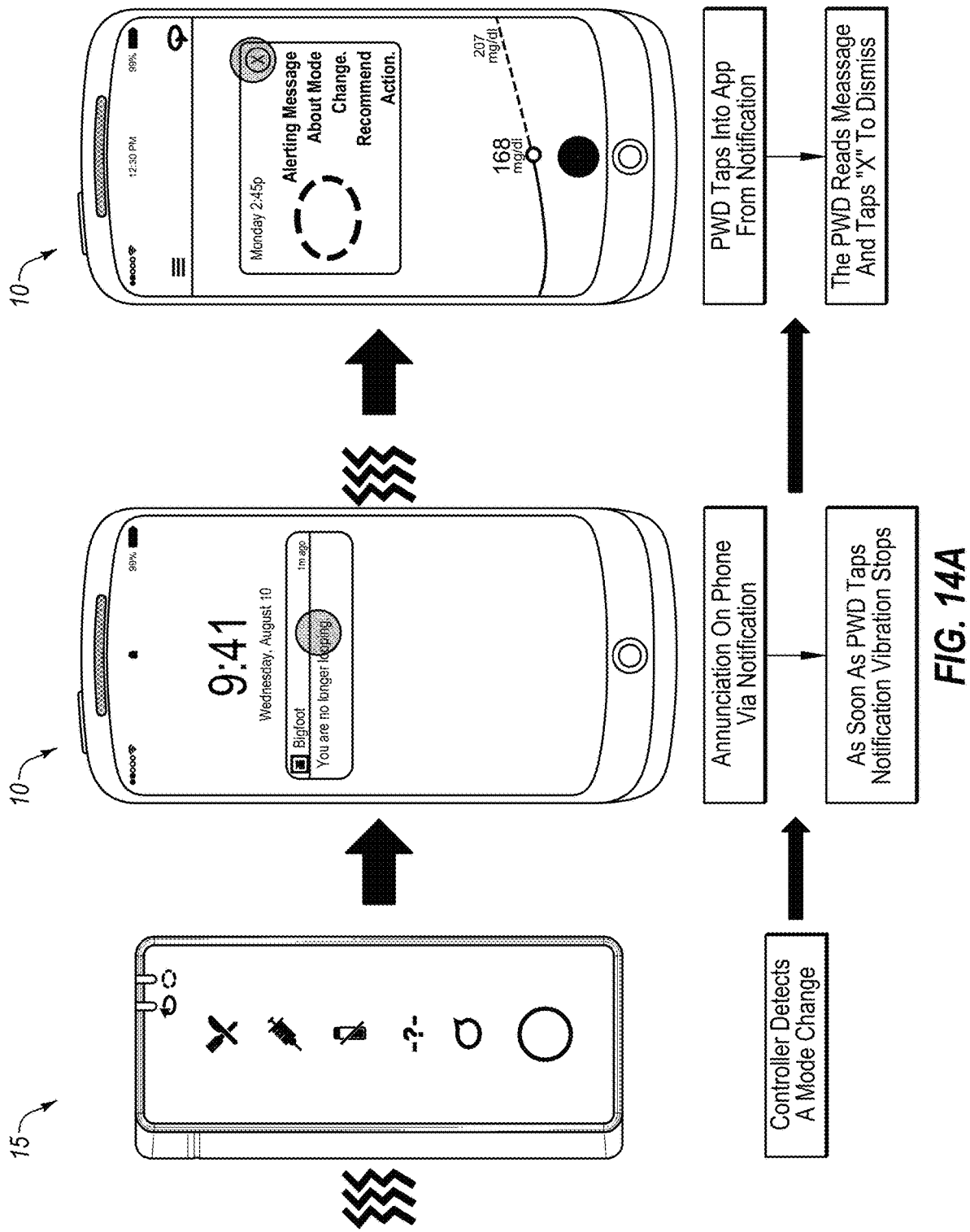
FIG. 14A depicts an example progression of an alert notification regarding a mode change event if the user acknowledges the alert condition within a predetermined period of time.
Figure 14B:
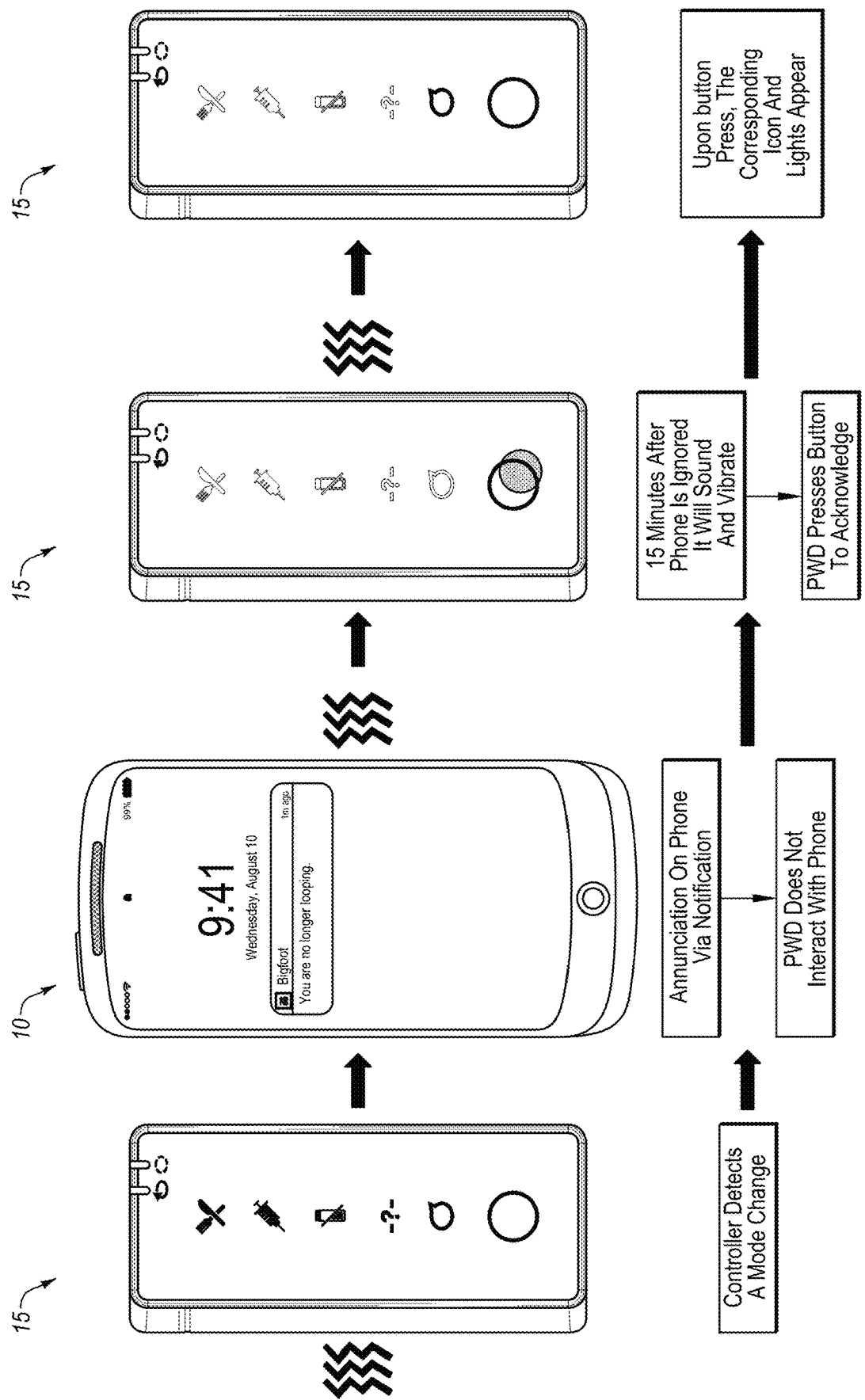
FIG. 14B depicts an example progression of an alert notification regarding a mode change event if the user fails to acknowledge the alarm condition within a predetermined period of time.

FIG. 14A depicts an example progression of an alert notification regarding a mode change event if the user acknowledges the alert condition within a predetermined period of time. FIG. 14B depicts an example progression of an alert notification regarding a mode change event if the user fails to acknowledge the alarm condition within a predetermined period of time. As shown, message icon 245 is issued along with a change of the mode indicator lights to indicate the current mode.

In some cases, alarms may be accompanied by audible alarms (optionally with haptic feedback) while alerts are accompanied by only haptic feedback. As shown in FIGS. 9-14, medication delivery devices can provide some haptic feedback when they send a wireless communication about an alarm or alert condition to a remote user-interface device, which can help a user understand that an alarm or alert coming from the remote user-interface device is coming from the medication delivery device.

In some cases, mode indicator lights 236 and 237 can be positioned along a top surface of the medication delivery device so that a user having the medication delivery device in their pocket can quickly check to ensure that the system is in automated mode without fully removing the medication delivery device from the user's pocket. It is envisioned that these lights will be the most frequently checked, as it will confirm that the medication delivery device is operational, delivering insulin, and indicate the current mode, while other message, alarms, and alerts can be readily evaluated using a remote user-interface device. Additionally or alternatively, any of the lights or icons may be placed at any location on the surface of the medication delivery device to facilitate observation of the icons or lights. The location and arrangement of the various icons and/or lights may be arranged based on any number of factors, including importance to user safety, frequency of use, etc.

Although FIGS. 2-14 depict a certain configuration and use of notification lights, other light configurations and signaling techniques are also envisioned. For example, FIGS. 15A-15C symbolically illustrate how an example pair of notification lights on an automated medication infusion pump can inform a user about the status of the medication delivery system, even without access to the remote user-interface device 10. By pushing a button on or double tapping on the housing of medication delivery device 15 or 15' will illuminate medication delivery indicator light 232 if insulin is being delivered. In some cases, medication delivery indicator light 232 can display different colors to indicate a mode of insulin delivery. In some cases, medication delivery indicator light 232 can remain continuously illuminated or blink to indicate a mode of insulin delivery. In some cases, medication delivery indicator light 232 can display different colors or blink using a different frequency to indicate whether real-time analyte sensor data is being received by medication delivery device 15 or 15'. Message indicator light 234 can be included on medication delivery device 15 or 15' to provide lights indicative of whether there is a message for the user available on remote user-interface device 60. In some cases, the urgency of the message can be conveyed by the color of message indicator light 234 and/or whether message indicator light 234 is blinking. For example, in some cases, message indicator light 234 can be yellow to indicate that a medication delivery device or analyte sensor maintenance activity is due within the next 3 hours. In some cases, message indicator light 234 can illuminate red to indicate that the system requires immediate maintenance and/or that the user has a high or low blood glucose reading. FIG. 15B symbolically illustrates a situation where the analyte sensor and/or the medication delivery device vibrates to indicate the change in mode and/or the presence of a message. As shown, after the vibration pattern, the user can tap the device using a tap pattern (such as a double tap) to stop the vibration and trigger the illumination of indicator lights 232 and 234. In some cases, the vibration will repeat until the user stops the alarm with a tap pattern, which in some cases may be required to match the vibration pattern within a predetermined margin of error. For example, FIGS. 16A and 16B illustrate example alarms and how a user can snooze the alarm or alarms by matching a vibration pattern and/or an alarm pattern (e.g., an alarm pattern of musical notes) with a tap pattern.

As shown in FIG. 15B, medication delivery indicator light 232 is blinking to indicate that the system is not automating medication delivery and message indicator light 234 is yellow to indicate that a message is waiting for the user on the remote user-interface device 10. For example, the message could be a message that the system has entered a non-automated mode because of a loss of analyte sensor data reaching the medication delivery device.

Methods, systems, and devices provided herein can additionally supply an audible alarm or alert to the analyte sensor and/or the medication delivery device (instead of or with vibration) to indicate that the system requires immediate attention. For example, an audible alarm could be triggered if there is an occlusion, if the user has a high or low analyte sensor data point, if the medication delivery device is out of insulin or is expected to be out of insulin in the next hour. FIG. 15C symbolically illustrates a situation where the analyte sensor and/or the medication delivery device vibrates and issues an audible alarm to indicate the need for immediate user interaction with the system. As shown, after the vibration and alarm sound, the user can tap the device using a tap pattern (such as a double tap) to temporarily quiet the vibration and alarm sound and trigger the illumination of indicator lights 232 and 234. In some cases, the tapping will not quiet the alarm if the alarm is more urgent. As shown in FIG. 15C, medication delivery indicator light 232 is off to indicate that the system is not delivering insulin and message indicator light 234 is red to indicate that the system requires immediate attention. In this situation, the user will know that they need to immediately find their remote user-interface device and/or take over responsibility to manage their blood glucose values. In some cases, if the user is unable to find their remote user-interface device, the user will know to check their blood glucose level (e.g., with a blood glucose meter) and find insulin from another source if additional insulin is needed.

Further example embodiments are listed below.

Embodiment 1: An on-body networked medication-delivery system comprising: an analyte sensor adapted to generate analyte data for a user and wirelessly transmit the analyte data; a medication delivery device in wireless communication with the analyte sensor, the medication delivery device comprising: a medication reservoir or a space to receive a medication reservoir; a drive system adapted to meter the administration of medication out of the medication delivery device; a feature to provide audible, visual, or haptic feedback to a user; a controller adapted to change a dosage of medication based at least in part on the analyte sensor data and adapted to issue alarm and alert wireless communications based on a detection of an alarm or alert condition; and a tap detector or button adapted to permit the user to check the status of the medication delivery device or to acknowledge alert or alarm conditions; and a remote user-interface device in wireless communication with the medication delivery device, the remote user-interface device being adapted to receive the alarm and alert wireless communications from the controller and provide an audible, visual, or haptic alarm or alert message to the user and permit the user to acknowledge an associated alarm or alert condition, the remote user-interface device being adapted to wirelessly communicate each acknowledgement to the controller, wherein the controller is adapted to trigger an audible, visual, or haptic alarm or alert message via a feature to provide audible, visual, or haptic feedback if the controller fails to receive an acknowledgement of the alert or alarm condition within a predetermined period of time after the controller issues the alarm and alert wireless communication.

Embodiment 2: The system of Embodiment 1, wherein the system is a diabetes management system, the medication delivery device is an insulin pump, and the analyte sensor is a continuous glucose monitor.

Embodiment 3: The system of Embodiment 1 or Embodiment 2, wherein the medication delivery device is a patch pump.

Embodiment 4: The system of one of Embodiments 1-3, wherein the medication delivery device comprises a durable controller and a disposable pump body, each having a housing and being removably connectable, the disposable pump body comprising at least the medication reservoir or a space to receive a medication reservoir and the durable controller comprising at least the feature(s) to provide audible, visual, or haptic feedback, the controller, and the tap detector or button.

Embodiment 5: The system of one of Embodiments 1-4, wherein the medication delivery device comprises a button.

Embodiment 6: The system of one of Embodiments 1-5, wherein the feature(s) to provide audible, visual, or haptic feedback to a user comprises at least one light associated with an icon.

Embodiment 7: The system of Embodiment 6, wherein the remote user-interface device is adapted to present the icon for an alarm or alert condition.

Embodiment 8: The system of Embodiment 7, wherein the at least one light associated with the icon does not illuminate on the housing until the tap detector detects a tap, or the button is pressed, or until the predetermined period of time.

Embodiment 9: The system of one of Embodiments 1-8, wherein a user can acknowledge an audible, visual, or haptic alarm or alert message provided by a remote user-interface device by tapping the medication delivery device or pressing the button on the medication delivery device even before the medication delivery device triggers the audible, visual, or haptic alarm or alert message via the feature(s) to provide audible, visual, or haptic feedback.

Embodiment 10: The system of one of Embodiments 1-9, wherein the feature(s) to provide audible, visual, or haptic feedback comprises a vibration motor adapted to provide haptic feedback, wherein the controller is adapted to provide haptic feedback or audible feedback, upon issuing the alarm and alert wireless communications, wherein the audible alarm or alert message triggered if the controller fails to receive an acknowledgement of the alert or alarm condition within a predetermined period of time is louder or longer in duration than the haptic feedback or audible feedback provided when the controller issues the alarm and alert wireless communications.

Embodiment 11: The system of one of Embodiments 1-10, wherein the predetermined period of time is at least 30 seconds and no greater than 1 hour, between 1 minute and 30 minutes, between 3 minutes and 20 minutes, or between 5 minutes and 15 minutes, wherein the predetermined period of time for an alarm or alert condition can depend on the alarm or alert condition.

Embodiment 12: The system of one of Embodiments 1-11, wherein an acknowledgement of an alarm or alert will quiet audible or haptic feedback for the alarm or alert condition for a predetermined snooze period of time, wherein the controller is adapted to issue new alarm and alert wireless communications after the predetermined snooze period of time if the alarm or alert condition is still detected as being present.

Embodiment 13: The system of one of Embodiments 1-12, wherein the remote user-interface device is adapted to present the user with troubleshooting instructions using text, audio, or video to remove the alarm or alert condition, wherein the medication delivery device does not present any troubleshooting instructions using text, audio, or video.

Embodiment 14: The system of one of Embodiments 1-13, wherein the medication delivery device comprises a housing that contains a non-rechargeable, non-replaceable battery.

Embodiment 15: The system of one of Embodiments 1-4, wherein the remote user-interface device is adapted to allow a user to send instructions to the medication delivery device using the remote user-interface device, wherein the remote user-interface device can prompt the user to confirm the instructions by pressing the button or tapping the controller under certain conditions.

Embodiment 16: The system of Embodiment 15, wherein the controller is adapted to require a user to confirm a bolus delivery by pressing the button or tapping the controller if the dosage is determined by the controller to be unusual based on typical dosage amounts administered by the user, based on the timing the dosage or the timing of a previous dosage, or based on a prediction of how the dosage will change analyte levels for the user.

Embodiment 17: The system of one of Embodiments 1-16, wherein the medication delivery device comprises one or more icons, and one or more lights associated with those one or more icons, indicating whether the medication is being delivered based on the analyte sensor or not or whether there is an error with the analyte sensor.

Embodiment 18: The system of one of Embodiments 1-17, wherein the medication delivery device comprises one or more icons, and one or more lights associated with those one or more icons, indicating that an amount of medication in the medication delivery device is below a threshold level.

Embodiment 19: The system of one of Embodiments 1-18, wherein the medication delivery device comprises one or more icons, and one or more lights associated with those one or more icons, indicating that the user should administer more medication or consume carbohydrates.

Embodiment 20: The system of one of Embodiments 1-19, wherein the medication delivery device comprises one or more icons, and one or more lights associated with those one or more icons, indicating that a more detailed message for the user is awaiting the user on the remote user-interface device.

Embodiment 21: A method for issuing alarms and alerts in an on-body networked diabetes management system, the method comprising: receiving glucose sensor data from a continuous glucose monitor; determining a dosage of insulin delivery based at least in part on the glucose sensor data; detecting an alarm or alert condition; sending a wireless communication regarding the alarm or alert condition to a remote user-interface device; triggering an audible, visual, or haptic alarm or alert on the insulin delivery device if the insulin delivery device does not receive an acknowledgement of the alarm or alert condition within a predetermined period of time.

Embodiment 22: The method of Embodiment 21, wherein the user can acknowledge the alarm by pressing a button on the insulin delivery device or by tapping the insulin delivery device and by interacting with the remote user-interface device, wherein the insulin delivery device can receive an acknowledgement of the alarm or alert condition as part of a wireless communication from the remote user-interface device.

Embodiment 23: The method of Embodiment 21 or Embodiment 22, further comprising triggering audible or haptic feedback of the insulin delivery device when sending the wireless communication regarding the alarm or alert condition to the remote user-interface device, wherein the audible, visual, or haptic alarm or alert on the insulin delivery device after the predetermined period of time is louder or longer in duration than the feedback initiated when sending the wireless communication.

Embodiment 24: The method of one of Embodiments 21-23, further comprising stopping the audible, visual, or haptic alarm or alert on the insulin delivery device when a button on the insulin delivery device is pressed.

Embodiment 25: The method of Embodiment 24, wherein the button must be pressed at least twice during a predetermined period of time or according to a predetermined pattern for the audible, visual, or haptic alarm or alert to be stopped.

Embodiment 26: The method of Embodiment 24 or 25, wherein stopping the audible, visual, or haptic alarm or alert on the insulin delivery device prevents the triggering of any audible, visual, or haptic alarms or alerts regarding that alarm or alert condition or the sending of any wireless communication regarding the alarm or alert condition for a predetermined period of time, wherein the process of Embodiment 21 will repeat after the predetermined period of time if the alarm or alert condition is present after the predetermined period of time.

Embodiment 27: The method of one of Embodiments 21-26, wherein the alarm or alert condition is an indication of a change from a first mode of operation to a second mode of operation.

Embodiment 28: The method of one of Embodiments 21-26, wherein the alarm or alert condition is an indication of an amount insulin remaining in the insulin delivery device being below a threshold level.

Embodiment 29: The method of one of Embodiments 21-26, wherein the alarm or alert condition is an indication of a low glucose condition or a high glucose condition.

Embodiment 30: The method of Embodiment 29, wherein the audible, visual, haptic alarm or alert on the insulin delivery device includes the illumination of an icon or next to an icon indicating that the user should eat or should administer insulin.

Embodiment 31: The method of one of Embodiments 21-26, wherein the alarm or alert condition is a notice that the continuous glucose monitor is not working, not in range, or not reliable.

Embodiment 32: The method of one of Embodiments 21-26, wherein the alarm or alert condition is a notice about a possible occlusion, a possible air bubble, a possible missed meal announcement, a possible need to change an infusion set, a possible need to calibrate a CGM, a possible need to replace the CGM, or a possible need to check ketone levels, wherein the audible, visual, haptic alarm or alert on the insulin delivery device includes the illumination of an icon or next to an icon indicating that the user should check the remote user-interface device for information about the alert.

Embodiment 33: An insulin delivery device adapted for wireless communication with a continuous glucose monitor and a remote user-interface device, the insulin delivery device comprising: an insulin reservoir or a space to receive an insulin reservoir; a drive system adapted to meter the administration of insulin out of the insulin delivery device; a wireless transmitter and receiver adapted to send and receive wireless communications from at least a continuous glucose monitor and a remote user-interface device; a controller adapted to change a dosage of medication based at least in part on data from the continuous glucose monitor and adapted to issue alarm and alert wireless communications based on a detection of an alarm or alert condition; a housing containing at least the controller and the wireless transmitter and receiver; a tap detector within the housing or a button on the housing adapted to permit the user to check the status of the insulin delivery device or to acknowledge alert or alarm conditions; and one or more lights adapted to illuminate icons or adjacent to icons on the housing indicating a mode of operation of the insulin delivery device and whether insulin is being delivered to the user.

Embodiment 34: The device of Embodiment 33, further comprising one or more lights adapted to illuminate icons or adjacent to icons on the housing indicating that a message is awaiting the user on the remote user-interface device.

Embodiment 35: The device of Embodiment 33 or Embodiment 34, further comprising one or more lights adapted to illuminate icons or adjacent to icons on the housing indicating that the user has a blood glucose condition requiring the consumption of carbohydrates or the administration of additional insulin.

Embodiment 36: The device of Embodiment 35, wherein the user cannot administer additional insulin using the insulin delivery device without accessing the remote user-interface device.

Embodiment 37: The device of Embodiment 36, wherein the controller is adapted to evaluate whether a wireless communication from a remote user-interface device is within one or more predefined parameters.

Embodiment 38: The device of Embodiment 37, wherein the controller is adapted to send a wireless communication to the remote user-interface device indicating that a bolus is outside of one or more predefined parameters, or indicating the user must confirm the bolus on the insulin delivery device by tapping or pressing the button.

Embodiment 39: The device of one of Embodiments 33-38, further comprising one or more lights adapted to illuminate icons or adjacent to icons on the housing indicating that the insulin delivery device has less than a threshold amount of insulin remaining.

Embodiment 40: The device of one of Embodiments 33-39, further comprising one or more lights adapted to illuminate icons or adjacent to icons on the housing indicating that there is a problem with the data being received, or a lack of data being received, from the continuous glucose monitor.

Embodiment 41: A medication delivery system comprising a medication delivery device and a remote user-interface device, the medication delivery device and the remote user-interface device being in wireless communication, the medication delivery device being adapted to automatically administer medication according to programmed rate, a programmed schedule, or based on analyte sensor data without user input, the remote user-interface device being adapted to receive user commands for the medication delivery device to administer additional doses of medication, adjust the programmed delivery rate or schedule, or adjust an algorithm that determines a dosage based on the analyte sensor data, wherein both the remote user-interface device and the medication delivery device are adapted to provide audible, visual, or haptic feedback to issue an alarm or alert regarding the ability of the medication delivery device to deliver medication, wherein the medication delivery device is adapted to detect a condition that prevents the delivery of medication and is adapted to send an alarm wireless communication to the remote user-interface device regarding the condition, wherein the remote user-interface device issues an audible, visual, or haptic alarm when the alarm wireless communication is received and provides a feature for the user to acknowledge the alarm, wherein the remote user-interface device sends an acknowledgement wireless communication to the medication delivery device upon the user acknowledging the alarm, wherein the medication delivery device is adapted to issue an audible, visual, or haptic alarm after a predetermined period of time after the alarm wireless communication is sent unless the medication delivery device receives the acknowledgement wireless communication during the predetermined period of time.

Embodiment 42: The medication delivery system of Embodiment 41, wherein the medication delivery device includes a feature to receive a user's acknowledgement of an audible, visual, or haptic alarm to silence the alarm.

Embodiment 43: The medication delivery system of Embodiment 41 or Embodiment 42, wherein the medication delivery device is an insulin infusion pump, wherein the medication is insulin, and wherein the remote user-interface device is a smartphone.

Embodiment 44: The medication delivery system of Embodiment 43, further comprising a continuous glucose monitor in wireless communication with the insulin infusion pump, wherein the insulin infusion pump delivers different amounts or rates of insulin based on glucose data from the continuous glucose monitor.

Embodiment 45: The medication delivery system of Embodiment 44, wherein the insulin infusion pump is not adapted to display specific concentrations of the glucose data, but is adapted to send glucose data wireless communications to the smartphone, wherein the smartphone is adapted to display specific concentrations of the glucose data.

Embodiment 46: The medication delivery system of Embodiment 45, wherein the insulin infusion pump is adapted to illuminate one or more icons, or a light next to one or more icons, that indicate that the user is in or expected to experience hypoglycemic state or a hyperglycemic state, that indicate that the user should administer more insulin, or that indicate that the user should consume food, wherein the light becomes illuminated when the insulin infusion pump issues an issue an audible, visual, or haptic alarm or when the user acknowledges the alarm on the insulin infusion pump.

Embodiment 47: The medication delivery system of one of Embodiments 43-46, wherein the insulin infusion pump is adapted to illuminate one or more icons, or a light next to one or more icons, that indicate that the user is in out of insulin, wherein the light becomes illuminated when the insulin infusion pump issues an issue an audible, visual, or haptic alarm or when the user acknowledges the alarm on the insulin infusion pump.

While certain embodiments have been described and shown in the accompanying drawings, such embodiments are merely illustrative and not restrictive of the scope of the disclosure, and this disclosure is not limited to the specific constructions and arrangements shown and described, since various other additions and modifications to, and deletions from, the described embodiments will be apparent to one of ordinary skill in the art. Thus, the scope of the disclosure is only limited by the literal language, and legal equivalents, of the claims that follow.

What is claimed is:

1. A networked medication-delivery system comprising:
    an analyte sensor adapted to generate analyte data for a user and transmit the analyte data;
    a medication delivery device in communication with the analyte sensor; and
    a remote user-interface device in communication with the medication delivery device,
    wherein the medication delivery device is configured to indicate, via one or more of an icon or an indicator light of the medication delivery device, that a message related to medication delivery is waiting at the remote user-interface device.

2. The networked medication-delivery system of claim 1, wherein the medication delivery device comprises:
    a drive system configured to administer medication from the medication delivery device;
    a feedback element configured to provide audible, visual, or haptic feedback to the user;
    a controller configured to:
        determine or change a dosage of medication based at least partially on the analyte data;
        detect an alarm condition; and
        issue an alarm based the detected alarm condition; and
    a user-selectable element configured to permit the user to perform one or more of check a status of the medication delivery device or acknowledge an alarm condition.

3. The networked medication-delivery system of claim 2, wherein the medication delivery device is configured to receive a medication reservoir.

4. The networked medication-delivery system of claim 3, wherein the medication delivery device further comprises a user interface comprising:
    the icon; and
    the indicator light associated with the icon.

5. The networked medication-delivery system of claim 4, wherein the remote user-interface device is configured to:
    receive data regarding the alarm condition from the controller;
    provide an audible, visual, or haptic alarm or alert message to the user; and
    enable the user to acknowledge an alarm condition.

6. The networked medication-delivery system of claim 5, wherein the remote user-interface device is configured to transmit each acknowledgement to the controller of the medication delivery device.

7. The networked medication-delivery system of claim 1, wherein the medication delivery device comprises an insulin pump, and the analyte sensor comprises a continuous glucose monitor.

8. The networked medication-delivery system of claim 1, wherein the medication delivery device comprises a patch pump.

9. The networked medication-delivery system of claim 1, wherein the medication delivery device comprises a durable controller and a disposable pump body, each having a housing and being removably connectable.

10. The networked medication-delivery system of claim 9, wherein the disposable pump body comprises a space to receive a medication reservoir, and wherein the durable controller comprises a feedback element to provide audible, visual, or haptic feedback to the user.

11. The networked medication-delivery system of claim 10, wherein the medication delivery device is configured to enable the user to acknowledge an alarm condition provided by the remote user-interface device by tapping the medication delivery device or pressing a user-selectable element on the medication delivery device.

12. The networked medication-delivery system of claim 11, wherein the medication delivery device is configured to enable the user to acknowledge the alarm condition before the medication delivery device triggers the audible, visual, or haptic alarm or alert message via a feedback element of the medication delivery device.

13. The networked medication-delivery system of claim 12, wherein the feedback element comprises a vibration motor adapted to provide haptic feedback.

14. The networked medication-delivery system of claim 12, wherein the medication delivery device is configured to increase a volume or duration of the audible, visual, or haptic alarm or alert message responsive to failing to receive an acknowledgement of the alarm within a predetermined period of time.

15. The networked medication-delivery system of claim 12, wherein the medication delivery device is configured to decrease a volume or duration of the audible, visual, or haptic alarm or alert message responsive to receiving an acknowledgement of the alarm within a predetermined period of time.

16. The networked medication-delivery system of claim 12, wherein the medication delivery device is configured to issue a new alarm after a predetermined snooze period of time if the alarm has not been acknowledged.

17. An insulin delivery device configured for wireless communication with a continuous glucose monitor and a remote user-interface device, the insulin delivery device comprising:
- a housing containing at least a controller and a wireless transmitter and receiver;
- one or more of a tap detector within the housing or a button on the housing configured to permit a user to check a status of the insulin delivery device or to acknowledge an alarm condition; and
- one or more lights adapted to illuminate icons or adjacent to icons on the housing indicating that a message related to insulin delivery is waiting at the remote user-interface device.

* * * * *